(12) United States Patent
Goldstein

(10) Patent No.: US 12,144,889 B2
(45) Date of Patent: Nov. 19, 2024

(54) METHODS OF TREATING ALLERGIC CONJUNCTIVITIS

(71) Applicant: OCULAR THERAPEUTIX, INC., Bedford, MA (US)

(72) Inventor: Michael Goldstein, Cambridge, MA (US)

(73) Assignee: OCULAR THERAPEUTIX, INC., Bedford, MA (US)

( * ) Notice: Subject to any disclaimer, the term of this patent is extended or adjusted under 35 U.S.C. 154(b) by 0 days.

(21) Appl. No.: 17/673,331

(22) Filed: Feb. 16, 2022

(65) Prior Publication Data

US 2022/0218601 A1 Jul. 14, 2022

Related U.S. Application Data

(63) Continuation of application No. PCT/US2021/029184, filed on Apr. 26, 2021.

(60) Provisional application No. 63/173,660, filed on Apr. 12, 2021, provisional application No. 63/128,565, filed on Dec. 21, 2020, provisional application No. 63/016,030, filed on Apr. 27, 2020.

(51) Int. Cl.
*A61K 9/00* (2006.01)
*A61K 31/573* (2006.01)
*A61K 49/00* (2006.01)

(52) U.S. Cl.
CPC .......... *A61K 9/0051* (2013.01); *A61K 31/573* (2013.01); *A61K 49/0043* (2013.01)

(58) Field of Classification Search
CPC .......................... A61K 9/0048; A61K 9/0051
See application file for complete search history.

(56) References Cited

U.S. PATENT DOCUMENTS

| | | |
|---|---|---|
| 3,949,750 A | 4/1976 | Freeman |
| 3,993,071 A | 11/1976 | Higuchi et al. |
| 5,469,867 A | 11/1995 | Schmitt |
| 5,902,598 A | 5/1999 | Chen et al. |
| 6,196,993 B1 | 3/2001 | Cohan et al. |
| 6,437,152 B1 | 8/2002 | Jackson et al. |
| 6,509,327 B1 | 1/2003 | Cagle et al. |
| 6,646,001 B2 | 11/2003 | Hellberg et al. |
| 6,982,090 B2 | 6/2006 | Gillespie |
| 7,109,371 B2 | 9/2006 | Clissold et al. |
| 7,166,730 B2 | 1/2007 | Nisnevich et al. |
| 7,897,795 B2 | 3/2011 | Henschke et al. |
| 7,998,497 B2 | 8/2011 | de Juan, Jr. et al. |
| 8,080,593 B2 | 12/2011 | Humayun et al. |
| 8,178,582 B2 | 5/2012 | Kabra |
| 8,268,299 B2 | 9/2012 | Kabra et al. |
| 8,323,630 B2 | 12/2012 | Kabra et al. |
| 8,388,941 B2 | 3/2013 | Chowhan et al. |
| 8,409,606 B2 | 4/2013 | Sawhney et al. |
| 8,436,194 B2 | 5/2013 | Henschke et al. |
| 8,476,471 B2 | 7/2013 | Yiannikouros et al. |
| 8,512,749 B2 | 8/2013 | Edelman et al. |
| 8,535,705 B2 | 9/2013 | Edelman et al. |
| 8,563,027 B2 | 10/2013 | Sawhney et al. |
| 8,691,265 B2 | 4/2014 | de Juan et al. |
| 8,715,712 B2 | 5/2014 | de Juan et al. |
| 8,722,735 B2 | 5/2014 | Kabra et al. |
| 8,742,143 B2 | 6/2014 | Henschke et al. |
| 8,747,884 B2 | 6/2014 | de Juan et al. |
| 8,754,123 B2 | 6/2014 | Kabra |
| 8,846,073 B2 | 9/2014 | Spada et al. |
| 8,900,662 B2 | 12/2014 | Lee et al. |
| 8,901,319 B2 | 12/2014 | Chambournier et al. |
| 8,957,240 B2 | 2/2015 | Hogan et al. |
| 8,961,501 B2 | 2/2015 | Jarrett et al. |
| 9,061,065 B2 | 6/2015 | Robinson et al. |
| 9,115,109 B2 | 8/2015 | Wei et al. |
| 9,125,807 B2 | 9/2015 | Sawhney et al. |
| 9,126,898 B2 | 9/2015 | Oh et al. |
| 9,144,561 B2 | 9/2015 | Kabra |
| 9,149,428 B2 | 10/2015 | Spada et al. |
| 9,168,222 B2 | 10/2015 | de Juan et al. |
| 9,187,593 B2 | 11/2015 | Dadey et al. |
| 9,205,150 B2 | 12/2015 | El-Hayek et al. |
| 9,212,125 B2 | 12/2015 | Kardos et al. |
| 9,254,267 B2 | 2/2016 | Sawhney |
| 9,290,432 B2 | 3/2016 | Bischof et al. |
| 9,370,485 B2 | 6/2016 | Sawhney et al. |
| 9,393,223 B2 | 7/2016 | Hughes |
| 9,421,126 B2 | 8/2016 | Alster et al. |

(Continued)

FOREIGN PATENT DOCUMENTS

| | | | | |
|---|---|---|---|---|
| CA | 3038075 A1 * | 3/2018 | .......... | A61F 9/0017 |
| KR | 20070121537 A | 12/2007 | | |

(Continued)

OTHER PUBLICATIONS

Brooks et al (Dexamethasone 0.4mg Sustained-Release Intracanalicular Insert in the Management of Ocular Inflammation and Pain Following Ophthalmic Surgery: Design, Development and Place in Therapy; Clinical Ophthalmology 2020: 14 89-94) (Year: 2020).*
Torkildsen et al (Vehicle-Controlled, Phase 2 Clinical Trial of Sustained-Release Dexamethasone Intracanalicular Insert in a Chronic Allergen Challenge Model; Journal of Ocular Pharmacology and therapeutics, vol. 33, No. 2, 2017, p. 79-90). (Year: 2017).*
Brooks et al (Dexamethasone 0.4 Sustained-Release Intracanalicular Insert in the Management of Ocular Inflammation and Pain Following Opthalmic Surgery: Design, Development and Place in Therapy; Clinical Ophthalmology 2020: 14, 89-94) (Year: 2020).*
Maturi et al (Intraocular Pressure in Patients with Diabetic Macular Edema Treated with Dexamethasone Intravitreal Implant in the 3-Year Mead Study; Retina, 36:1143-1152, 2016 hereafter Maturi (Year: 2016).*

(Continued)

*Primary Examiner* — Micah Paul Young
(74) *Attorney, Agent, or Firm* — Lowenstein Sandler LLP

(57) ABSTRACT

Disclosed is a sustained release biodegradable intracanalicular insert containing a glucocorticoid dispersed in a hydrogel. The insert is administered to a subject for the treatment of allergic conjunctivitis.

8 Claims, 11 Drawing Sheets

(56) References Cited

U.S. PATENT DOCUMENTS

| | | | |
|---|---|---|---|
| 9,445,944 B2 | 9/2016 | Rapacki et al. |
| 9,463,114 B2 | 10/2016 | Odrich et al. |
| 9,464,028 B2 | 10/2016 | Wei et al. |
| 9,504,696 B2 | 11/2016 | Robinson et al. |
| 9,540,311 B2 | 1/2017 | Wei et al. |
| 9,549,852 B2 | 1/2017 | de Juan et al. |
| 9,555,045 B2 | 1/2017 | Garrigue et al. |
| 9,561,282 B2 | 2/2017 | Dadey et al. |
| 9,707,173 B2 | 7/2017 | Kabra |
| 9,707,238 B2 | 7/2017 | Chang et al. |
| 9,750,636 B2 | 9/2017 | Rubin et al. |
| 9,775,906 B2 | 10/2017 | Sawhney et al. |
| 9,828,356 B2 | 11/2017 | Wei et al. |
| 9,849,082 B2 | 12/2017 | de Juan, Jr. et al. |
| 9,937,073 B2 | 4/2018 | de Juan et al. |
| 9,949,942 B2 | 4/2018 | Butuner |
| 10,004,636 B2 | 6/2018 | Alster et al. |
| 10,064,872 B2 | 9/2018 | Chang et al. |
| 10,100,028 B2 | 10/2018 | Mannikouros et al. |
| 10,226,417 B2 | 3/2019 | Jarrett et al. |
| 10,245,178 B1 | 4/2019 | Heitzmann et al. |
| 10,251,954 B2 | 4/2019 | Sawhney et al. |
| 10,278,919 B2 | 5/2019 | Robinson et al. |
| 10,300,014 B2 | 5/2019 | de Juan, Jr. et al. |
| 10,383,817 B2 | 8/2019 | de Juan et al. |
| 10,420,724 B2 | 9/2019 | Jarrett et al. |
| 10,434,009 B2 | 10/2019 | Rapacki et al. |
| 10,441,543 B2 | 10/2019 | Spada et al. |
| 10,456,293 B2 | 10/2019 | Rubin et al. |
| 10,617,563 B2 | 4/2020 | Jarrett et al. |
| 10,736,774 B2 | 8/2020 | Alster et al. |
| 10,744,099 B2 | 8/2020 | Ibin et al. |
| 10,786,462 B2 | 9/2020 | Jarrett et al. |
| 10,835,416 B2 | 11/2020 | de Juan et al. |
| 10,849,656 B2 | 12/2020 | Navratil et al. |
| 10,864,218 B2 | 12/2020 | Hughes |
| 10,874,606 B2 | 12/2020 | de Juan, Jr. et al. |
| 10,905,765 B2 | 2/2021 | Jarrett et al. |
| 2002/0169409 A1 | 11/2002 | Gillespie |
| 2003/0108511 A1 | 6/2003 | Sawhney |
| 2004/0175410 A1 | 9/2004 | Ashton et al. |
| 2005/0197614 A1 | 9/2005 | Pritchard et al. |
| 2008/0124400 A1 | 5/2008 | Liggins et al. |
| 2008/0247984 A1 | 10/2008 | Messersmith et al. |
| 2009/0227981 A1 | 9/2009 | Bennett |
| 2010/0209478 A1 | 8/2010 | Sawhney et al. |
| 2010/0278898 A1 | 11/2010 | Hughes et al. |
| 2013/0172268 A1 | 7/2013 | Jarrett et al. |
| 2014/0121612 A1 | 5/2014 | Rubin et al. |
| 2014/0128478 A1 | 5/2014 | Asgharian et al. |
| 2014/0371308 A1 | 12/2014 | Hughes |
| 2015/0272898 A1 | 10/2015 | Hughes et al. |
| 2015/0374633 A1 | 12/2015 | Fedorchak et al. |
| 2016/0106587 A1* | 4/2016 | Jarrett ................. A61M 5/19 514/180 |
| 2016/0166504 A1* | 6/2016 | Jarrett ................. A61K 9/50 424/490 |
| 2016/0243291 A1 | 8/2016 | Reich et al. |
| 2016/0296627 A1 | 10/2016 | Garcia et al. |
| 2016/0354309 A1 | 12/2016 | Heitzmann et al. |
| 2017/0037002 A1 | 2/2017 | Vajda et al. |
| 2017/0073323 A1 | 3/2017 | Wei et al. |
| 2017/0304194 A1 | 10/2017 | Utkhede et al. |
| 2018/0085307 A1 | 3/2018 | Sawhney et al. |
| 2018/0094099 A1 | 4/2018 | Johnson et al. |
| 2018/0289543 A1 | 10/2018 | Silverberg et al. |
| 2019/0021991 A9 | 1/2019 | Heitzmann et al. |
| 2019/0038636 A1 | 2/2019 | Vrabec |
| 2019/0216727 A1 | 7/2019 | Odrich et al. |
| 2019/0224046 A1 | 7/2019 | Heitzmann et al. |
| 2020/0038326 A1 | 2/2020 | Spada et al. |
| 2020/0138701 A9 | 5/2020 | Odrich et al. |
| 2020/0246222 A1 | 8/2020 | Malanga et al. |
| 2020/0345544 A1 | 11/2020 | Ketelson et al. |
| 2020/0345750 A1 | 11/2020 | Chang et al. |
| 2020/0383915 A1 | 12/2020 | Jablonski et al. |

FOREIGN PATENT DOCUMENTS

| | | |
|---|---|---|
| WO | 2006031658 A2 | 3/2006 |
| WO | 2009/008946 | 1/2009 |
| WO | 2009105178 A2 | 8/2009 |
| WO | 2010/093873 | 8/2010 |
| WO | 2010111449 A1 | 9/2010 |
| WO | 2013/086015 | 6/2013 |
| WO | 2016037169 A1 | 3/2016 |
| WO | 2016/094646 | 6/2016 |
| WO | 2016/183296 | 11/2016 |
| WO | 2017/015591 | 1/2017 |
| WO | 2017/091749 | 6/2017 |
| WO | 2018/058048 | 3/2018 |

OTHER PUBLICATIONS

Walter et al (Efficacy and Safety of Sustained Release Dexamethasone for the Treatment of Ocular Pain and Inflammation after Cataract Surgery: Results from Two Phase 3 Studies; J Clin Exp Opthalmol, vol. 7, Issue 4, 2016, 572) (Year: 2016).*
https://doi.org/10.2147/OPTH.S238756 (Year: 2020).*
Torkilsden et al (Vehicle-Controlled, Phase 2, Clinical Trail of Sustained-Release Dexamethasone Intracanalicular Insert in a Chronic Allergen Challenge Model; Journal of Ocular Pharmacology and Therapeutics, vol. 33, No. 2, 2017, p. 79-90 (Year: 2017).*
International Search Report and Written Opinion of International Application No. PCT/US21/29184 mailed Jul. 21, 2021, 8 pgs.
Tyson, et al., "Punctum and canalicular anatomy for hydrogel-based intracanlicular insert technology", Therapeutic Delviery, Mar. 1, 2020, pp. 173-182, vol. 11, No. 3.
"Center for Drug Evaluation and Research; Dextenza (dexamethasone opthalmic insert) 0.4 mg, for Intracanalicular use", Jan. 1, 2018, 11 pgs.
Brooks, et al., "Dexamethasone 0.4mg Sustained-Release Intracanalicular Insert in the Management of Ocular Inflammationa nd Pain Following Opthalmic Surgery: Design, Development and Place in Therapy", Clinical Ophthalmology, Jan. 1, 2020, pp. 89-94, vol. 14.
U.S. Appl. No. 60/550,132, filed Mar. 4, 2004.
U.S. Appl. No. 60/557,368, filed Mar. 29, 2004.
U.S. Appl. No. 60/564,858, filed Apr. 23, 2004.
U.S. Appl. No. 60/637,569, filed Dec. 20, 2004.
Pardo-Lopez et al., "Anterior chamber migration of dexametasona intravitreal implant (Ozurdex)", Graefe's Archive for Clinical and Experimental Opthalmology, Nov. 2011, vol. 250, pp. 1703-1704, Published by Springer.
Gillies et al., "A Randomized Clinical Trial of Intravitreal Bevacizumab versus Intravitreal Dexamethasone for Diabetic Macular Edema", American Academy of Opthamology, 2014, pp. 2473-2481, Published by Elsevier Inc.
DEXTENZA Full Prescribing Information, Oct. 2021, 5 pgs.

* cited by examiner

A
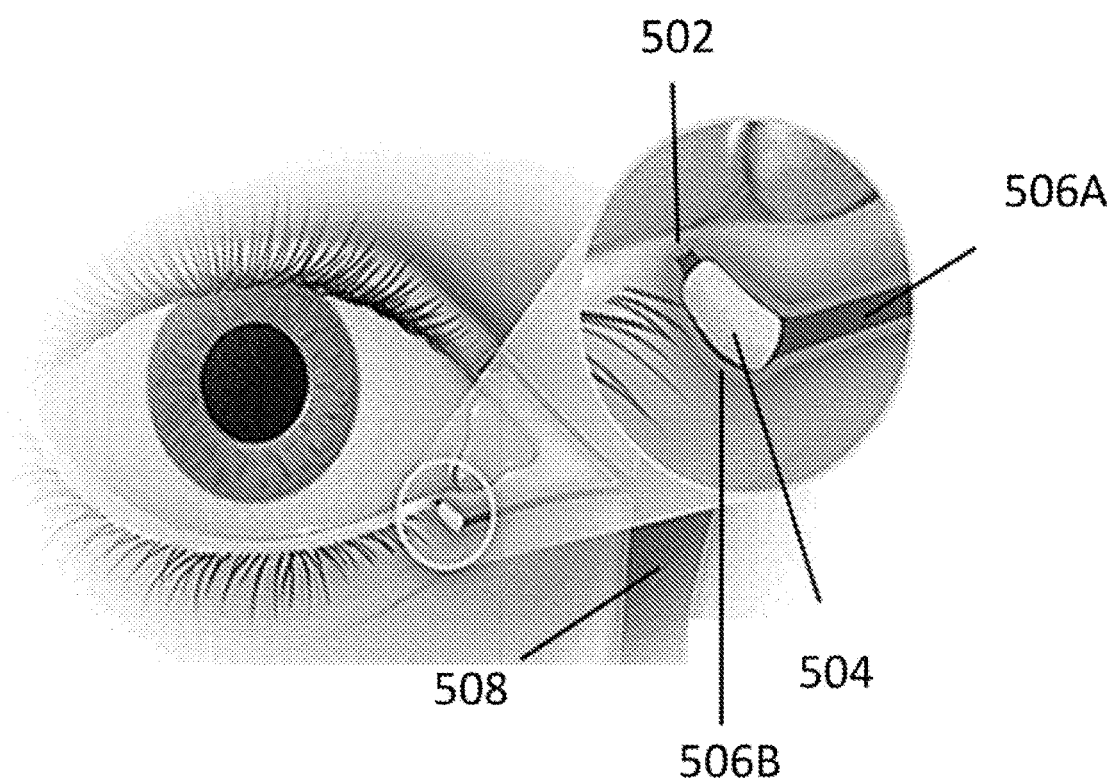
B
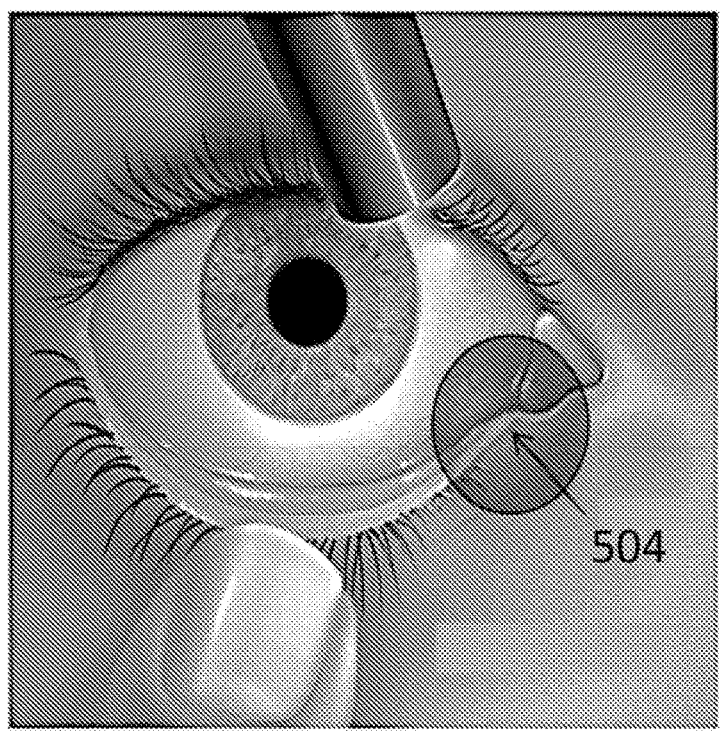
FIG. 5

METHODS OF TREATING ALLERGIC CONJUNCTIVITIS

CROSS-REFERENCE TO RELATED APPLICATION(S)

This application is a continuation of International Application No. PCT/US2021/02918 filed on Apr. 26, 2021, which claims the benefit of United States Provisional Patent Applicati No. 63/128,565, filed on Dec. 21, 2020 and U.S. Provisional Patent Application No. 63/016,030, filed on Apr. 27, 2020 and U.S. Provisional Patent Application No. 63/173,660 filed on Apr. 12, 2021. The contents of these applications are hereby incorporated by reference in their entirety.

FIELD OF THE INVENTION

Technical Field

The present invention relates to the treatment of allergic conjunctivitis, and in certain embodiments to the treatment of ocular itching and/or ocular redness associated with allergic conjunctivitis. According to one or more embodiments, allergic conjunctivitis is treated by administering a biodegradable insert into the superior and/or inferior canaliculus of the eye, wherein the insert provides sustained release of a glucocorticoid such as dexamethasone.

BACKGROUND

Allergic conjunctivitis (AC), often referred to as ocular allergy, represents one of the most common conditions encountered by allergists and ophthalmologists (Ital J Pediatr. 2013; 39: 18). Research shows that allergic conjunctivitis affects approximately 40% of the North American population and is increasing in prevalence. See Curr Opin Allergy Clin Immunol. 2011; 11(5):471-6 and J Allergy Clin Immunol. 2010; 126(4):778-83. The most common treatment options for allergic conjunctivitis include topical ophthalmic formulations intended to reduce inflammation and provide symptomatic relief. The problem with this approach is that most medications require multiple daily dosage. This can be inconvenient and may reduce treatment compliance. In addition, the more readily available formulations are in the form of eye drops which increase the potential for inconsistent dosing and drug abuse. Patients who experience moderate symptoms may also require more effective and longer-lasting treatment than the current standard of care. A need, therefore, remains for alternative therapeutics for treating allergic conjunctivitis and related conditions. In view of the drawbacks and challenges experienced with current available treatments, novel treatment methods that effectively deliver glucocorticoids, that are effective over a period of one or more weeks and avoid the need for daily glucocorticoid administrations, would be beneficial to patients.

OBJECTS AND SUMMARY OF THE INVENTION

It is an object of certain embodiments of the present invention to provide a method of treating allergic conjunctivitis in a patient in need thereof, the method comprising administering to the patient in need thereof an ocular insert comprising a glucocorticoid such as dexamethasone.

It is an object of certain embodiments of the present invention to provide a method of treating allergic conjunctivitis in a patient in need thereof, the method comprising administering to the patient in need thereof a sustained release biodegradable intracanalicular insert comprising a hydrogel and a glucocorticoid such as dexamethasone.

It is an object of certain embodiments of the present invention to provide a method of treating ocular itching associated with allergic conjunctivitis in a patient in need thereof, the method comprising administering to the patient in need thereof an ocular insert comprising a glucocorticoid such as dexamethasone It is an object of certain embodiments of the present invention to provide a method of treating ocular itching associated with allergic conjunctivitis in a patient in need thereof, the method comprising administering to the patient in need thereof a sustained release biodegradable intracanalicular insert comprising a hydrogel and a glucocorticoid such as dexamethasone.

It is an object of certain embodiments of the present invention to provide a method of treating conjunctival redness associated with allergic conjunctivitis in a patient in need thereof, the method comprising administering to the patient in need thereof an ocular insert comprising a glucocorticoid such as dexamethasone.

It is an object of certain embodiments of the present invention to provide a method of treating conjunctival redness associated with allergic conjunctivitis in a patient in need thereof, the method comprising administering to the patient in need thereof a sustained release biodegradable intracanalicular insert comprising a hydrogel and a glucocorticoid such as dexamethasone.

It is another object of certain embodiments to provide an insert as disclosed herein for the methods disclosed herein.

One or more of these objects of the present invention and others are solved by one or more embodiments of the invention as disclosed and claimed herein.

The individual aspects of the present invention are disclosed in the specification and claimed in the independent claims, while the dependent claims recite particular embodiments and variations of these aspects of the invention. Details of the various aspects of the present invention are provided in the detailed description below.

BRIEF DESCRIPTION OF THE DRAWINGS

FIG. 5 shows a schematic exemplary representation of insert placement into the inferior vertical canaliculus through the lower punctum of the eye (A). Visualization of the insert is possible by illumination with blue light (B). The fluorescein in the intracanalicular insert illuminates when excited with blue light enabling confirmation of insert presence in a non-invasive manner.

DEFINITIONS

Figure 1:
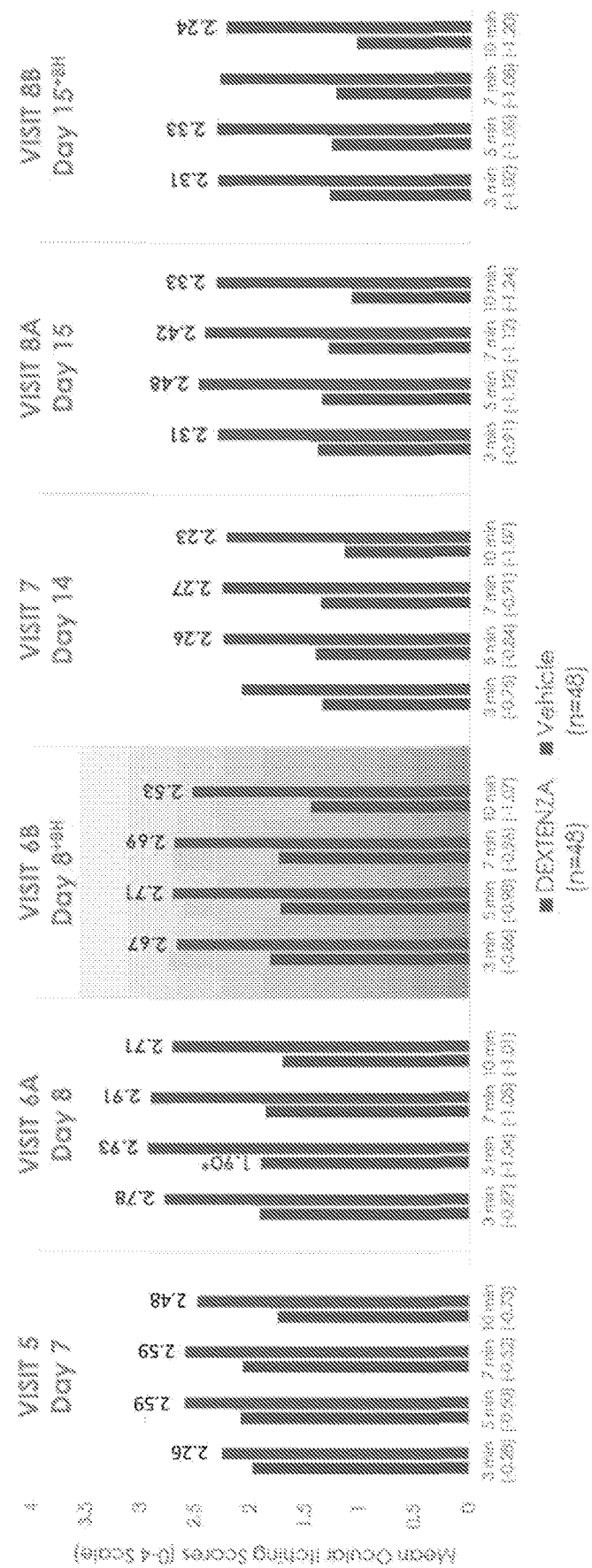
FIG. 1 shows the mean ocular itching scores for studies using Dextenza®.

The term "insert" as used herein refers to an object that contains an active agent, specifically a glucocorticoid, such as dexamethasone, that is administered into the human or animal body, such as to the canaliculus of the eye, where it remains for a certain period of time while it releases the active agent into the surrounding environment. An insert can be any predetermined shape before being inserted, which general shape may be maintained to a certain degree upon placing the insert into the desired location, although dimensions of the insert (e.g. length and/or diameter) may change after administration due to hydration as further disclosed herein. In other words, what is administered into the canaliculus of the eye is not a solution or suspension, but an already shaped, coherent object. The insert has thus been completely formed, e.g., according to the methods disclosed herein prior to being administered. Over the course of time the insert in certain embodiments is biodegraded (as disclosed herein), and may thereby change its shape (e.g. may expand in diameter and decrease in length) until it has been completely dissolved/resorbed. Herein, the term "insert" is used to refer both to an insert in a hydrated (also referred to herein as "wet") state when it contains water, e.g. after the insert has been hydrated or (re-)hydrated once administered to the eye or otherwise immersed into an aqueous environment, and to an insert in its/a dry (dried/dehydrated) state.

Dextenza® (a dexamethasone ophthalmic insert) is an FDA-approved corticosteroid indicated for the treatment of ocular inflammation and pain following ophthalmic surgery. Dextenza® is inserted in the lower lacrimal punctum and into the canaliculus, and releases 0.4 mg of dexamethasone for up to 30-day following insertion. Dextenza®. Dextenza® is resorbable and does not require removal.

The term "ocular" as used herein refers to the eye in general, or any part or portion of the eye (as an "ocular insert" according to the invention refers to an insert that can in principle be administered to any part or portion of the eye). The present invention in certain embodiments is directed to intracanalicular administration of an ocular insert, and to the treatment of allergic conjunctivitis, as further disclosed herein.

The term "biodegradable" as used herein refers to a material or object (such as the intracanalicular insert according to the present invention) which becomes degraded in vivo, i.e., when placed in the human or animal body. In the context of the present invention, as disclosed in detail herein, the insert comprising the hydrogel within which particles of a glucocorticoid, such as particles of dexamethasone, are dispersed, slowly biodegrades over time once deposited within the eye, e.g., within the canaliculus. In certain embodiments, biodegradation takes place at least in part via ester hydrolysis in the aqueous environment provided by the tear fluid. In certain embodiments, the intracanalicular inserts of the present invention slowly soften and liquefy, and are eventually cleared (disposed/washed out) through the nasolacrimal duct.

A "hydrogel" is a three-dimensional network of one or more hydrophilic natural or synthetic polymers (as disclosed herein) that can swell in water and hold an amount of water while maintaining or substantially maintaining its structure, e.g., due to chemical or physical cross-linking of individual polymer chains. Due to their high water content, hydrogels are soft and flexible, which makes them very similar to natural tissue. In the present invention the term "hydrogel" is used to refer both to a hydrogel in the hydrated state when it contains water (e.g. after the hydrogel has been formed in an aqueous solution, or after the hydrogel has been hydrated or (re-)hydrated once inserted into the eye or otherwise immersed into an aqueous environment) and to a hydrogel in its/a dry (dried/dehydrated) state when it has been dried to a low water content of e.g. not more than 1% by weight. In the present invention, wherein an active principle is contained (e.g. dispersed) in a hydrogel, the hydrogel may also be referred to as a "matrix".

The term "polymer network" as used herein describes a structure formed of polymer chains (of the same or different molecular structure and of the same or different average molecular weight) that are cross-linked with each other. Types of polymers suitable for the purposes of the present invention are disclosed herein. The polymer network may be formed with the aid of a crosslinking agent as also disclosed herein.

The term "amorphous" refers to a polymer or polymer network which does not exhibit crystalline structures in X-ray or electron scattering experiments.

The term "semi-crystalline" refers to a polymer or polymer network which possesses some crystalline character, i.e., exhibits some crystalline properties in X-ray or electron scattering experiments.

The term "precursor" or "polymer precursor" herein refers to those molecules or compounds that are reacted with each other and that are thus connected via crosslinks to form a polymer network and thus the hydrogel matrix. While other materials might be present in the hydrogel, such as active agents, visualization agents or buffers, they are not referred to as "precursors".

The molecular weight of a polymer precursor as used for the purposes of the present invention and as disclosed herein may be determined by analytical methods known in the art. The molecular weight of polyethylene glycol can for example be determined by any method known in the art, including gel electrophoresis such as SDS-PAGE (sodium dodecyl sulphate-polyacrylamide gel electrophoresis), gel permeation chromatography (GPC), including GPC with dynamic light scattering (DLS), liquid chromatography (LC), as well as mass spectrometry such as matrix-assisted laser desorption/ionization-time of flight (MALDI-TOF) spectrometry or electrospray ionization (ESI) mass spectrometry. The molecular weight of a polymer, including a polyethylene glycol precursor as disclosed herein, is an average molecular weight (based on the polymer's molecular weight distribution), and may therefore be indicated by means of various average values, including the weight average molecular weight (Mw) and the number average molecular weight (Mn). Any of such average values may be used in the context of the present invention. In certain embodiments, the average molecular weight of the polyethylene glycol units or other precursors as disclosed herein is the number average molecular weight.

The parts of the precursor molecules that are still present in a final polymer network are also called "units" herein. The "units" are thus the building blocks or constituents of a polymer network forming the hydrogel. For example, a polymer network suitable for use in the present invention may contain identical or different polyethylene glycol units as further disclosed herein.

As used herein, the term "crosslinking agent" refers to any molecule that is suitable for connecting precursors via crosslinks to form the polymer network and thus the hydrogel matrix. In certain embodiments, crosslinking agents may be low-molecular weight compounds or may be polymeric compounds as disclosed herein.

The term "sustained release" is defined for the purposes of the present invention to refer to pharmaceutical dosage forms which are formulated to make a glucocorticoid such as dexamethasone available over an extended period of time after administration, such as one or more weeks, thereby allowing a reduction in dosing frequency compared to an immediate release dosage form, e.g. a solution of a glucocorticoid that is topically applied onto the eye (i.e. glucocorticoid-comprising eye drops). Other terms that may be used herein interchangeably with "sustained release" are "extended release" or "controlled release". Within the meaning of the invention, the term "sustained release" also comprises a period of constant glucocorticoid release per day, followed by a period of tapered glucocorticoid release. In other words, during a "sustained release" period, the release rate is not necessarily constant or essentially constant, but may change over time. Within the meaning of the invention, the term "tapered" or "tapering" refers to a decreasing release of glucocorticoid such as dexamethasone over time until the glucocorticoid is completely released.

The term "visualization agent" as used herein refers to a molecule or composition that may be contained within an insert of the present invention and that provides the possibility of easily visualizing the insert in a non-invasive manner when it is located in the canaliculus of the eye, e.g. by illuminating the corresponding eye parts with a suitable light source. The visualization agent may be a fluorophore such as fluorescein, rhodamine, coumarin, and cyanine. In certain embodiments the visualization agent is fluorescein or includes a fluorescein moiety.

As used herein, the term "ocular surface" comprises the conjunctiva and/or the cornea, together with elements such as the lacrimal apparatus, including the lacrimal punctum, as well as the lacrimal canaliculus and associated eyelid structures. Within the meaning of this invention, the ocular surface encompasses also the aqueous humor.

As used herein, the terms "tear fluid" or "tears" or "tear film" refer to the liquid secreted by the lacrimal glands, which lubricates the eyes. Tears are made up of water, electrolytes, proteins, lipids, and mucins.

As used herein, the term "bilaterally" or "bilateral" refers (in the context of administration of the inserts of the present invention) to an administration of the inserts into both eyes of a patient. "Unilaterally" or "unilateral" thus refers to an administration of the insert into one eye only. The inserts may be independently inserted into the superior and/or the inferior canaliculus of both eyes or of one eye.

As used herein, the terms "administration" or "administering" or "administered" etc. in the context of the inserts of the present invention refer to the process of insertion of the inserts into an area of the eye, e.g., through the opening of the punctum into the canaliculus of the eye. Thus, "administering an insert" or similar terms refer to the insertion of the insert into e.g., the canaliculus. The terms "insertion" or "inserting" or "inserted" etc. in the context of the inserts of the present invention equally refer to the process of insertion of the inserts, e.g., through the opening of the punctum into the canaliculus of the eye and are thus herein used interchangeably with the terms "administration" or "administering" or "administered". In contrast, the terms "administration" or "administering" or "administered" etc. in the context of topical ophthalmic pharmacological products such as eye drops (which are not the subject of the present invention) refer to topical application of these products onto the eye.

As used herein, the term "insert stacking" or "stacking" refers to the insertion of a further insert on top of a first insert while the first insert is still retained, e.g., in the canaliculus. In certain embodiments, the further insert is placed on top of the first insert after the glucocorticoid contained in the first insert is completely or essentially completely released, or after at least about 70% or at least about 80% or at least about 90% of the glucocorticoid contained in the first insert has been released. Insert stacking enables, for instance, prolonged glucocorticoid treatment.

The term "plug" as used herein refers to a device capable of providing an occlusion, substantial occlusion or partial occlusion of the tear duct(s) ("lacrimal occlusion") thereby minimizing or preventing draining of tears. A plug thus increases tear retention, which helps to keep the eyes moist. Plugs can be classified into "punctal plugs" and "intracanalicular plugs". Intracanalicular plugs are also referred to as "canalicular plugs" in literature. Both plug classes are inserted through the upper and/or lower punctum of the eye. Punctal plugs rest at the punctal opening making them easily visible and, hence, removable without much difficulty. However, punctal plugs may show poor retention rates and can be more easily contaminated with microbes due to their exposed localization resulting in infection. In contrast, intracanalicular plugs are essentially not visible and provide a better retention rate compared to punctal plugs as they are placed inside either the vertical or the horizontal canaliculus. However, currently available intracanalicular plugs may not be easy to remove and/or may provide an increased risk of migration due to loose fit. Commercially available plugs are often made of collagen, acrylic polymers, or silicone.

The terms "canaliculus" (plural "canaliculi") or alternatively "tear duct" as used herein refer to the lacrimal canaliculus (see 506A, 506B of FIG. 5), i.e. the small channels in each eyelid that drain lacrimal fluid (tear fluid) from the lacrimal punctum (see 502) to the nasolacrimal duct (see 508). Canaliculi therefore form part of the lacrimal apparatus that drains lacrimal fluid from the ocular surface to the nasal cavity. The canaliculus in the upper eyelid is referred to as "superior canaliculus" or "upper canaliculus", whereas the canaliculus in the lower eyelid is referred to as "inferior canaliculus" or "lower canaliculus". Each canaliculus comprises a vertical region, referred to as "vertical canaliculus" following the lacrimal punctum and a horizontal region, referred to as "horizontal canaliculus" following the vertical canaliculus, wherein the horizontal canaliculus merges into the nasolacrimal duct.

The term "punctum" (plural "puncta") refers to the lacrimal punctum, an opening on the margins of the eyelids, representing the entrance to the canaliculus. After tears are produced, some fluid evaporates between blinks, and some is drained through the lacrimal punctum. As both the upper and the lower eyelids show the lacrimal punctum, the puncta are therefore referred to as "upper punctum" or "superior punctum" and "lower punctum" or "inferior punctum", respectively (see also FIG. 5).

The term "intracanalicular insert" refers to an insert that can be administered through the upper and/or lower punctum into the superior and/or inferior canaliculus of the eye, in particular into the superior and/or inferior vertical canaliculus of the eye. Due to the intracanalicular localization of the insert, the insert blocks tear drainage through lacrimal occlusion such as also observed for intracanalicular plugs. The intracanalicular inserts of the present invention may be inserted bilaterally or unilaterally into the inferior and/or superior vertical canaliculi of the eyes. According to certain embodiments of the present invention, the intracanalicular insert is a sustained release biodegradable insert.

The terms "API", "active (pharmaceutical) ingredient", "active (pharmaceutical) agent", "active (pharmaceutical) principle", "(active) therapeutic agent", "active", and "drug" are used interchangeably herein and refer to the substance used in a finished pharmaceutical product (FPP) as well as the substance used in the preparation of such a finished pharmaceutical product, intended to furnish pharmacological activity or to otherwise have direct effect in the diagnosis, cure, mitigation, treatment or prevention of a disease, or to have direct effect in restoring, correcting or modifying physiological functions in a patient.

The API used according to the present invention is a glucocorticoid such as dexamethasone. Glucocorticoids are a class of corticosteroids, which are a class of steroid hormones. The name "glucocorticoid" is a portmanteau (glucose+cortex+steroid) and is composed from its role in regulation of glucose metabolism, synthesis in the adrenal cortex, and its steroidal structure. A less common synonym is glucocorticosteroid. Glucocorticoids act through glucocorticoid receptor-mediated pathways present in most cells in the body to regulate gene expression, and through non-receptor pathways to inhibit inflammatory cytokine (TNF alpha, IL-1a, and IL-6) and chemokine production and decrease the synthesis of matrix metalloproteinases (Rosenbaum et al., 1980; Nature 286(5773): 611-613). Glucocorticoids, such as dexamethasone, suppress inflammation by inhibiting edema, fibrin deposition, capillary deposition, and phagocytic migration of the inflammatory response (Chrousos 1995, NEJM 332(20): 1351-1362; Abelson et al. 2002, Review of Ophthalmology: 110-114; Sherif and Pleyer 2002, Ophthalmologica 216(5): 305-315). As in other tissues, glucocorticoids do not appear to have a specific mechanism of action in ocular tissues but exert a broad spectrum of anti-inflammatory activity (Leopold 1985, M. L. Sears and A. Tarkkanen, ed. New York, Raven Press: 83-133; Kaiya 1990, J Cataract Refract Surg 16 (3): 320-324). In general, most uses of glucocorticoids are limited to a relatively short duration (about 2 to 3 weeks), due to concerns regarding potential side effects associated with prolonged use. Cortisol (or the synthetic form, referred to as hydrocortisone) is the most important human glucocorticoid. In addition, a variety of synthetic glucocorticoids with varying potencies has been created for therapeutic use. Examples of synthetic glucocorticoids are prednisone, prednisolone, prednisolone acetate, methylprednisolone, dexamethasone, dexamethasone acetate, betamethasone, betamethasone sodium phosphate, budesonide, flunisolide, fluticasone propionate, triamcinolone, triamcinolone acetonide, triamcinolone hexacetonide, triamcinolone diacetate, fluocinolone acetonide, fludrocortisone acetate, loteprednol, loteprednol etabonate, difluprednate, fluorometholone, mometasone foroate, deoxycorticosterone acetate, aldosterone, rimexolone, beclometasone, and beclomethasone dipropionate. Any of these synthetic glucocorticoids are suitable for use in the present invention. In particular embodiments of the invention the glucocorticoid is a low solubility glucocorticoid (i.e., having a solubility in water of less than about 100 μg/mL), including (but not limited to) beclomethasone dipropionate, betamethasone sodium phosphate, budesonide, flunisolide, fluticasone propionate, triamcinolone acetonide, triamcinolone hexacetonide, triamcinolone diacetate, dexamethasone, dexamethasone acetate, prednisolone acetate, loteprednol etabonate, difluprednate, fluorometholone, fluocinolone acetonide, and mometasone furoate. Dexamethasone is sometimes also referred to as "dexamethasone alcohol".

In general, glucocorticoid potencies are reported as relative potencies in view of cortisol potency. Determination of equivalent glucocorticoid doses is well established in the art. Equivalent oral doses and relative oral glucocorticoid potencies are presented in Table 1 for exemplarily selected glucocorticoids (see for instance, Buttgereit et al. 2002, Ann Rheum Dis 61:718-722, which is incorporated herein by reference).

TABLE 1

Established equivalent oral doses and relative oral glucocorticoid potencies (with reference to cortisol) of exemplarily selected glucocorticoids.

| Glucocorticoid | Relative Potency | Equivalent Dose | Glucocorticoid | Relative Potency | Equivalent Dose |
| --- | --- | --- | --- | --- | --- |
| Cortisol (Hydrocortisone) | 1 | 20 mg | Dexamethasone | 25-80 | 0.8 mg |
| Prednisone | 3.5-5 | 5 mg | Betamethasone | 25-30 | 0.8 mg |
| Prednisolone | 4 | 5 mg | Triamcinolone | 5 | 4 mg |
| Methylprednisolone | 5-7.5 | 4 mg | | | |

As used herein, the term "equivalent dose" refers to a dose of an active such as a glucocorticoid that is equivalent in terms of biological activity to a dose of another active such as another glucocorticoid when delivered via the same administration route (e.g. oral, intravenous, topical, or via the intracanalicular inserts of the present application).

Examples for equivalent oral doses of glucocorticoids are presented in Table 1. For instance, upon oral administration of 20 mg hydrocortisone, similar biological effects are to be expected when compared to oral administration of 0.8 mg dexamethasone.

In certain embodiments, the glucocorticoid used according to the present invention is dexamethasone. Dexamethasone is a long-acting anti-inflammatory 9-fluoro glucocorticoid (also termed a glucocorticoid agonist) with a molecular weight of 392.47 g/mol. The molecular formula of dexamethasone is $C_{22}H_{29}FO_5$ and its IUPAC name is 9-Fluor-11β,17,21-trihydroxy-16α-methyl-pregna-1,4-dien-3,20-dion (CAS No. 50-02-2). The chemical structure of dexamethasone is reproduced below:

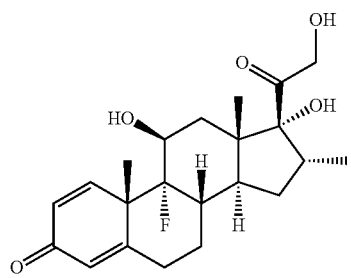

Dexamethasone is a white to practically white, odorless crystalline powder with poor solubility in water (approx. 89 mg/L at 25° C.). Its partition coefficient (n-octanol/water) is 1.83 (log P; cf. DrugBank entry "dexamethasone"). In certain embodiments of the present invention, dexamethasone is micronized and may have a D50 particle size of less than about 10 μm and/or a D99 particle size of less than about 50 μm. A specific suitable micronized dexamethasone for use in certain embodiments of the present invention is "Dexamethasone USP micronized" from Pfizer with a D90 particle size of equal to or less than about 5 μm (i.e., the volume portion of particles with a particle size of or below about 5 μm is 90%), and a D98 particle size of equal to or below about 10 μm (i.e., the volume portion of particles with a particle size of equal to or below about 10 μm is 98%). The "D" value such as in "D50" means that the indicated percentage by volume (such as 50 volume-% in D50 etc.) of all particles within the respective bulk material (which has a certain particle size distribution) has a particle size of or below the indicated value, e.g. a D50 particle size of below about 10 μm means that 50 volume-% of the particles have a particle size of or below about 10 μm. The particle size distribution can be commonly measured by methods known in the art, and includes sieving as well as laser diffraction methods. In embodiments in which another glucocorticoid than dexamethasone is used in the present invention similar particle sizes may apply as disclosed for dexamethasone. Generally speaking, for any glucocorticoid including dexamethasone, non-limiting particle sizes of about 100 μm or below, or of about 75 μm or below may be used, such as a particle size from about 20 μm to about 75 pin, or from about 20 μm to about 50 μm.

For the purposes of the present invention, active agents (including dexamethasone) in all their possible forms, including any active agent polymorphs or any pharmaceutically acceptable salts, anhydrates, hydrates, other solvates or derivatives of active agents, can be used. Whenever in this description or in the claims an active agent is referred to by name, e.g., "dexamethasone", even if not explicitly stated, it also refers to any such pharmaceutically acceptable polymorphs, salts, anhydrates, solvates (including hydrates) or derivatives of the active agent. Particularly, the term "dexamethasone" refers to dexamethasone and pharmaceutically acceptable salts thereof, which may all be used for the purposes of the present invention. In addition to dexamethasone (alcohol) itself, suitable solid forms of dexamethasone for use in the present invention include for example (without being limited to these) dexamethasone sodium phosphate, dexamethasone acetate, dexamethasone 21-(adamantane-1-carboxylate), dexamethasone isonicotinate, dexamethasone valerate, dexamethasone tebutate, dexamethasone 21-sulfobenzoate, dexamethasone palmitate, dexamethasone cipecilate, dexamethasone carboxamide, dexamethasone propionate as well as any mixtures thereof.

As used herein, the term "therapeutically effective" refers to the amount of drug or active agent (i.e. glucocorticoid) required to produce a desired therapeutic response or result after administration. For example, in the context of the present invention, one desired therapeutic result would be the reduction of symptoms associated with allergic conjunctivitis such as ocular itching and conjunctival redness.

The term "average" as used herein refers to a central or typical value in a set of data, which is calculated by dividing the sum of the values in the set by their number.

As used herein, the term "about" in connection with a measured quantity refers to the normal variations in that measured quantity, as expected by one of ordinary skill in the art in making the measurement and exercising a level of care commensurate with the objective of measurement and the precision of the measuring equipment.

As used herein, the term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that.

As used herein, the singular forms "a," "an", and "the" include plural references unless the context clearly indicates otherwise.

The term "and/or" as used in a phrase such as "A and/or B" herein is intended to include both "A and B" and "A or B".

Open terms such as "include," "including," "contain," "containing" and the like as used herein mean "comprising" and are intended to refer to open-ended lists or enumerations of elements, method steps, or the like and are thus not intended to be limited to the recited elements, method steps or the like but are intended to also include additional, unrecited elements, method steps or the like.

The term "up to" when used herein together with a certain value or number is meant to include the respective value or number. For example, the term "up to 25 days" means "up to and including 25 days".

As used herein, the singular forms "a," "an," and "the" include plural references unless the context clearly indicates otherwise. Thus, for example, reference to "a precursor" includes a single precursor as well as a mixture of two or more precursors; and reference to a "reactant" includes a single reactant as well as a mixture of two or more reactants, and the like.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or." When the term "about" or "approximately" is used herein, this is intended to mean that the nominal value presented is precise within +10%, such that "about 10" would include from 9 to 11.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that. In certain embodiments, the term "at least about" includes the recited number minus 10% and any quantity that is higher such that "at least about 10" would include 9 and anything greater than 9. This term can also be expressed as "about 10 or more." Similarly, the term "less than about" typically includes the recited number plus 10% and any quantity that is lower such that "less than about 10" would include 11 and anything less than 11. This term can also be expressed as "about 10 or less."

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

All references disclosed herein are hereby incorporated by reference in their entireties for all purposes (with the instant specification prevailing in case of conflict).

DETAILED DESCRIPTION

Allergic conjunctivitis (AC) is a prevalent, allergen-induced, inflammatory-mediated eye disorder that places a burden on patients and healthcare practices. Current topical drop therapies have limitations including potential for non-compliance, and preservatives toxicity. Although topical ophthalmic steroids are effective in treating allergic conjunctivitis, physicians report infrequent use due to side effects and risk of abuse associated with long-term use.

The FDA-approved dexamethasone ophthalmic insert DEXTENZA® is indicated for the treatment of ocular inflammation and pain following ophthalmic surgery. It has now been shown that intracanalicular inserts comprising a glucocorticoid and a hydrogel, effectively reduce ocular itching in subjects with allergic conjunctivitis. Disclosed herein are methods of treating allergic conjunctivitis in subjects with glucocorticoid ophthalmic inserts such as DEXTENZA®. For example, provided are methods of treating allergic conjunctivitis using biodegradable ocular hydrogel inserts comprising dexamethasone and a cross-linked polymer network having amides linkages formed from polyethylene glycol (PEG) activated esters and primary amines such as trilysine. DEXTENZA® is a physician-administered, hydrogel-based, intracanalicular insert designed to obviate the need for corticosteroid drops.

According to one or more embodiments, disclosed herein are methods of treating allergic conjunctivitis in a subject in need thereof. The methods include administering to the subject in need thereof, a therapeutically effective amount of a resorbable ophthalmic insert in the form of, for example, an ocular hydrogel insert. The insert includes dexamethasone and a cross-linked polymer network having amide linkages formed from trilysine and 4a20K PEG SG.

I. The Insert

In certain embodiments, the inserts utilized in the methods of the present invention relate to a sustained release biodegradable intracanalicular insert comprising a hydrogel and from about 0.3 mg to about 0.5 mg or about 0.4 mg of dexamethasone or an equivalent dose of another glucocorticoid.

In certain embodiments, the inserts utilized in the present invention relate to a sustained release biodegradable intracanalicular insert comprising a hydrogel and a glucocorticoid, wherein the insert in an unadministered or dry state has an average length of about 2.5 mm to about 3.5 mm or about 3 mm.

In certain embodiments, the inserts utilized in the present invention relate to a sustained release biodegradable intracanalicular insert comprising a hydrogel and a glucocorticoid, wherein the insert provides for a release of a therapeutically effective amount of the glucocorticoid for a period, e.g., greater than 25 days after administration.

In all these aspects, a particular glucocorticoid for use in the present invention is dexamethasone.

Specific embodiments and features of the insert utilized in the methods of the present invention are disclosed below.

The Active Principle:

The present invention in certain embodiments generally relates to a method of treating allergic conjunctivitis with a sustained release biodegradable intracanalicular insert comprising a hydrogel and a glucocorticoid. One particular glucocorticoid for use in all aspects of the present invention is dexamethasone. Details on dexamethasone, its chemical structure and its properties such as solubility are disclosed herein in the definitions section.

In one embodiment, the methods of the present invention utilize a sustained release biodegradable intracanalicular insert comprising a hydrogel and from about 0.3 mg to about 0.5 mg or about 0.4 mg of dexamethasone or an equivalent dose of another glucocorticoid.

If a glucocorticoid other than dexamethasone is used in a sustained release biodegradable intracanalicular insert utilized in the present invention, a dose of that other glucocorticoid may be contained in the insert that is equivalent to any of the dose amounts and ranges disclosed above for dexamethasone. Suitable conversion factors between glucocorticoids are known in the art and may be applied (see the section "Definitions" above).

The disclosed amounts of glucocorticoid, such as dexamethasone, including the mentioned variances, refer to both the final content of the active principle in the insert, as well as to the amount of active principle used as a starting component when manufacturing the insert.

In certain embodiments, the glucocorticoid, such as dexamethasone, may be contained in the insert utilized in the methods of the invention such that particles of the glucocorticoid are dispersed or distributed in a hydrogel comprised of a polymer network. In certain embodiments, the particles are homogeneously dispersed in the hydrogel. The hydrogel may prevent the drug particles from agglomerating and may provide a matrix for the particles which releases the drug in a sustained manner upon contact with the tear fluid.

In certain embodiments of the invention, the glucocorticoid particles, such as the dexamethasone particles, may be microencapsulated. The term "microcapsule" is sometimes defined as a roughly spherical particle with a size varying between e.g. about 50 nm to about 2 mm. Microcapsules have at least one discrete domain (or core) of active agent encapsulated in a surrounding or partially surrounding material, sometimes also referred to as a shell. A suitable agent for microencapsulating the glucocorticoid, such as the dexamethasone, for the purposes of the present invention, is poly(lactic-co-glycolic acid).

In one embodiment, the glucocorticoid particles, such as the dexamethasone particles, may have a small particle diameter and may be micronized particles. In another embodiment, the glucocorticoid particles, such as the dexamethasone particles, may not be micronized. Micronization refers to the process of reducing the average diameter of particles of a solid material. Particles with reduced diameters may have inter alia higher dissolution rates, which increases the bioavailability of active pharmaceutical ingredients. In the composite materials field, particle size is known to affect the mechanical properties when combined with a matrix, with smaller particles providing superior reinforcement for a given mass fraction. Thus, a hydrogel matrix within which micronized glucocorticoid particles are dispersed may have improved mechanical properties (e.g. brittleness, strain to failure, etc.) compared to a similar mass fraction of larger glucocorticoid particles. Such properties are important in manufacturing, during administration, and during degradation of the insert. Micronization may also promote a more homogeneous distribution of the active ingredient in the chosen dosage form or matrix. In certain embodiments, the glucocorticoid particles, such as the dexamethasone particles, for use in the present invention may have a D50 particle size of less than about 10 µm and/or a D99 particle size of less than about 50 µm. In certain specific embodiments of the invention using dexamethasone as the glucocorticoid, the dexamethasone particles have a D90 of equal to or less than about 5 µm, and a D98 of equal to or less than about 10 µm. In embodiments in which another glucocorticoid than dexamethasone is used in the present invention similar particle sizes may apply as disclosed for dexamethasone. Generally speaking, for any glucocorticoid including dexamethasone, non-limiting particle sizes of about 100 µm or below, or of about 75 µm or below may be used, such as a particle size from about 20 µm to about 75 µm, or from about 20 µm to about 50 µm.

Micronized dexamethasone particles may be purchased per specification from the supplier (e.g. from Pfizer or Sanofi), or may be prepared according to any of the processes known in the art. For example, micronization processes may be used as e.g. exemplarily disclosed for certain glucocorticoids in EP 2043698 A2 or in EP 2156823 A1 (which are incorporated herein by reference), or processes that are analogous to an exemplary procedure as e.g. disclosed in WO 2016/183296 A1 (which is incorporated herein by reference), Example 13, with respect to a different active agent.

The Polymer Network:

In certain embodiments, the hydrogel may be formed from precursors having functional groups that form crosslinks to create a polymer network. These crosslinks between polymer strands or arms may be chemical (i.e., may be covalent bonds) and/or physical (such as ionic bonds, hydrophobic association, hydrogen bridges etc.) in nature.

The polymer network may be prepared from precursors, either from one type of precursor or from two or more types of precursors that are allowed to react. Precursors are chosen in consideration of the properties that are desired for the resultant hydrogel. There are various suitable precursors for use in making the hydrogels. Generally, any pharmaceutically acceptable and crosslinkable polymers forming a hydrogel may be used for the purposes of the present invention. The hydrogel and thus the components incorporated into it, including the polymers used for making the polymer network, should be physiologically safe such that they do not elicit e.g. an immune response or substantial immune response or other adverse effects. Hydrogels may be formed from natural, synthetic, or biosynthetic polymers.

Natural polymers may include glycosaminoglycans, polysaccharides (e.g. dextran), polyaminoacids and proteins or mixtures or combinations thereof, while this list is not intended to be limiting.

Synthetic polymers may generally be any polymers that are synthetically produced from a variety of feedstocks by different types of polymerization, including free radical polymerization, anionic or cationic polymerization, chain-growth or addition polymerization, condensation polymerization, ring-opening polymerization etc. The polymerization may be initiated by certain initiators, by light and/or heat, and may be mediated by catalysts. Synthetic polymers may in certain embodiments be used to lower the potential of allergies in dosage forms that do not contain any ingredients from human or animal origin.

Generally, for the purposes of the present invention one or more synthetic polymers of the group comprising one or more units of polyethylene glycol (PEG), polyethylene oxide, polypropylene oxide, polyvinyl alcohol, poly (vinylpyrrolidinone), polylactic acid, polylactic-co-glycolic acid, random or block copolymers or combinations/mixtures of any of these can be used, while this list is not intended to be limiting.

To form covalently crosslinked polymer networks, the precursors may be covalently crosslinked with each other. In certain embodiments, precursors with at least two reactive centers (for example, in free radical polymerization) can serve as crosslinkers since each reactive group can participate in the formation of a different growing polymer chain.

The precursors may have biologically inert and hydrophilic portions, e.g., a core. In the case of a branched polymer, a core refers to a contiguous portion of a molecule joined to arms that extend from the core, where the arms carry a functional group, which is often at the terminus of the arm or branch. Multi-armed PEG precursors are examples of such precursors and are used in particular embodiments of the present invention as further disclosed herein.

A hydrogel for use in the present invention can be made e.g. from one multi-armed precursor with a first (set of) functional group(s) and another (e.g. multi-armed) precursor having a second (set of) functional group(s). By way of example, a multi-armed precursor may have hydrophilic arms, e.g., polyethylene glycol units, terminated with primary amines (nucleophile), or may have activated ester end groups (electrophile). The polymer network according to the present invention may contain identical or different polymer units crosslinked with each other. The precursors may be high-molecular weight components (such as polymers having functional groups as further disclosed herein) or low-molecular weight components (such as low-molecular amines, thiols, esters etc. as also further disclosed herein).

Certain functional groups can be made more reactive by using an activating group. Such activating groups include (but are not limited to) carbonyldiimidazole, sulfonyl chloride, aryl halides, sulfosuccinimidyl esters, N-hydroxysuccinimidyl (abbreviated as "NHS") ester, succinimidyl ester, benzotriazolyl ester, thioester, epoxide, aldehyde, maleimides, imidoesters, acrylates and the like. The NHS esters are useful groups for crosslinking with nucleophilic polymers, e.g., primary amine-terminated or thiol-terminated polyethylene glycols. An NHS-amine crosslinking reaction may be carried out in aqueous solution and in the presence of buffers, e.g., phosphate buffer (pH 5.0-7.5), triethanolamine buffer (pH 7.5-9.0), borate buffer (pH 9.0-12), or sodium bicarbonate buffer (pH 9.0-10.0).

In certain embodiments, each precursor may comprise only nucleophilic or only electrophilic functional groups, so long as both nucleophilic and electrophilic precursors are used in the crosslinking reaction. Thus, for example, if a crosslinker has only nucleophilic functional groups such as amines, the precursor polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly (allyl amine), or amine-terminated di- or multifunctional poly(ethylene glycol) can be also used to prepare the polymer network of the present invention.

In one embodiment of the present invention a precursor for the polymer network forming the hydrogel in which the glucocorticoid is dispersed to form the insert according to the present invention has about 2 to about 16 nucleophilic functional groups each (termed functionality), and in another embodiment a precursor has about 2 to about 16 electrophilic functional groups each (termed functionality). Reactive precursors having a number of reactive (nucleophilic or electrophilic) groups as a multiple of 4, thus for example 4, 8 and 16 reactive groups, are particularly suitable for the present invention. However, any number of functional groups, such as including any of 2, 3, 4, 5, 6, 7, 8, 9, 10, 11, 12, 13, 14, 15, or 16 groups, is possible for precursors to be used in accordance with the present invention, while ensuring that the functionality is sufficient to form an adequately crosslinked network.

PEG Hydrogels:

In certain embodiments of the present invention, the polymer network forming the hydrogel contains polyethylene glycol ("PEG") units. PEGs are known in the art to form hydrogels when crosslinked, and these PEG hydrogels are suitable for pharmaceutical applications e.g. as matrix for drugs intended to be administered to any part of the human or animal body.

The polymer network of the hydrogel inserts of the present invention may comprise one or more multi-arm PEG units having from 2 to 10 arms, or from 4 to 8 arms, or 4, 5, 6, 7 or 8 arms. In certain embodiments, the PEG units used in the hydrogel of the present invention have 4 arm. In certain embodiments, the PEG units used in the hydrogel of the present invention have 8 arms. In certain embodiments, PEG units having 4 arms and PEG units having 8 arms are used in the hydrogel of the present invention. In certain particular embodiments, one or more 4-armed PEGs is/are utilized.

The number of arms of the PEG used contributes to controlling the flexibility or softness of the resulting hydrogel. For example, hydrogels formed by crosslinking 4-arm PEGs are generally softer and more flexible than those formed from 8-arm PEGs of the same molecular weight. In particular, if stretching the hydrogel prior to (or also after) drying as disclosed herein below in the section relating to the manufacture of the insert is desired, a more flexible hydrogel may be used, such as a 4-arm PEG, optionally in combination with another multi-arm PEG, such as an 8-arm PEG as disclosed above, or another (different) 4-arm PEG.

In certain embodiments of the present invention, polyethylene glycol units used as precursors have an average molecular weight in the range from about 2,000 to about 100,000 Daltons, or in a range from about 10,000 to about 60,000 Daltons, or in a range from about 15,000 to about 50,000 Daltons. In certain particular embodiments the polyethylene glycol units have an average molecular weight in a range from about 10,000 to about 40,000 Daltons. In specific embodiments, the polyethylene glycol units used for making the hydrogels according to the present invention have an average molecular weight of about 20,000 Daltons. Polyethylene glycol precursors of different molecular weight may be combined with each other. When referring herein to a PEG material having a particular average molecular weight, such as about 20,000 Daltons, a variance of ±10% is intended to be included, i.e., referring to a material having an average molecular weight of about 20,000 Daltons also refers to such a material having an average molecular weight of about 18,000 to about 22,000 Daltons. As used herein, the abbreviation "k" in the context of the molecular weight refers to 1,000 Daltons, i.e., "20 k" means 20,000 Daltons.

In a 4-arm ("4a") PEG, in certain embodiments each of the arms may have an average arm length (or molecular weight) of the total molecular weight of the PEG divided by 4. A 4a20 kPEG precursor, which is a particularly suitably precursor for use in the present invention thus has 4 arms with an average molecular weight of about 5,000 Daltons each and a total molecular weight of 20,000 Daltons. An 8a20 k PEG precursor, which could also be used in combination with or alternatively to the 4a20 kPEG precursor in the present invention, thus has 8 arms ("8a") each having an average molecular weight of 2,500 Daltons and a total molecular weight of 20,000 Daltons. Longer arms may provide increased flexibility as compared to shorter arms. PEGs with longer arms may swell more as compared to PEGs with shorter arms. A PEG with a lower number of arms also may swell more and may be more flexible than a PEG with a higher number of arms. In certain particular embodiments, only a 4-arm PEG precursor is utilized in the present invention. In certain other embodiments, a combination of a 4-arm PEG precursor and an 8-arm precursor is utilized in the present invention. In addition, longer PEG arms have higher melting temperatures when dry, which may provide more dimensional stability during storage.

In certain embodiments, electrophilic end groups for use with PEG precursors for preparing the hydrogels of the present invention are N-hydroxysuccinimidyl (NHS) esters, including but not limited to NHS dicarboxylic acid esters such as the succinimidylmalonate group, succinimidylmaleate group, succinimidylfumarate group, "SAZ" referring to a succinimidylazelate end group, "SAP" referring to a succinimidyladipate end group, "SG" referring to a succinimidylglutarate end group, and "SS" referring to a succinimidylsuccinate end group.

In certain embodiments, nucleophilic end groups for use with electrophilic group-containing PEG precursors for preparing the hydrogels of the present invention are amine (denoted as "NH$_2$") end groups. Thiol (—SH) end groups or other nucleophilic end groups are also possible.

In certain embodiments of the present invention, 4-arm PEGs with an average molecular weight of about 20,000 Daltons and electrophilic end groups as disclosed above (such as the SAZ, SAP, SG and SS end groups, particularly the SG end group) are crosslinked for forming the polymer network and thus the hydrogel according to the present invention. Suitable PEG precursors are available from a number of suppliers, such as Jenkem Technology and others.

Reactions of e.g. nucleophilic group-containing crosslinkers and electrophilic group-containing PEG units, such as reaction of amine group-containing crosslinkers with activated ester-group containing PEG units, result in a plurality of PEG units being crosslinked by a hydrolyzable linker having the formula:

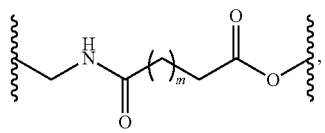

wherein m is an integer from 0 to 10, and specifically is 1, 2, 3, 4, 5, 6, 7, 8, 9, or 10. For a SAZ-end group, m would be 6, for a SAP-end group, m would be 3, for a SG-end group, m would be 2 and for an SS-end group, m would be 1.

In certain embodiments, the polymer precursors used for forming the hydrogel according to the present invention may be selected from 4a20 kPEG-SAZ, 4a20 kPEG-SAP, 4a20 kPEG-SG, 4a20 kPEG-SS, 8a20 kPEG-SAZ, 8a20 kPEG-SAP, 8a20 kPEG-SG, 8a20 kPEG-SS, or mixtures thereof, with one or more PEG- or lysine based-amine groups selected from 4a20 kPEG-NH$_2$, 8a20 kPEG-NH$_2$, and trilysine, or a trilysine salt or derivative, such as trilysine acetate.

In certain embodiments, the SG end group is utilized in the present invention. This end group may provide for a shorter time until the hydrogel is biodegraded in an aqueous environment such as in the tear fluid, when compared to the use of other end groups, such as the SAZ end group, which provides for a higher number of carbon atoms in the linker and may thus be more hydrophobic and therefore less prone to ester hydrolysis than the SG end group.

In particular embodiments, a 4-arm 20,000 Dalton PEG precursor having a SG end group (as defined above), is crosslinked with a crosslinking agent having one or more reactive amine end groups. This PEG precursor is abbreviated herein as 4a20 kPEG-SG. A schematic chemical structure of 4a20 kPEG-SG is reproduced below:

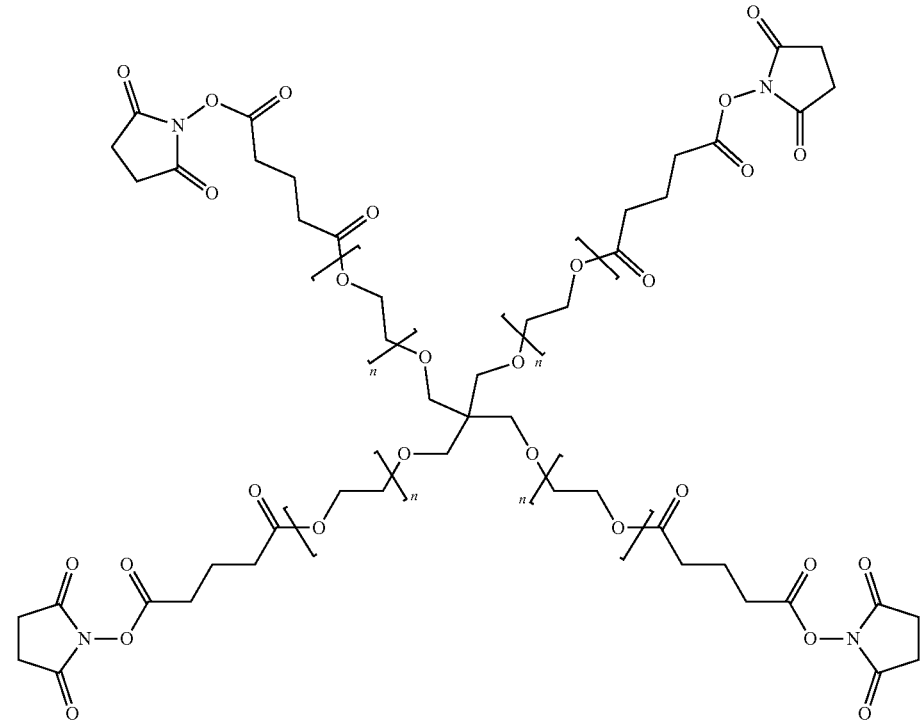

In this formula, n is determined by the molecular weight of the respective PEG-arm.

In certain particular embodiments, the crosslinking agent (herein also referred to as "crosslinker") used is a low-molecular weight component containing nucleophilic end groups, such as amine or thiol end groups. In certain embodiments, the nucleophilic group-containing crosslinking agent is a small molecule amine with a molecular weight below 1,000 Da. In certain embodiments, the nucleophilic-group containing crosslinking agent comprises two, three or more primary aliphatic amine groups. Suitable crosslinking agents for use in the present invention are (without being limited to) spermine, spermidine, lysine, dilysine, trilysine, tetralysine, polylysine, ethylenediamine, polyethylenimine, 1,3-diaminopropane, 1,3-diaminopropane, diethylenetriamine, trimethylhexamethylenediamine, 1,1,1-tris(aminoethyl)ethane, their pharmaceutically acceptable salts, hydrates or other solvates and their derivatives such as conjugates (as long as sufficient nucleophilic groups for crosslinking remain present), and any mixtures thereof. A particular crosslinking agent for use in the present invention is trilysine or a trilysine salt or derivative, such as trilysine acetate. Other low-molecular weight multi-arm amines may be used as well. The chemical structure of trilysine is reproduced below:

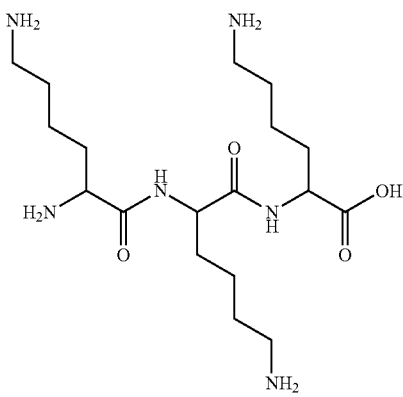 [SMILES: NCCCCC(N)C(=O)NC(CCCCN)C(=O)NC(CCCCN)C(=O)O]

In very particular embodiments of the present invention, a 4a20 kPEG-SG precursor is reacted with trilysine acetate, to form the polymer network.

In certain embodiments, the nucleophilic group-containing crosslinking agent is bound to or conjugated with a visualization agent. Fluorophores such as fluorescein, rhodamine, coumarin, and cyanine can be used as visualization agents as disclosed herein. In specific embodiments of the present invention, fluorescein is used as the visualization agent. The visualization agent may be conjugated with the crosslinking agent e.g. through some of the nucleophilic groups of the crosslinking agent. Since a sufficient amount of the nucleophilic groups are necessary for crosslinking, "conjugated" or "conjugation" in general includes partial conjugation, meaning that only a part of the nucleophilic groups are used for conjugation with the visualization agent, such as about 1% to about 20%, or about 5% to about 10%, or about 8% of the nucleophilic groups of the crosslinking agent may be conjugated with a visualization agent. In specific embodiments, the crosslinking agent is trilysine acetate and is conjugated with fluorescein.

In other embodiments, the visualization agent may also be conjugated with the polymer precursor, e.g. through certain reactive (such as electrophilic) groups of the polymer precursors. In certain embodiments, the crosslinking agent itself or the polymer precursor itself may contain an e.g. fluorophoric or other visualization-enabling group.

In the present invention, conjugation of the visualization agent to either the polymer precursor(s) or to the crosslinking agent as disclosed below is intended to keep the visualization agent in the hydrogel while the active agent is released into the tear fluid, thus allowing confirmation of insert presence within the canaliculus by a convenient, non-invasive method.

In certain embodiments, the molar ratio of the nucleophilic and the electrophilic end groups reacting with each other is about 1:1, i.e., one amine group is provided per one electrophilic, such as SG, group. In the case of 4a20 kPEG-SG and trilysine (acetate) this results in a molar ratio of the two components of about 1:1 as the trilysine has four primary amine groups that may react with the electrophilic SG ester group. However, an excess of either the electrophilic (e.g. the NHS end groups, such as the SG) end group precursor or of the nucleophilic (e.g. the amine) end group precursor may be used. In particular, an excess of the nucleophilic, such as the amine end group containing precursor or crosslinking agent may be used. In certain embodiments, the molar ratio of the electrophilic group containing precursor to the nucleophilic group-containing crosslinking agent, such as the molar ratio of 4a20 kPEG-SG to trilysine acetate, is from about 1:2 to about 0.5:1, or from about 1:2 to about 2:1.

Finally, in alternative embodiments the amine linking agent can also be another PEG precursor with the same or a different number of arms and the same or a different arm length (average molecular weight) as the 4a20 kPEG-SG, but having terminal amine groups, i.e., 4a20 kPEG-NH$_2$.

Additional Ingredients:

The insert of the present invention may contain, in addition to the polymer units forming the polymer network as disclosed above and the active principle, other additional ingredients. Such additional ingredients are for example salts originating from buffers used during the preparation of the hydrogel, such as phosphates, borates, bicarbonates, or other buffer agents such as triethanolamine. In certain embodiments of the present invention sodium phosphate buffers (specifically, mono- and dibasic sodium phosphate) are used.

In some embodiments, the insert contains a preservative. The preservative may be present in the insert at a concentration of about 0.005 wt % to about 0.1 wt %, about 0.02 wt % to about 0.04 wt % based on the total weight of the insert. Suitable preservatives for ocular formulations include, but are not limited to, a quaternary ammonium compound such as benzalkonium chloride (i.e., N-benzyl-N—($C_8$-$C_{18}$ alkyl)-N,N-dimethylammonium chloride), benzoxonium chloride, polyquatemium-1, polyquatemium-42, cetrimide, or the like; antioxidants such as vitamin A, vitamin E, vitamin C, retinyl palmitate, and selenium; oxidizing agents such as sodium perborate and stabilized oxochloro complex; the amino acids cysteine and methionine; an amidine such as chlorhexidine; citric acid and sodium citrate; ionic buffers such as borate, sorbitol, propylene glycol and zinc; mercury-based such as thimerosal and phenylmercuric nitrate/acetate; alkyl parabens such as methyl paraben and propyl paraben; octadecyldimethylbenzyl ammonium chloride, hexamethonium chloride, benzethonium chloride, phenol, catechol, resorcinol, cyclohexanol, 3-pentanol, m-cresol, phenylmercuric nitrate, phenylmercuric acetate or phenylmercuric borate, sodium chlorite, alcohols, such as chlorobutanol, butyl or benzyl alcohol or phenyl ethanol, guanidine derivatives, such as chlorohexidine or polyhexamethylene biguanide, sodium perborate, diazolidinyl urea, sorbic acid and/or combinations thereof.

While preservatives in multi-dose formulations of topical ophthalmic medications help maintain sterility, they can be toxic to the ocular surface. For example, benzalkonium chloride (BAK)—used in approximately 70% of ophthalmic formulations—causes cytotoxic damage to conjunctival and corneal epithelial cells, resulting in signs and symptoms of ocular surface disease (OSD) including ocular surface staining, increased tear break-up time, and higher OSD symptom scores. These adverse effects are more problematic with chronic exposure, as in lifetime therapy for glaucoma, but can also manifest after exposure as brief as 7 days.

According to at least one embodiment, the insert includes a preservative other than a quarternary ammonium compound, such as benzalkonium chloride, or the insert is preservative-free. In embodiments, the insert utilized in the present invention is preservative-free or at least does not contain a substantial amount of preservative. For example, the insert may contain less than about 0.005 wt %, less than about 0.001 wt %, or 0 wt % of preservative. The insert as described herein may be free of any one or more of the preservatives described above. In some embodiments, the insert is free of a quarternary ammonium compound. For example, the insert is free of benzalkonium chloride.

Preservative-free inserts that form hydrogrels according to embodiments herein can provide a suitable sustained release drug delivery platform for treating allergic conjunctivitis. Hydrogels can be formulated as biocompatible hydrophilic cross-linked polymer networks that swell when exposed to water. The glucocorticoid can be incorporated into the polymer matrix without preservatives. The rate of drug delivery, and duration of action of a hydrogel-based therapeutic, may be determined by the degree of polymeric crosslinking and the relative sizes of the inter-crosslink mesh openings and the drug to be delivered. A DEXTENZA® intracanalicular insert is a preservative-free sustained-release formulation of dexamethasone 0.4 mg encapsulated in a hydrogel sustained delivery system can be used to treat allergic conjunctivitis. As it dissolves within the canaliculus, the insert delivers a tapering dose of dexamethasone to the tear film up to 30 days.

In a further specific embodiment, the insert utilized in the present invention does not contain any ingredients of animals or human origin, but only contains synthetic ingredients.

In certain embodiments, the inserts utilized in the present invention contain a visualization agent. Visualization agents to be used according to the present invention are all agents that can be conjugated with the components of the hydrogel or can be entrapped within the hydrogel, and that are visible, or may be made visible when exposed e.g. to light of a certain wavelength, or that are contrast agents. Suitable visualization agents for use in the present invention are (but are not limited to) e.g. fluoresceins, rhodamines, coumarins, cyanines, europium chelate complexes, boron dipyromethenes, benzofrazans, dansyls, bimanes, acridines, triazapentalenes, pyrenes and derivatives thereof. Such visualization agents are commercially available e.g. from TCI. In certain embodiments the visualization agent is a fluorophore, such as fluorescein or comprises a fluorescein moiety. Visualization of the fluorescein-containing insert is possible by illumination with blue light. The fluorescein in the intracanalicular insert illuminates when excited with blue light enabling confirmation of insert presence. In specific embodiments, the visualization agent is conjugated with one of the components forming the hydrogel. For example, the visualization agent, such as fluorescein, is conjugated with the crosslinking agent, such as the trilysine or trilysine salt or derivate (e.g. the trilysine acetate), or with the PEG-component e.g. by means of reacting NHS-fluorescein with trilysine acetate. Conjugation of the visualization agent prevents the visualization agent from being eluted or released out of the insert. Since a sufficient amount of the nucleophilic groups (at least more than one molar equivalent) are necessary for crosslinking, partial conjugation of the visualization agent with e.g. the crosslinking agent as disclosed above may be performed.

The inserts utilized in the present invention may in certain embodiments contain a surfactant. The surfactant may be a non-ionic surfactant. The non-ionic surfactant may comprise a poly(ethylene glycol) chain. Exemplary non-ionic surfactants are poly(ethylene glycol) sorbitan monolaurate commercially available as Tween® (and in particular Tween® 20, a PEG-20-sorbitan monolaurate, or Tween® 80, a PEG-80-sorbitan monolaurate), poly(ethylene glycol) ester of castor oil commercially available as Cremophor (and in particular Cremophor40, which is PEG-40-castor oil), and an ethoxylated 4-tert-octylphenol/formaldehyde condensation polymer which is commercially available as Tyloxapol and others such as Triton. A surfactant may aid in dispersing the active principle and may prevent particle aggregation, and may also reduce possible adhesion of the hydrogel strand to the tubing during drying.

Formulation:

In certain embodiments, inserts utilized in the present invention comprise a glucocorticoid, such as dexamethasone, a polymer network made from one or more polymer precursors as disclosed herein in the form of a hydrogel, and optional additional components such as visualization agents, salts etc. remaining in the insert from the production process (such as phosphate salts used as buffers etc.). In certain preferred embodiments, the glucocorticoid is dexamethasone. In particular embodiments, the insert is preservative-free.

In some embodiments, the inserts according to the present invention in a dry state contain from about 30% to about 70% by weight glucocorticoid, such as dexamethasone, and from about 25% to about 60% by weight polymer units, such as those disclosed above. In further embodiments, the inserts according to the present invention in a dry state contain from about 30% to about 60% by weight glucocorticoid, such as dexamethasone, and from about 30% to about 60% by weight polymer units, such as those disclosed above.

In certain other embodiments, the inserts according to the present invention in a dry state contain from about 50% to about 56% by weight dexamethasone and from about 36% to about 46% by weight PEG units.

In certain embodiments, the inserts may contain in a dry state about 0.1% to about 1% by weight visualization agent, such as fluorescein or a molecule comprising a fluorescein moiety. Also in certain embodiments, the inserts according to the present invention may contain in a dry state about 0.5% to about 5% by weight of one or more buffer salt(s) (separately or taken together). In such embodiments, the insert in a dry state may contain, e.g., from about 0.01% to about 2% by weight or from about 0.05% to about 0.5% by weight of a surfactant.

In certain embodiments, the balance of the insert in its dry state (i.e., the remainder of the formulation when glucocorticoid, such as dexamethasone, and polymer hydrogel, such as trilysine-crosslinked PEG hydrogel, and optionally visualization agent, such as fluorescein, have already been taken account of) may be salts remaining from the buffer used during manufacture of the inserts as disclosed herein, or may be other ingredients used during manufacturing of the insert (such as surfactants if used). In certain embodiments, such salts are phosphate, borate or (bi) carbonate salts. In one embodiment a buffer salt is sodium phosphate (mono- and/or dibasic).

The amounts of the glucocorticoid and the polymer(s) may be varied, and other amounts of the glucocorticoid and the polymer hydrogel than those disclosed herein may also be used to prepare inserts utilized in the invention.

In certain embodiments, the maximum amount (in weight %) of drug within the formulation is about two times the amount of the polymer (e.g., PEG) units, but may be higher in certain cases, as long as the mixture comprising e.g., the precursors, visualization agent, buffers and drug (in the state before the hydrogel has gelled completely) can be uniformly cast into a desired mold or thin-diameter tubing and/or the hydrogel is still sufficiently stretchable as disclosed herein, and/or sufficiently increases in diameter upon hydration as also disclosed herein.

In certain embodiments, solid contents of about 20% to about 50% (w/v) (wherein "solids" means the combined weight of polymer precursor(s), optional visualization agent, salts and the drug in solution) are utilized for forming the hydrogel of the inserts according to the present invention.

In certain embodiments, the water content of the hydrogel in a dry (dehydrated/dried) state may be low, such as not more than 1% by weight of water. The water content may in certain embodiments also be lower than that, possibly no more than about 0.25% by weight or even no more than about 0.10% by weight.

Dimensions of the Insert and Dimensional Change Upon Hydration Through Stretching:

The dried insert may have different geometries, depending on the method of manufacture, such as the inner diameter or shape of a mold or tubing into which the mixture comprising the hydrogel precursors including the glucocorticoid is cast prior to complete gelling. In one embodiment, the insert has a cylindrical or an essentially cylindrical shape, with a round or an essentially round cross-section. The shape of the insert produced from such a tubing may also be described as a fiber, strand or rod.

Other geometries of the outer insert shape or its cross-section may also be used. For example, instead of the round diameter fiber, an oval (or elliptical) diameter fiber may be used. As long as the insert expands in diameter upon hydration in the canaliculus to an average hydrated diameter as disclosed herein, the exact cross-sectional shape is not decisive, as tissue will form around the insert.

The polymer network, such as the PEG network, of the hydrogel insert according to certain embodiments of the present invention may be semi-crystalline in the dry state at or below room temperature, and amorphous in the wet state. Even in the stretched form, the dry insert may be dimensionally stable at or below room temperature, which may be advantageous for administering the insert into the canaliculus, and also for quality control.

Upon hydration of the insert in the canaliculus by the tear fluid (which can be simulated in vitro e.g. by immersing the insert into PBS, pH 7.4 at 37° C. after 24 hours, which is considered equilibrium) the dimensions of the insert according to the invention may change. Generally, the diameter of the insert may increase, while its length may decrease or in certain embodiments may stay the same or essentially the same. An advantage of this dimensional change is that, while the insert in its dry state is sufficiently thin to be administered and placed into the canaliculus through the punctum (which itself is smaller in diameter than the canaliculus) upon hydration and thereby through expansion of its diameter it fits closely into the canaliculus and thus acts as a canalicular plug. The insert therefore provides for lacrimal occlusion and thereby tear conservation in addition to releasing the active principle in a controlled manner to the tear fluid over a certain period of time as disclosed herein.

In certain embodiments, this dimensional change is enabled at least in part by the "shape memory" effect introduced into the insert by means of stretching the insert in the longitudinal direction during its manufacture as also disclosed herein. In certain embodiments, this stretching may be performed in the wet state, i.e., before drying. However, in certain other embodiments, the stretching of the hydrogel strands (once casted and cured) may be performed in the dry state (i.e., after drying the hydrogel strands). It is noted that if no stretching is performed at all the insert may merely swell due to the uptake of water, but the dimensional change of an increase in diameter and a decrease in length disclosed herein may not be achieved, or may not be achieved to a large extent. This could result in a less than optimal fixture of the insert in the canaliculus, and could potentially lead to the insert being cleared (potentially even prior to the release of the complete dose of the active principle) through the nasolacrimal duct or through the punctum. If this is not desired, the hydrogel fiber may e.g. be dry or wet stretched in order to provide for expansion of the diameter upon rehydration.

In the hydrogels of the present invention, a degree of molecular orientation may be imparted by stretching the material then allowing it to solidify, locking in the molecular orientation. The molecular orientation provides one mechanism for anisotropic swelling upon contacting the insert with a hydrating medium such as tear fluid. Upon hydration, the insert of certain embodiments of the present invention will swell only in the radial dimension, while the length will either decrease or be maintained or essentially maintained. The term "anisotropic swelling" means swelling preferentially in one direction as opposed to another, as in a cylinder that swells predominantly in diameter, but does not appreciably expand (or does even contract) in the longitudinal dimension.

Among other factors influencing the possibility to stretch the hydrogel and to elicit dimensional change of the insert upon hydration is the composition of the polymer network. In the case PEG precursors are used, those with a lower number of arms (such as 4-armed PEG precursors) contribute to providing a higher flexibility in the hydrogel than those with a higher number of arms (such as 8-armed PEG precursors). If a hydrogel contains more of the less flexible components (e.g. a higher amount of PEG precursors containing a larger number of arms, such as the 8-armed PEG units), the hydrogel may be firmer and less easy to stretch without fracturing. On the other hand, a hydrogel containing more flexible components (such as PEG precursors containing a lower number of arms, such as 4-armed PEG units) may be easier to stretch and softer, but also swells more upon hydration. Thus, the behavior and properties of the insert once it has been administered and is rehydrated can be tailored by means of varying structural features as well as by modifying the processing of the insert after it has been initially formed.

The dried insert dimensions inter alia may depend on the amount of glucocorticoid incorporated as well as the ratio of glucocorticoid to polymer units and can additionally be controlled by the diameter and shape of the mold or tubing in which the hydrogel is allowed to gel. The diameter of the dried insert may be further controlled by (wet or dry) stretching of the hydrogel strands once formed as disclosed herein. The dried hydrogel strands (after stretching) are cut into segments of the desired length to form the insert; the length can thus be chosen as desired.

In one embodiment, the present invention utilizes a sustained release biodegradable intracanalicular insert comprising a hydrogel and a glucocorticoid, wherein the insert in a dry state has an average length of about 2.5 mm to about 3.5 mm or about 3 mm. In a particular embodiment, the glucocorticoid is dexamethasone.

In certain embodiments, the stretching thus creates a shape memory, meaning that the insert upon hydration when administered into the canaliculus and once it comes into contact with the tear fluid, will shrink in length and widen in diameter until it approaches (more or less) its equilibrium dimensions, which are determined by the original molded dimensions and compositional variables. While the narrow dry dimensions facilitate administration of the insert through the punctum into the canaliculus, the widened diameter and shortened length after administration yield a shorter but wider insert that fits closely into and occludes the canaliculus while releasing active agent primarily at its proximal surface (the surface of the insert that is in contact with the tear fluid and that is directed toward the punctum opening).

Release of the Active and Biodegradation of the Insert:

In one embodiment, the present invention relates to a sustained release biodegradable intracanalicular insert comprising a hydrogel and a glucocorticoid, wherein the insert provides for a release of a therapeutically effective amount of the glucocorticoid for a period, e.g., of at least 25 days after administration (i.e., after having been inserted into the canaliculus). In a particular embodiment, the glucocorticoid is dexamethasone.

It is believed that release of the glucocorticoid into the tear fluid is determined by the glucocorticoid's solubility in an aqueous environment. One particular glucocorticoid for use according to the present invention is dexamethasone. The solubility of dexamethasone has been determined to be very low in an aqueous medium (less than 100 μg/mL), such as the tear fluid. When administered to the canaliculus, the dexamethasone is released from the insert primarily at its surface proximal to the tear fluid and thus proximal to the eye surface (i.e., at the insert surface facing the punctum opening).

Figure 8:
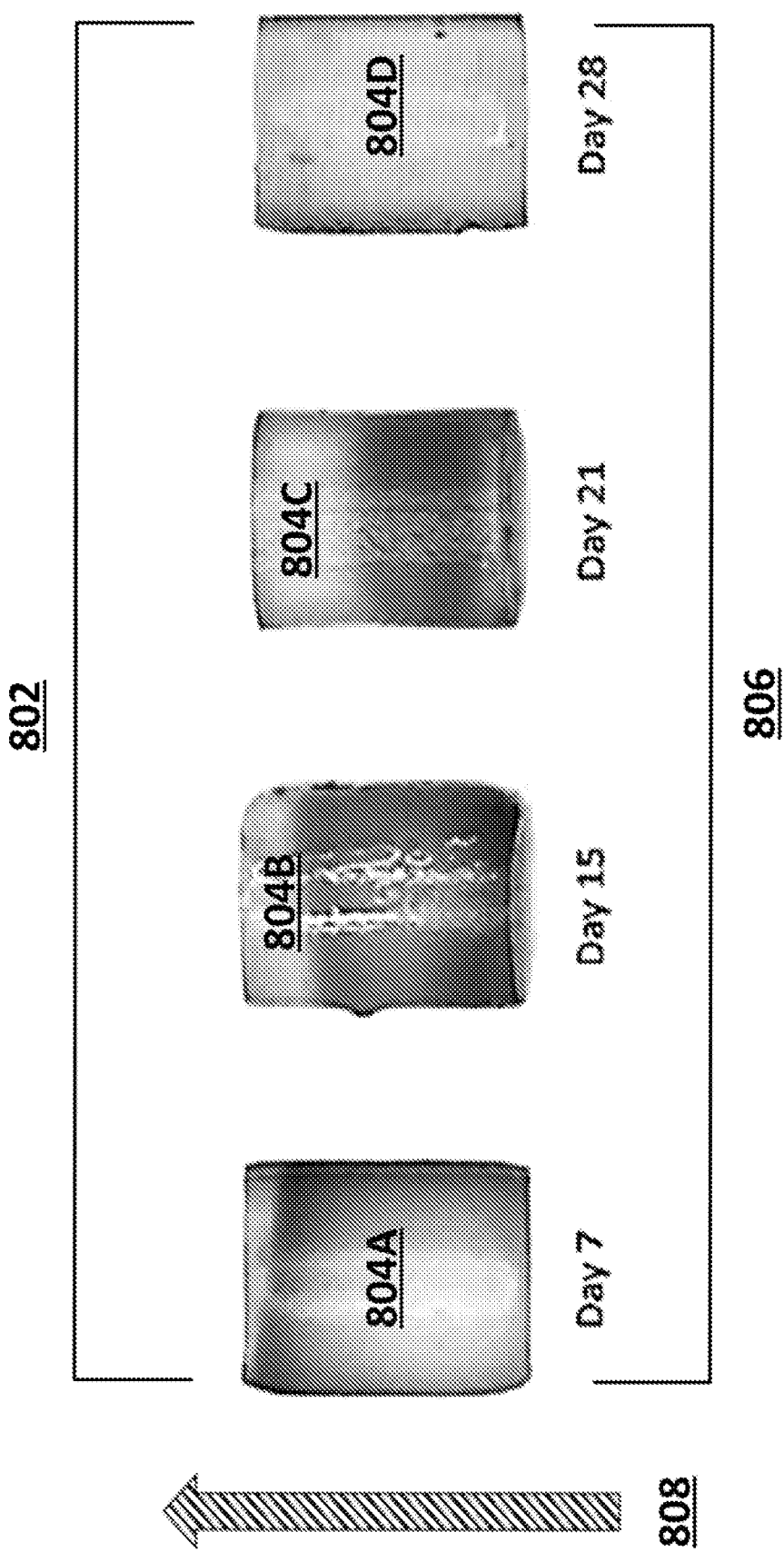
FIG. 8 shows dexamethasone release from a 0.37 mg dexamethasone insert according to an embodiment of the invention at different study timepoints. Dexamethasone is released over time into the tear fluid primarily from the insert site proximal to the punctum opening. The darker shading of the insert reflects the presence of dexamethasone, and the clearing reflects the zone of the insert depleted of dexamethasone. Dexamethasone is essentially completely released from the 0.37 mg insert after 28 days.

In certain embodiments, the active agent gradually gets dissolved and diffuses out of the hydrogel into the tear fluid. This happens primarily in a unidirectional manner, starting at the interface of the insert and the tear fluid at the proximal surface of the insert. The "drug front" generally progresses in the opposite direction, i.e., away from the proximal surface until eventually the entire insert is depleted of active agent. This is illustrated in FIG. 8.

In certain embodiments, the insert according to the present invention provides for the release of a glucocorticoid, such as dexamethasone, for a period of about 6 hours or longer, such as for a period of about 12 hours or longer, or 1 week or longer, or 2 weeks, or one month or longer.

In certain embodiments, after administration, the levels of active agent released from the insert per day remain constant or essentially constant over a certain period of time (due to the limitation of release based on the active agent's solubility), such as for about 7 days, or for about 11 days, or for about 14 days in the case of dexamethasone. Then the amount of active agent released per day may decrease for another period of time (also referred to as "tapering"), such as for a period of about 7 additional days (or longer in certain embodiments) in the case of dexamethasone until all or substantially all of the active agent has been released and the "empty" hydrogel remains in the canaliculus until it is fully degraded and/or until it is cleared (disposed/washed out) through the nasolacrimal duct.

In one embodiment, when drug is released primarily from the proximal surface of the insert, this region of the hydrogel insert becomes devoid of drug particles and may therefore also be called the "clearance zone". In certain embodiments, upon hydration the "clearance zone" is thus a region of the insert that has a concentration of active agent that is less than the active agent in another region of the hydrated hydrogel. As the clearance zone increases, it creates a concentration gradient within the insert that may lead to tapering of the release rate of the drug.

Concurrently with the drug diffusing out of the hydrogel (and also after the entire amount of drug has diffused out of the hydrogel), the hydrogel may be slowly degraded e.g. by means of ester hydrolysis in the aqueous environment of the tear fluid. At advanced stages of degradation, distortion and erosion of the hydrogel begins to occur. As this happens, the hydrogel becomes softer and more liquid (and thus its shape becomes distorted) until the hydrogel finally dissolves and is resorbed completely. However, as the hydrogel becomes softer and thinner and its shape becomes distorted, at a certain point it may no longer remain at its intended site in the canaliculus to which it had been administered, but it may progress deeper into the canaliculus and eventually may be cleared (disposed/washed out) through the nasolacrimal duct.

In one embodiment, the persistence of the hydrogel within an aqueous environment such as in the human eye (including the canaliculus) depends inter alia on the structure of the linker that crosslinks the polymer units, such as the PEG units, in the hydrogel. In certain embodiments, the hydrogel is biodegraded within a period of about 1 month, or about 2 months, or about 3 months, or up to about 4 months, after administration. However, since during the degradation process in the aqueous environment, such as in the tear fluid within the canaliculus, the hydrogel gradually becomes softer and distorted, the insert may be cleared (washed out/disposed) through the nasolacrimal duct before it is completely biodegraded.

In embodiments of the present invention, the hydrogel and thus the insert remains in the canaliculus for a period of up to about 1 month, or up to about 2 months, or up to about 3 months, or up to about 4 months, after administration.

In certain embodiments of the invention, in the case the glucocorticoid is dexamethasone, the entire amount of dexamethasone may be released prior to the complete degradation of the hydrogel, and the insert may persist in the canaliculus thereafter, for a period of altogether up to about 1 month after administration, or up to about 2 months after administration, or up to about 3 months, or up to about 4 months, after administration. In certain other embodiments, the hydrogel is fully biodegraded when the glucocorticoid, such as dexamethasone, has not yet been completely released from the insert.

In certain embodiments, in vitro release tests may be used to compare different inserts (e.g. of different production batches, of different composition, and of different dosage strength etc.) with each other, for example for the purpose of quality control or other qualitative assessments. The in vitro-release of a glucocorticoid from the inserts of the invention can be determined by various methods, such as under non-sink simulated physiological conditions in PBS (phosphate-buffered saline, pH 7.4) at 37° C., with daily replacement of PBS in a volume comparable to the tear fluid in the human eye.

II. Manufacture of the Insert

In certain embodiments the method of manufacturing the insert to utilize in the present invention comprises the steps of forming a hydrogel comprising a polymer network (e.g., comprising PEG units) and glucocorticoid particles dispersed in the hydrogel, shaping or casting the hydrogel and drying the hydrogel. In one embodiment the glucocorticoid, such as dexamethasone, may be used in micronized form as disclosed herein for preparing the insert. In another embodiment, the glucocorticoid, such as dexamethasone, may be used in non-micronized form for preparing the insert.

Suitable precursors for forming the hydrogel of certain embodiments of the invention are as disclosed above in the section relating to the insert itself. In certain specific embodiments, the hydrogel is made of a polymer network comprising crosslinked polyethylene glycol units as disclosed herein. The polyethylene glycol (PEG) units in particular embodiments are multi-arm, such as 4-arm, PEG units having an average molecular weight from about 2,000 to about 100,000 Daltons, or from about 10,000 to about 60,000 Daltons, or from about 15,000 to about 50,000 Daltons, or of about 20,000 Daltons. Suitable PEG precursors having reactive groups such as electrophilic groups as disclosed herein are crosslinked to form the polymer network. Crosslinking may be performed by means of a crosslinking agent that is either a low molecular compound or another polymeric compound, including another PEG precursor, having reactive groups such as nucleophilic groups as also disclosed herein. In certain embodiments, a PEG precursor with electrophilic end groups is reacted with a crosslinking agent (a low-molecular compound, or another PEG precursor) with nucleophilic end groups to form the polymer network.

In specific embodiments, the method of manufacturing the insert of the present invention comprises mixing and reacting an electrophilic group-containing multi-arm polyethylene glycol, such as 4a20 kPEG-SG, with a nucleophilic group-containing crosslinking agent, such as trilysine acetate, in a buffered solution in the presence of dexamethasone particles, and allowing the mixture to gel. In certain embodiments, the molar ratio of the electrophilic groups in the PEG precursor to the nucleophilic groups in the crosslinking agent is about 1:1, but may also be in a range from about 2:1 to about 1:2.

In certain embodiments, a visualization agent as disclosed herein is included in the mixture forming the hydrogel so that the insert can be visualized once it has been administered into the canaliculus. For example, the visualization agent may be a fluorophore, such as fluorescein or a molecule comprising a fluorescein moiety, or another visualization agent as disclosed above. In certain embodiments, the visualization agent may be firmly conjugated with one or more components of the polymer network so that it remains in the insert at all times until the insert is biodegraded.

The visualization agent may for example be conjugated with either the polymer, such as the PEG, precursor, or the (polymeric or low molecular weight) crosslinking agent. In specific embodiments, the visualization agent is fluorescein and is conjugated to the trilysine acetate crosslinking agent prior to reacting the crosslinking agent with the PEG precursor. For example, in the case of fluorescein, NHS-fluorescein (N-hydroxysuccinimidyl-fluorescein) may be reacted with trilysine acetate, and completion of the formation of the trilysine-fluorescein conjugate may be monitored (e.g. by means of RP-HPLC with UV-detection). This conjugate may then be used further to crosslink the polymeric precursor(s), such as the 4a20 kPEG-SG.

In certain particular embodiments, during the manufacture of an insert of the present invention a (optionally buffered) mixture/suspension of the glucocorticoid and the PEG precursor(s), such as the dexamethasone and the 4a20 kPEG-SG, in water is prepared. This glucocorticoid/PEG precursor mixture is then combined with a (optionally buffered) solution containing the crosslinking agent and the visualization agent conjugated thereto, such as the lysine acetate/fluorescein conjugate. The resulting combined mixture thus contains the glucocorticoid, the polymer precursor(s), the crosslinking agent, the visualization agent and (optionally) buffer.

In certain embodiments, once the mixture of the electrophilic group-containing polymer precursor, the nucleophilic group-containing crosslinking agent, the glucocorticoid, such as dexamethasone, optionally the visualization agent (optionally conjugated to e.g. the crosslinking agent), and optionally buffer has been prepared (i.e., after these components have been combined), the resulting mixture is cast into a suitable mold or tubing prior to complete gelling in order to provide the desired final shape of the hydrogel. The mixture is then allowed to gel. The resulting hydrogel is then dried.

In case the final shape of the insert is cylindrical or is essentially cylindrical, a hydrogel strand or fiber (the terms "strand" or "fiber" or "rod" are used interchangeably herein) is prepared by casting the hydrogel precursor mixture comprising the glucocorticoid particles into a fine diameter tubing, such as a polyurethane (PU) tubing. Different geometries and diameters of the tubing may be used, depending on the desired final cross-sectional geometry of the hydrogel fiber, its initial diameter (which may still be decreased by means of stretching), and depending also on the ability of the reactive mixture to uniformly fill the tubing and to be removed from the tubing after drying. Thus, the inside of the tubing may have a round geometry or a non-round geometry, such as an oval (or other) geometry.

In certain embodiments, after the hydrogel strand has been formed and has been left to cure and to complete the gelling process within the tubing, the hydrogel strand may be longitudinally stretched in the wet or dry state as disclosed herein. The stretching may result in a dimensional change of the insert upon hydration, e.g. when placed into the canaliculus. In particular embodiments, the hydrogel strand is stretched prior to (complete) drying by a stretching factor in a range, e.g., of about 1 to about 4, or of about 1.5 to about 3, or of about 2.2 to about 2.8, or of about 2.5 to about 2.6. In certain embodiments, the stretching may be performed when the hydrogel strand is still in the tubing. Alternatively, the hydrogel strand may be removed from the tubing prior to being stretched. In the case dry stretching is performed in certain embodiments of the invention, the hydrogel strand is first dried and then stretched (when still inside of the tubing, or after having been removed from the tubing). When wet stretching is performed in certain embodiments of the invention, the hydrogel is stretched in a wet state (i.e., before it has dried completely) and then left to dry under tension. Optionally, heat may be applied upon stretching.

After stretching and drying the hydrogel strand may be removed from the tubing and cut into segments of a desired average length, such as disclosed herein, to produce the final insert (if cut within the tubing, the cut segments are removed from the tubing after cutting).

Figure 4:
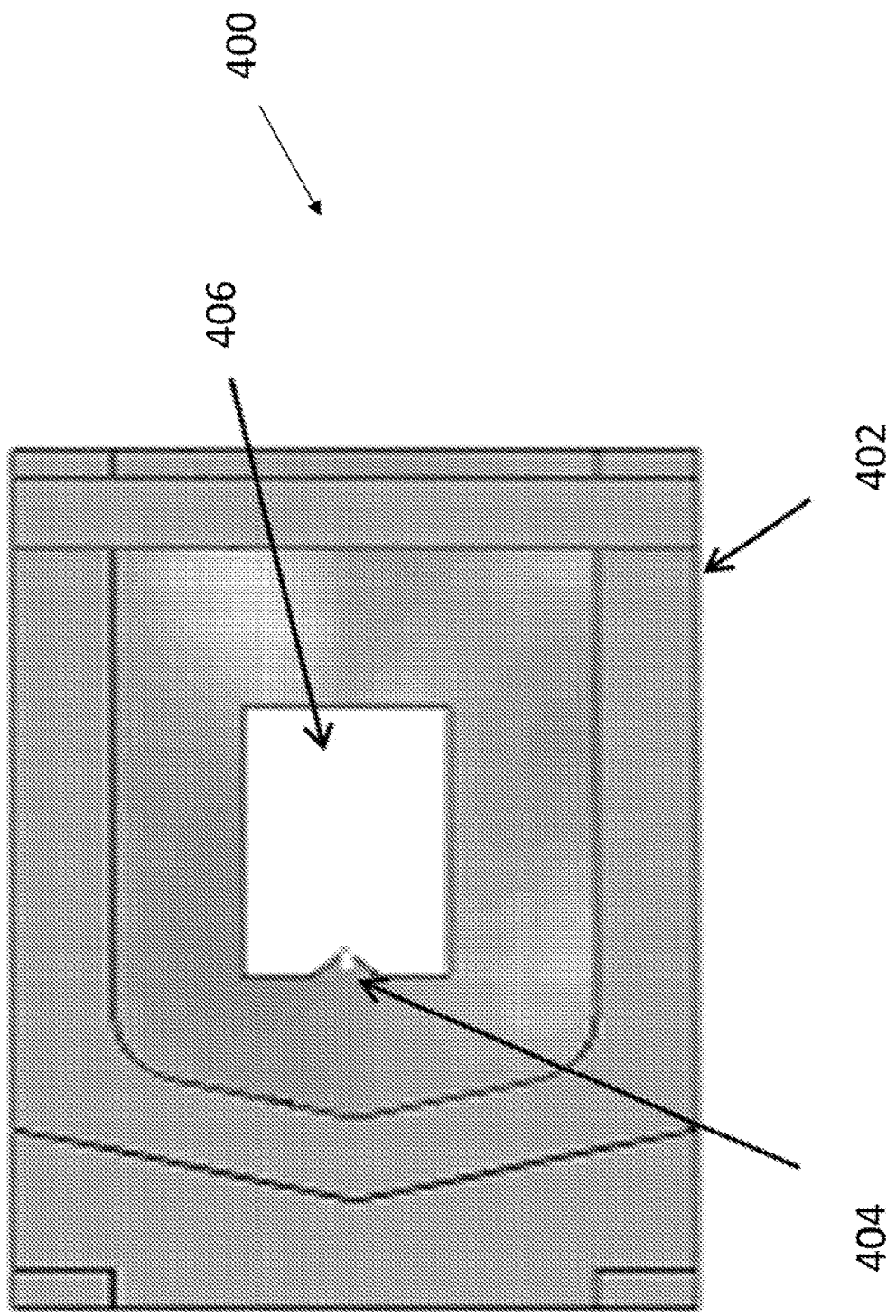
FIG. 4 shows a schematic representation of an exemplary insert packaging. The insert is placed into a foam carrier and sealed with a foil pouch.

After cutting, one or more insert may then be placed in packaging 400 that keeps out moisture, such as a sealed foil pouch 402 as illustrated in FIG. 4. The insert 404 may be attached to a mount or support to keep the insert in place, avoid damage, facilitate removal of the insert from the packaging 400 and to facilitate gripping/holding of the insert for administration to a patient. For example, an insert 404 may be placed in an opening of a foam carrier 406, with a portion of the insert protruding for easy removal and gripping (as illustrated in FIG. 4). The insert may be removed from the foam carrier by means of forceps and then immediately inserted into the canaliculus of the patient.

III. Therapy

In one embodiment, the present invention relates to a method of treating allergic conjunctivitis in a patient in need thereof, the method comprising administering to the patient a sustained release biodegradable intracanalicular insert as disclosed herein. The patient may be a human or animal subject in need of such therapy. In certain embodiments, the treatment is for ocular itching and or redness of the conjunctiva associated with allergic conjunctivitis. In certain embodiments, the insert is administered without human contact such as with a tool, applicator or device.

In one embodiment, the ophthalmic insert described herein releases at least 0.4 mg of dexamethasone following administration. Alternatively, as part of another embodiment, the ophthalmic insert described herein releases at most 0.4 mg of dexamethasone following administration. In another alterative embodiment, the ophthalmic insert described herein releases about 0.4 mg of dexamethasone following administration In another embodiment, the ophthalmic insert described herein releases about 0.4 mg of dexamethasone for up to 30 days following administration.

In another embodiment, treating as disclosed herein comprises a reduction in ocular itching following administration, e.g., of at least 15-days following administration.

In another embodiment, the allergic conjunctivitis as disclosed herein is caused by allergens selected from seasonal allergens and perennial allergens. Alternatively, as part of a another embodiment, the allergic conjunctivitis as disclosed herein is caused by allergens selected from timothy grass, white birch, meadow fescue, ragweed, Kentucky bluegrass, rye grass, maple, oak, dust mites, cat dander, cockroach, and dog dander.

In certain embodiments, an insert 504 is administered unilaterally or is administered bilaterally through the lower punctum 502 to the inferior canaliculus 506A, 506B as shown in FIG. 5. In other embodiments, the insert 504 is administered unilaterally or is administered bilaterally through the upper punctum 506A to the superior canaliculus. In certain embodiments, the insert 502 is administered both through the lower punctum 502 to the inferior canaliculus 506B and the upper punctum 506A to the superior canaliculus. The particular administration per eye can be independent of the other.

In certain embodiments, the insert is administered to the inferior vertical canaliculus and/or the superior vertical canaliculus.

In certain embodiments, the sustained release biodegradable intracanalicular insert comprises a visualization agent such as fluorescein to enable quick and noninvasive visualization of the insert when placed inside the canaliculus. In case the visualization agent is fluorescein, the insert may be visualized by illuminating with a blue light source and using a yellow filter.

Figure 6:
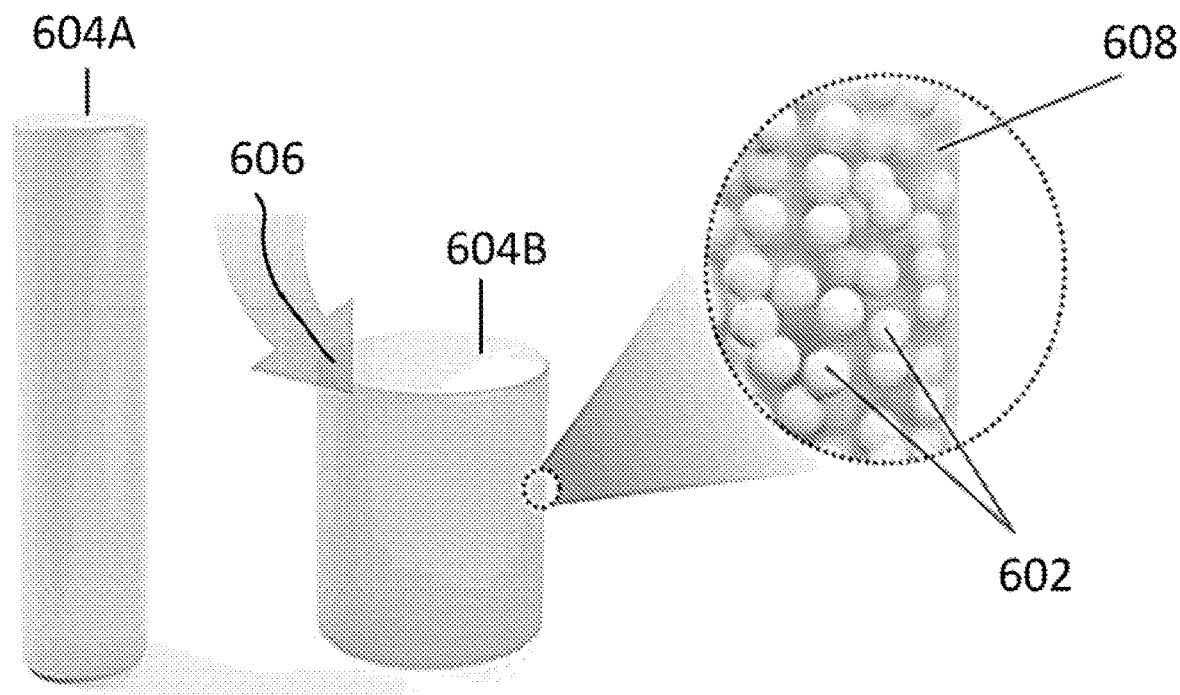
FIG. 6 shows a schematic exemplary representation of insert dimensional change upon contact with tear fluid after insertion of the dry insert into the canaliculus where it is hydrated by the tear fluid.

In certain embodiments, the glucocorticoid 602 such as dexamethasone is delivered from the insert 604A, 604B to the ocular surface through the tear film (or fluid) 606 (see FIG. 6). As shown in FIG. 6, the insert (before insertion) 604A has its original shape. After insertion into the canaliculus, upon contact with the tear fluid 606, the insert forms a hydrogel 604B containing the glucocorticoid 602 and medium 608 in which the glucocorticoid is suspended. FIG. 8 shows an insert following its placement in a canaliculus at Day 7 (804A), Day 15 (804B), Day 21 (804C) and Day 28 (804D). The insert 804A, 804B, 804C, 804D may be implanted at a site distal to the tear fluid 806. The glucocorticoid is released primarily from a proximal end 802 of the insert at the interface between the hydrogel and the tear fluid. The direction 808 of the glucocorticoid release may be from the distal site 806 toward the proximal end 802. The sustained glucocorticoid release rate is controlled by glucocorticoid solubility in the hydrogel matrix and the tear fluid. In certain embodiments, the glucocorticoid is dexamethasone, which has a low solubility in aqueous medium as disclosed herein.

In certain embodiments, the insert remains in the canaliculus after complete depletion of the glucocorticoid such as dexamethasone from the insert until the hydrogel has biodegraded and/or is disposed (washed out/cleared) through the nasolacrimal duct. As the hydrogel matrix of the insert is formulated to biodegrade e.g. via ester hydrolysis in the aqueous environment of the tear fluid in the canaliculus, the insert softens and liquefies over time and is cleared through the nasolacrimal duct without the need for removal. Unpleasant removal may thus be avoided. However, in case an insert should be removed e.g. because of a potential allergic reaction or other circumstances which require removal of the insert, such as an unpleasant foreign body sensation felt by a patient, or because treatment should be terminated for another reason, the insert may be expelled from the canaliculus e.g. manually.

In certain embodiments, the insert remains in the canaliculus for up to about 1 month, or up to about 2 months, or up to about 3 months, or up to about 4 months after administration.

In certain embodiments the systemic concentration of glucocorticoid such as dexamethasone after administration of the insert of the present invention is very low, such as below quantifiable amounts. This significantly reduces the risk of drug-to-drug interactions or systemic toxicity, which can be beneficial e.g. in older patients who are frequently suffering from ocular diseases and are additionally taking other medications.

In certain embodiments, as the insert of the present invention is located in the canaliculus and therefore not on the surface of the eye, and only one single administration is required to provide for the release of a glucocorticoid for an extended period of time as disclosed herein, the insert does not interfere or substantially interfere with contact lenses and may therefore be particularly suitable and convenient for patients wearing contact lenses.

In certain embodiments of the present invention, a further sustained release biodegradable intracanalicular insert is administered into the canaliculus through the ocular punctum while the first sustained release biodegradable intracanalicular insert is still retained in the canaliculus (which procedure is referred to as "insert stacking" or short "stacking"), either while the first insert still releases glucocorticoid, or after the first insert has been completely depleted of glucocorticoid, or after the first insert has been partially depleted of glucocorticoid by at least about 70%, or at least about 80%, or at least about 90% and/or the first insert releases a lower amount of glucocorticoid than initially after its administration.

In certain embodiments, insert stacking enables prolonged treatment with a glucocorticoid such as dexamethasone. In certain embodiments, insert stacking thus provides for a release of a therapeutically effective amount of glucocorticoid for a total period of up to about 14 days, or up to about 28 days, or up to about 42 days, or up to about 50 days, or up to about 2 months after administration of the first insert.

IV. Kit

In certain embodiments, the present invention is further directed to a kit comprising one or more insert(s) as disclosed herein or manufactured in accordance with the methods as disclosed herein.

In certain specific embodiments, the kit comprises one or more sustained release biodegradable intracanalicular insert(s), wherein each insert contains from about 160 μg to about 250 μg or from about 180 μg to about 220 μg or about 200 μg dexamethasone and has in a dry state an average diameter in the range of about 0.41 mm to about 0.49 mm and an average length in the range of about 2.14 mm to about 2.36 mm, and has in the hydrated state an average diameter in the range of about 1.35 mm to about 1.80 mm and a ratio of length to diameter of greater than 1, and wherein each insert provides for a release of dexamethasone for a period of up to about 14 days after administration.

In certain other specific embodiments, the kit comprises one or more sustained release biodegradable intracanalicular insert(s), wherein each insert contains from about 240 μg to about 375 μg or from about 270 μg to about 330 μg or about 300 μg dexamethasone and has in a dry state an average diameter in the range of about 0.44 mm to about 0.55 mm and an average length in the range of about 2.14 mm to about 2.36 mm, and has in the hydrated state an average diameter in the range of about 1.35 mm to about 1.80 mm and a ratio of length to diameter of greater than 1, and wherein each insert provides for a release of dexamethasone for a period of up to about 21 days after administration.

In certain embodiments, the kit further comprises instructions for using the one or more sustained release biodegradable intracanalicular insert(s). The instructions for using the one or more sustained release biodegradable intracanalicular insert(s) may be in the form of an operation manual for the physician who is administering the insert(s). The kit may further comprise a package insert with product-related information.

In certain embodiments, the kit may further comprise one or more means for administration of the one or more sustained release biodegradable intracanalicular insert(s). The means for administration may be for example one or more suitable tweezer(s) or forceps, either for one time use or for repeated use. For instance, suitable forceps are blunt (non-toothed). The means for administration may also be an injection device such as a syringe or applicator system.

In certain embodiments, the kit may further comprise an ophthalmic dilator to dilate the punctum prior to the administration of the one or more sustained release biodegradable intracanalicular insert(s) and thereby facilitates insertion of the insert(s) through the punctum into the canaliculus. A dilator may also be combined/integrated with forceps or an applicator, such that e.g. one end of the device is a dilator, and the other end of the device is suitable to administer the insert. Alternatively, the kit may also contain a modified applicator that e.g. has a tapered tip that may be used for both dilation and insertion.

In certain embodiments, the one or more sustained release biodegradable intracanalicular insert(s) are individually packaged for a single administration. In certain embodiments, the one or more sustained release biodegradable intracanalicular insert(s) are individually packaged for a single administration by fixating each insert in foam carrier, which is sealed in a foil pouch. The foam carrier may have e.g. a V-notch or a circular incision with an opening at the bottom of the V-notch to hold the insert (see, for instance, also FIG. 1).

If two or more sustained release biodegradable intracanalicular inserts are contained in the kit, these inserts may be identical or different, and may contain identical or different doses of the glucocorticoid such as dexamethasone.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1: General Synthetic Methods

An exemplary protocol for ophthalmic inserts that can be used in accordance with the disclosed methods (e.g., DEX-TENZA®) is provided in the table below.

| Step | Component | Nominal amount | units | Percent |
|---|---|---|---|---|
| 1 | TLA (trilysine acetate) solution | | | |
| 1a | WFI | 26 | g | 96.6% |
| | NA2HPO4 | 0.65 | g | 2.4% |
| | TLA | 0.26 | g | 1.0% |
| | pH adjust | 8.4 | with 1N NaOH | |
| 2 | Total mass TLA/FL solution | 26.91 | g | |
| 2a | TLA solution | 16.045 | g | 99.7% |
| | Fluorescein (FL) hold 1-24 hours | 0.05 | g | 0.3% |
| 3 | Total mass TLA/FL syringe | 16.095 | g | |
| 4 | TLA/FL solution Dex syringe prep | 4.2 | g | |
| | Dexamethasone | 1.879 | g | 20.3% |
| | WFI | 7.4 | g | 79.7% |
| 5 | total mass Monobasic solution | 9.279 | | |
| 5a | NaH2PO4 | 0.29 | g | 0.9% |
| | WFI | 31.5 | g | 99.1% |
| | Check cnductivity | | | |
| 6 | total mass PEG solution | 31.79 | | |
| | Monobasic solution | 6.35 | g | 74.3% |
| | 4a20K PEG SG | 2.2 | g | 25.7% |
| 7 | Total mass PEG syringe | 8.55 | | |
| 8 | PEG solution PEG/DEX syringe | 5.62 | g | 1.44608187 |
| | Mix PEG and Dex syringes | | | |

-continued

| 9 | Final mix |
|---|---|
|  | mix TLA/FL with PEG/Dex |
| 10 | mold/dry |

| Calculation of final product | | | wet |
|---|---|---|---|
| Component | Wt % | mass (g) | wt % |
| Dexamethasone | 53% | 1.88 | 9.8% |
| 4a20K PEG SG | 41% | 1.45 | 7.6% |
| TLA | 1.15% | 0.040 | 0.2% |
| FL | 0.37% | 0.013 | 0.1% |
| Na2HPO4 | 2.87% | 0.101 | 0.5% |
| NaH2PO4 | 1.08% | 0.038 | 0.2% |
| Total dry product (uncut) |  | 3.52 | 18.4% |
| Water |  | 15.58 |  |
|  |  | 19.10 |  |

Example 2: Evaluation of Dexamethasone Inserts in Pre-Clinical Studies

Safety, tolerability, and drug release of the dexamethasone inserts comprising varying doses of the active ingredient were evaluated in beagle dogs.

Determination of Dexamethasone by LC-MS/MS

Dexamethasone concentration in plasma, aqueous humor and tear fluid samples were determined by high performance liquid chromatography combined with tandem mass spectrometry (LC-MS/MS) using a triple quadrupole mass spectrometer.

For preparation of tear fluid samples, deionized water was added to the tear fluid samples to obtain a volume of 50 μL for each tear sample. Then, 50 μL of internal standard solution (prednisolone-21 acetate) were added to each tear sample. For preparation of aqueous humor samples, 50 μL of each aqueous humor sample were mixed with 50 μL internal standard solution. Samples were centrifuged at 13,500 rpm for 5 min. For preparation of plasma samples, 50 μL beagle plasma were mixed with 200 μL internal standard solution in acetonitrile with 0.1% formic acid (v/v). Plasma samples were vortexed and then centrifuged at 4,000 rpm for 15 min. The different sample supernatants were used for LC-MS/MS analysis.

The high performance liquid chromatography (HPLC) system consisted of Shimadzu AD10vp pumps and a CTC autosampler. The mass spectrometer (MS) was an ABI 3000 tandem mass spectrometer. The instruments were operated by Analyst 1.4.2 software. The HPLC mobile phases were acetonitrile and HPLC-grade water with 0.1% formic acid (v/v). The column was kept at ambient temperature, the sample compartment was kept at 2-5° C. The analytes were eluted from the column at 0.8 mL/min using a gradient resulting from mixture of the mobile phases. Dexamethasone was ionized by negative ion electrospray. The MS system was operated at negative ion mode. Dexamethasone (391.0-361.1 m/z; retention time 1.23±0.5 min) and the internal standard (prednisolone-21 acetate, 401.2-321.0 m/z; 1.29±0.5 min) were fragmented in the MS. The total run time was 2.4 min. Dexamethasone concentration was determined from a calibration curve. Prior to analysis of the samples, the method was validated using dexamethasone-comprising beagle plasma and artificial tears. The method was shown to be reproducible, precise, linear, accurate and specific. The lower limit of quantification was determined to be 1.0 ng/mL, the lower limit of detection to be 0.08-0.06 ng/mL.

Drug Release from Inserts

In order to examine dexamethasone release from inserts according to the present invention comprising different dexamethasone doses, inserts comprising 0.22, 0.37, 0.46, 0.58, 0.65, 0.72, and 0.85 mg dexamethasone, respectively, were administered intracanalicularly to healthy beagle dogs (n=10-14 per dose). The inserts were generally prepared according to the method as described above in Example 1. The exact compositions of the inserts used in the present example are presented in Table 2.1.

TABLE 2.1

Compositions of the 0.22, 0.37, 0.46, 0.58, 0.65, 0.72, and 0.85 mg dexamethasone inserts in percent by weight (% w/w).

| | Dose | | | |
|---|---|---|---|---|
| | 0.22 mg | 0.37 mg | 0.46 mg | 0.58 mg |
| Micronized Dexamethasone | 37.1% | 55.0% | 48.0% | 63.8% |
| 4a20kPEG-SG | 55.5% | 39.6% | 45.9% | 31.9% |
| Trilysine Acetate | 1.5% | 1.1% | 1.3% | 0.9% |
| NHS-Fluorescein | 0.5% | 0.4% | 0.0% | 0.3% |
| Sodium Phosphate Dibasic | 4.4% | 3.9% | 4.0% | 2.6% |
| Sodium Phosphate Monobasic | 0.9% | 0.0% | 0.8% | 0.5% |
| Micronized Dexamethasone | 56.0% | 67.2% | 67.0% | |
| 4a20kPEG-SG | 38.8% | 29.0% | 29.1% | |
| Trilysine Acetate | 1.1% | 0.8% | 0.8% | |
| NHS-Fluorescein | 0.0% | 0.3% | 0.0% | |
| Sodium Phosphate Dibasic | 3.4% | 2.3% | 2.6% | |
| Sodium Phosphate Monobasic | 0.7% | 0.5% | 0.5% | |

Figure 7:
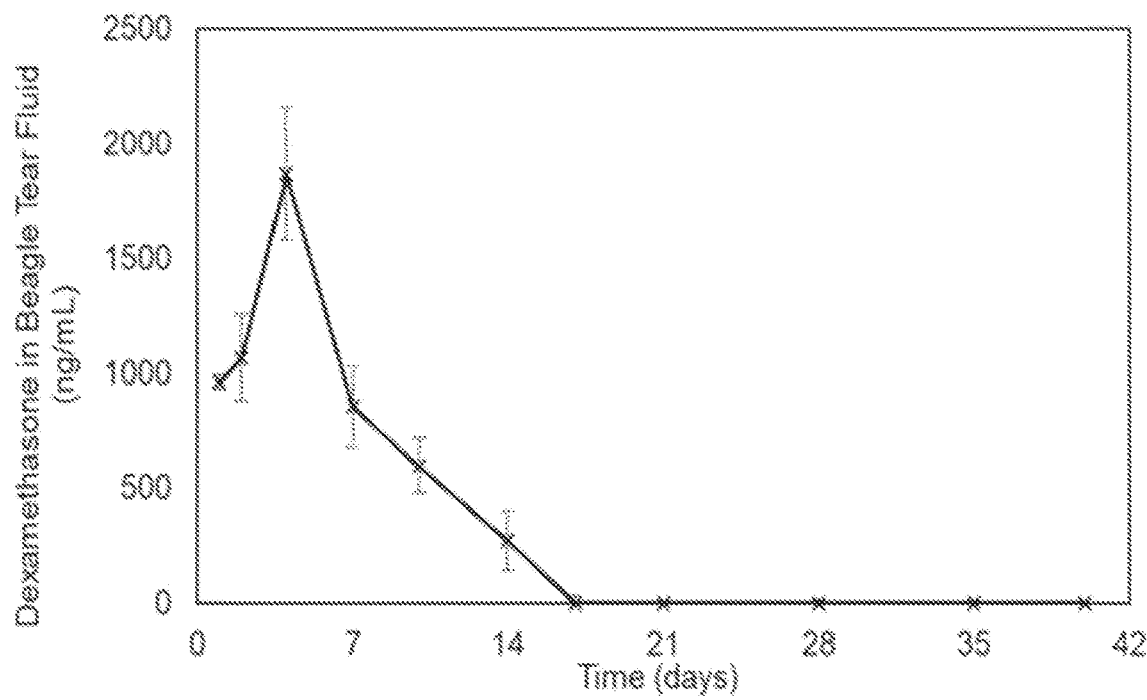
FIG. 7 shows a pharmacokinetic profile of dexamethasone release into tear fluid of beagle dogs from a 0.22 mg dexamethasone insert according to an embodiment of the invention. Tear fluid samples were collected from beagle eyes on days 1, 2, 4, 7, 10, 14, 17, 21, 28, 35, 37, and 42 after insertion of the insert into the canaliculus. Dexamethasone levels were measured by LC-MS/MS. Dexamethasone is presented as average values together with corresponding standard deviation error bars.

Aqueous humor and/or tear fluid samples were collected at indicated time points and analyzed using LC-MS/MS as described above (Tables 2.2 and 2.3; FIG. 7).

TABLE 2.2

Dexamethasone concentrations in tear fluid of beagle dogs delivered from different doses of dexamethasone inserts over time (S.D. = standard deviation).

| | Dexamethasone Dose | | | | | | | |
|---|---|---|---|---|---|---|---|---|
| | 0.22 mg | | 0.37 mg | | 0.46 mg | | 0.58 mg | |
| Day | Average (ng/mL) | S.D. (ng/mL) | Average (ng/mL) | S.D. (ng/mL) | Average (ng/mL) | S.D. (ng/mL) | Average (ng/mL) | S.D. (ng/mL) |
| 7 | 802 | 486 | 2796 | 1184 | 1040 | 525 | 1822 | 600 |
| 14 | 287 | 342 | 1535 | 750 | 1685 | 902 | 911 | 842 |
| 21 | 2 | 6 | 1146 | 320 | 499 | 418 | 1074 | 559 |
| 28 | 9 | 6 | 190 | 294 | 499 | 608 | 266 | 251 |

TABLE 2.2-continued

Dexamethasone concentrations in tear fluid of beagle dogs delivered from different doses of dexamethasone inserts over time (S.D. = standard deviation).

| | Dexamethasone Dose | | | | | |
|---|---|---|---|---|---|---|
| | 0.65 mg | | 0.72 mg | | 0.85 mg | |
| Day | Average (ng/mL) | S.D. (ng/mL) | Average (ng/mL) | S.D. (ng/mL) | Average (ng/mL) | S.D. (ng/mL) |
| 0.25 | | | 4534 | 2515 | | |
| 7 | 1119 | 772 | 3418 | 1659 | 737 | 358 |
| 14 | 1905 | 753 | 2538 | 642 | 1162 | 376 |
| 21 | 1070 | 728 | 2114 | 943 | 813 | 481 |
| 28 | 4390 | 806 | 1814 | 642 | 1553 | 733 |
| 35 | | | 1182 | 953 | | |

TABLE 2.3

Dexamethasone concentrations in aqueous humor of beagle dogs delivered from different doses of dexamethasone inserts over time.
Dexamethasone Concentration in Beagle Aqueous Humor
(Average ± Standard Deviation; ng/mL)

| | Dexamethasone Dose | | | |
|---|---|---|---|---|
| Day | 0.37 mg | 0.46 mg | 0.65 mg | 0.85 mg |
| 7 | 4.1 ± 2.6 | 7.7 ± 4.8 | 9.7 ± 3.4 | 7.4 ± 1.7 |
| 14 | 7.0 ± 3.9 | 7.9 ± 3.3 | 13.4 ± 1.7 | 13.3 ± 9.8 |
| 21 | 0.7 ± 1.0 | 7.5 ± 2.3 | 9.9 ± 1.9 | 7.7 ± 4.3 |
| 28 | 0.1 ± 0.2 | 1.9 ± 2.0 | 7.2 ± 2.1 | 5.9 ± 1.6 |

Pharmacokinetic results in tear fluid and aqueous humor samples were comparable. The values demonstrate a sustained release of dexamethasone with approximately constant levels of dexamethasone in the tear fluid and aqueous humor for several days depending on the dose, followed by a reduction in released drug amounts (tapering) until ultimately complete release. For instance, the 0.22 mg dexamethasone insert provided approximately constant dexamethasone levels in the tear fluid through 7 days followed by tapering from day 7 on With complete release of dexamethasone from the insert after 17 days following administration, thus resulting in an overall sustained release time of 17 days (FIG. 7). The 0.37 mg dexamethasone insert resulted in constant dexamethasone levels in the tear fluid through 21 days followed by tapering from day 21 through day 28 (Table 2.2). The tapering was also evident in the aqueous humor in the 0.37 mg dose at day 21 and the 0.46 mg dose at day 28 (Table 2.3). Of note, the aqueous humor and tear fluid dexamethasone concentrations resulting from the doses tested corresponded to the concentrations achieved by the application of MAXIDEX® eye drops (0.1% dexamethasone suspension) 4 times per day, which contain approximately 50 μg of dexamethasone per drop.

In summary, the dexamethasone concentrations in the aqueous humor of beagle dogs at 7 and 14 days were comparable between all doses tested. In addition, dexamethasone concentrations in tear fluid of beagle dogs were also comparable between all doses tested at 7 days.

Dexamethasone inserts were removed from the canaliculus by manual expression out of the punctum opening at selected time points for a defined number of animals. Remaining dexamethasone was extracted from the inserts and measured by LC-MS/MS as described above. The dexamethasone release rate per day prior to tapering and complete depletion from the insert (as evidenced by a decrease in dexamethasone concentration in tear fluid and/or aqueous humor) was calculated by determining the amount of dexamethasone released from the insert divided by the study day the insert was removed (Table 2.4). The results demonstrate that the determined dexamethasone release rates per day are comparable between all doses tested. This is in line with the fact that the dexamethasone release rate from an insert according to the present invention is regulated by the drug's solubility in the hydrogel matrix and the tear fluid. Dexamethasone is released from the insert primarily at the interface proximal to the tear fluid, i.e. from the insert portion facing the punctal opening (see also FIG. 8). The released drug levels thus remain largely constant until dexamethasone amounts in the insert are sufficiently reduced at the interface between the insert and the tear fluid, which leads to a gradual tapering effect as observed in the tear fluid and aqueous humor pharmacokinetic profiles. The average amount of dexamethasone released from the inserts according to the invention measured in these studies is essentially independent of the dexamethasone dose and is approximately 0.020 mg per day prior to tapering and complete depletion.

TABLE 2.4

Dexamethasone released per day from dexamethasone inserts comprising different doses prior to tapering and complete depletion (note that the two 0.85 mg inserts in the table were two different lots and measured in two different studies).

| | Average Total Dexamethasone Released Per Day from the Dexamethasone Inserts | | | | |
|---|---|---|---|---|---|
| | Dexamethasone Dose | | | | |
| Day | 0.37 mg | 0.46 mg | 0.65 mg | 0.85 mg | 0.85 mg |
| 7 | 0.015 | not tested | not tested | 0.024 | not tested |
| 14 | 0.020 | not tested | not tested | 0.025 | not tested |
| 21 | Tapering/ Depletion | 0.015 | 0.018 | 0.022 | 0.020 |
| 28 | Tapering/ Depletion | Tapering/ Depletion | Tapering/ Depletion | 0.019 | 0.017 |

The unidirectional drug release into the tear fluid is visually demonstrated for the 0.37 mg dexamethasone insert in FIG. 8. Although dexamethasone is released from the inserts prior to (complete) biodegradation of the insert (e.g. for the 0.37 mg dexamethasone insert the drug is completely released after approximately 28 days while the insert has not yet visually degraded to a large extent), extended presence of the drug depleted insert provides the additional longer-term benefit of lacrimal occlusion. In case in certain patients a more prolonged dexamethasone treatment is required or desired, a new insert could be placed on top of the prior, drug-depleted insert (also referred to as "insert stacking"). In any case, due to the insert being biodegradable, there is no need for removal of the insert, which greatly improves patient compliance.

Inserts comprising 0.2 mg and 0.3 mg dexamethasone, respectively, are expected to provide an essentially constant concentration of dexamethasone to the ocular surface for a period of up to about 7 days (for the 0.2 mg insert) and up to about 11, or up to about 14 days (for the 0.3 mg insert), after administration. The dexamethasone concentrations will then decrease (taper) over approximately the next 7 days until the active is completely depleted from the 0.2 mg and 0.3 mg dexamethasone insert. A sustained release of therapeutically effective amounts from the inserts according to the present invention is therefore provided for a period of about 14 days and for a period of about 21 days, respectively.

Safety and Tolerability of Inserts

Potential ocular toxicity, irritation, and systemic exposure were evaluated for a 0.72 mg dexamethasone insert over a 35-day period after intracanalicular insertion in beagle dogs. Reversibility and delayed occurrence of any toxic effects were assessed after a 14-day recovery period.

Two different types of inserts (and each of these both in a version with and a version without dexamethasone contained therein) were evaluated. The first insert type comprised 100% 4-arm 20 k PEG-SG hydrogel material (as described above in Example 1). The second insert type comprised a 50/50 blend of 4-arm 20 k PEG-SG and 4-arm 20 k PEG-SS hydrogel material. Both insert types were prepared according to the same method as described above in Example 1, except that for the second insert type the mentioned PEG precursor blend was used. For the exact composition of the 0.72 mg inserts reference is made to Table 2.1 (only that 50% of the 4a20 kPEG-SG in the 0.72 mg insert reported in Table 6 had been replaced by 4a20 kPEG-SS for those inserts that contained the PEG blend).

The study comprised two groups of beagle dogs. Animals of the first group (n=17) received inserts with dexamethasone, i.e. the first insert type with 100% 4-arm 20 k PEG-SG and dexamethasone in one eye and the second insert type with the 50/50 PEG blend and dexamethasone in the other eye, so each animal received one insert type (with dexamethasone) in each eye, resulting in a total exposure dose of 1.44 mg dexamethasone per animal. Animals of the second group (n=16) received the control inserts (without dexamethasone), i.e. the first insert type with 100% 4-arm 20 k PEG-SG in one eye and the second insert type with the 50/50 PEG blend in the other eye, so each animal received one insert type (without dexamethasone) in each eye.

Evaluations included any observed toxic effects, gross necropsy, and histopathological findings. Ophthalmic examinations included slit lamp biomicroscopy, fluorescein staining, fundoscopy, and tonometry. The slit lamp examination tracked alterations in the cornea, conjunctiva, iris, anterior chamber, and lens. The corneal surface was also assessed using fluorescein stain. The retina was examined for gross changes to the retina or optic nerve and noted as normal or abnormal. Daily clinical and food consumption observations were conducted. Body weight was measured weekly.

In summary, the dexamethasone inserts were well tolerated. Systemically, there were no treatment related effects seen on body weights, food consumption, hematology, clinical chemistry, coagulation, and urinalysis parameters. There were no effects seen in assessments of intraocular pressure and posterior segments of the eyes. Macroscopic and microscopic evaluations showed no test article related findings that would indicate direct test article toxicity. Findings in the punctum were likely due to procedural complication or normal background effects.

Observations from the ophthalmic examinations indicated mild to no irritation, as well as mild conjunctival congestion and discharge, and sluggish to absent pupillary light reflex. Findings were comparable across all groups independent of the type of insert (PEG compositions) and whether dexamethasone was present or not in the insert. The congestion findings were mild and not considered adverse. The discharge was considered to be related to the presence of the punctum plug and not specifically the materials comprising the test article. The sluggish to absent pupillary light reflex observations, which were considered to be due to observational subjectivity were limited and not considered adverse. No delayed occurrence of any toxic effects was observed after the 14-day recovery period.

Plasma concentrations (determined as described above) were below the lower limit of quantification (1.0 ng/mL) for all animals over the study duration, confirming the lack of clinically significant systemic exposure to dexamethasone even at a total dose as high as 1.44 mg per animal (resulting from the two inserts, one insert per eye).

In addition, the presence of the dexamethasone comprising as well as the vehicle control inserts were monitored over the 35-day study duration. For all groups the intracanalicular insert was still present in more than 84% of the animals after the treatment period. However, inserts comprising 100% 4-arm 20 k PEG-SG had a higher overall incidence of insert presence (retention) independent of the presence of dexamethasone or not when compared to the 50/50 PEG blend inserts.

Example 3: Evaluation of Dexamethasone Inserts in Clinical Study (Ocular Itching and Redness)

A randomized, double-masked, vehicle controlled Phase III study was performed using 96 randomized subjects. Key inclusion criteria included a history of allergic conjunctivitis, positive skin test to both seasonal and perennial allergen, and Bilateral Conjunctival Allergen Challenge (CAC) reaction. Subjects who met entry criteria were randomized to receive Dextenza® or PV (vehicle insert—no drug, punctum plug). Ocular itching was evaluated at 3, 5, and 7 minutes post-CAC at Day 7, Day 8, Day 14, and Day 15. Conjunctival redness was evaluated by the investigator at 7, 15, and 10 minutes post-CAC at all post-insertion visits.

Qualifying allergens included the seasonal allergens timothy grass, white birch, meadow fescue, ragweed, Kentucky bluegrass, rye grass, maple, oak, and dust mites; and perennial allergens included cat dander, cockroach, and dog dander.

Figure 2:
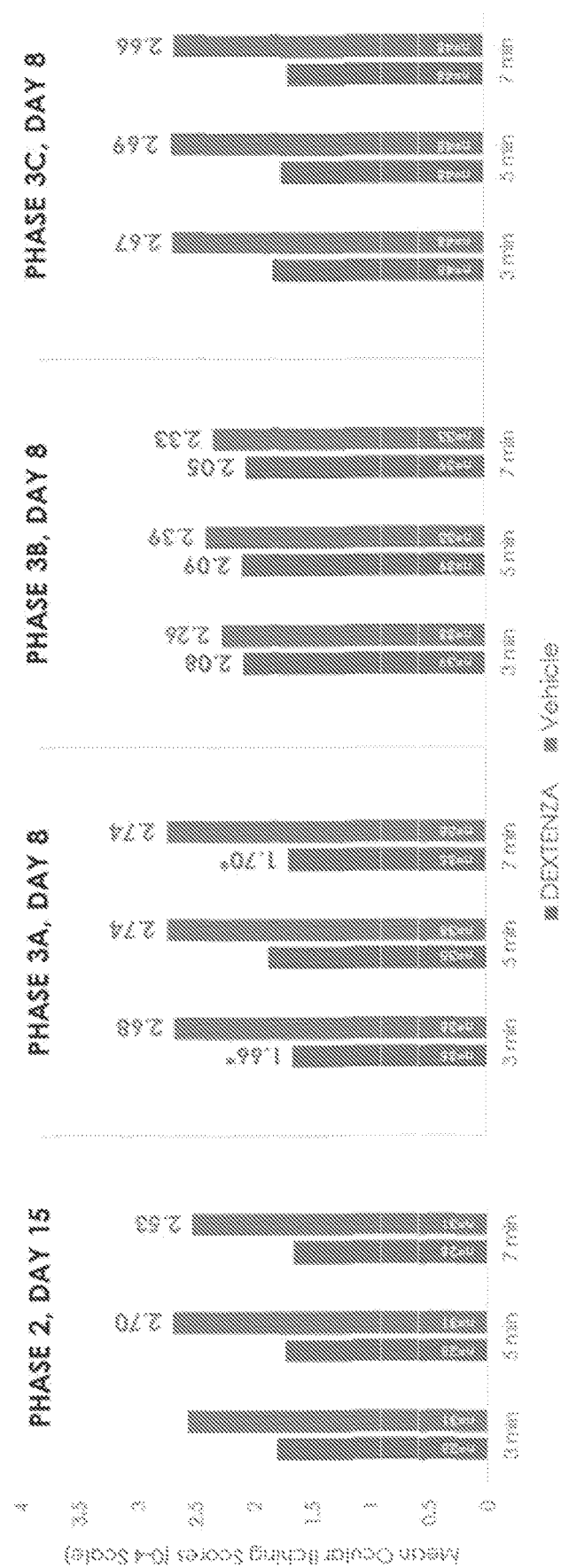
FIG. 2 shows an alternative representation of the mean ocular itching scores for studies using Dextenza®.
Figure 3:
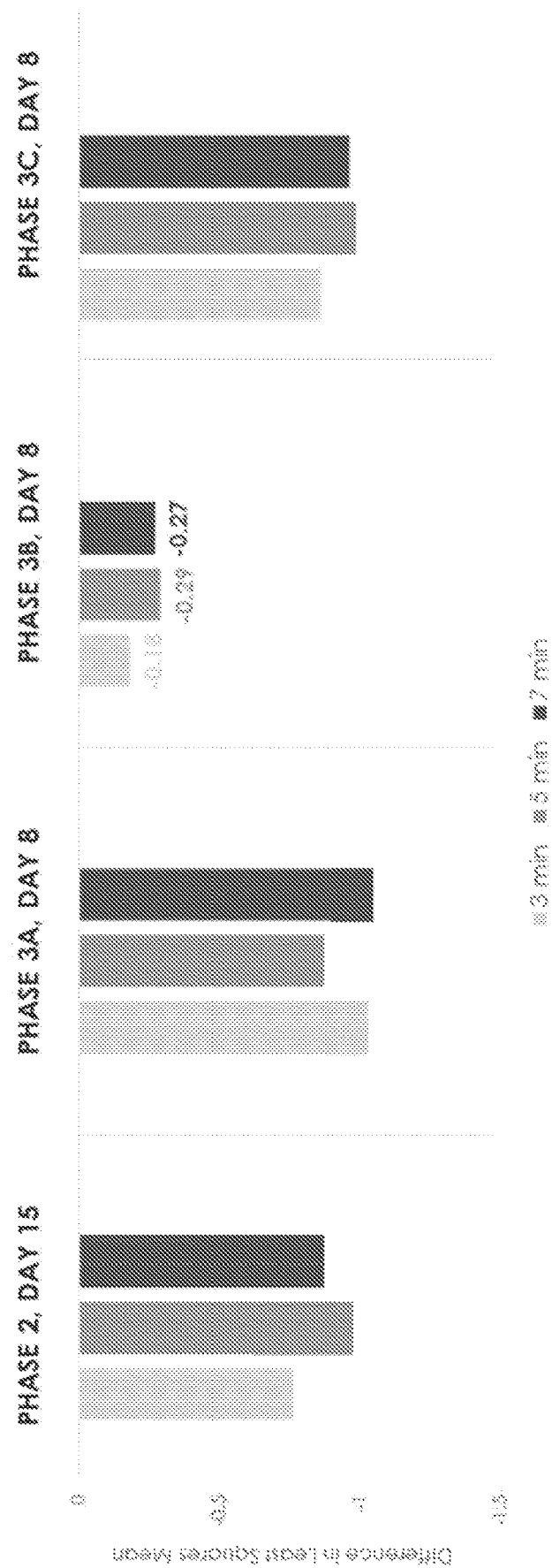
FIG. 3 shows an alternative representation of the mean ocular itching scores for studies using Dextenza®.

The results for the clinical study are shown in FIG. 1-3. For the primary endpoint at Visit 6b (Day 8; 8 Hours post Visit 6a), this study demonstrated a statistically significant ($P<0.0001$) difference favoring subjects who received DEXTENZA for lowering ocular itch scores compared with subjects who received vehicle insert at all time points (3 min, 5 min, and 7 min) post-CAC. For the primary endpoint at Visit 6b, the difference in ocular itching scores favored DEXTENZA over vehicle by 0.86 units at 3 minutes ($P<0.0001$), 0.98 units at 5 min ($P<0.0001$) and 0.96 units at 7 min ($P<0.0001$). For secondary endpoints at all other visits (Visit 5, Visit 6a, Visit 7, Visit 8a, Visit 8b), subjects treated with DEXTENZA did better than vehicle for ocular itching scores at 3 min, 5 min, 7 min and 10 min post-CAC (P<0.05 for all time points at all visits except Visit 5, 3 minutes).

Example 4: Evaluation of Dexamethasone Inserts in Clinical Studies for Allergic Conjunctivitis (Efficacy and Safety)

Four clinical studies, one phase II (Study 1) and three phase III (Study 2, Study 3, and Study 4), were conducted to evaluate the efficacy and safety of DEXTENZA for the treatment of signs and symptoms of allergic conjunctivitis. All studies were multi-center, randomized, double-masked and placebo (vehicle)-controlled in design. The studies used a modified Ora-Conjunctival Allergen Challenge (Ora-CAC®) model. Key inclusion criteria were a history of allergic conjunctivitis, a positive skin test to season and/or perennial allergens and bilateral CAC reaction. All four allergic conjunctivitis trials enrolled adult subjects (>18 years of age) of either sex. An overview of these studies is provided in Table 4.1.

TABLE 4.1

Characteristics of clinical efficacy in allergic conjunctivitis trials

| Study[c, d, e, f] | Start[a]/ Status/ Total Enrolled[b]/ Enrollment Goal | Study Control and Drugs Dose and Regimen | No. of Subjects by Arm Planned/ Entered[b]/ Completed | Gender Mean Age (range) | Diagnosis Inclusion Criteria | Primary Endpoints |
|---|---|---|---|---|---|---|
| | | | Phase II | | | |
| Study 1 | March 2014/ completed/ 35 enrolled/ 30 planned | DEXTENZA (dexamethasone ophthalmic insert) 0.4 mg | 30/35/28 | 18F, 17M 43.1 yrs (20-69 yrs) | ≥18 years with chronic allergic conjunctivitis | Ocular itching |
| | | PV (no drug punctum plug) | 30/33/31 | 17F, 16M 45.5 yrs (21-71 yrs) | | Conjunctival redness |
| | | | Phase III | | | |
| Study 2 | April 2015/ completed/ 73 enrolled/ 72 planned | DEXTENZA (dexamethasone insert) 0.4 mg | 36/35/33 | 17F, 18M 38.2 yrs (19-66 yrs) | ≥18 years with chronic allergic conjunctivitis | Ocular itching |
| | | PV (no drug punctum plug) | 36/38/37 | 44F, 39M 69.9 yrs (46-93 yrs) | | Conjunctival redness |
| Study 3 | June 2015/ completed/ 86 enrolled/ 72 planned | DEXTENZA (dexamethasone insert) 0.4 mg | 36/44/41 | 26F, 18M 39.1 yrs (20-68 yrs) | ≥18 years with chronic allergic conjunctivitis | Ocular itching |
| | | PV (no drug punctum plug) | 36/42/40 | 25F, 171M 42.2 yrs (18-70 yrs) | | |
| Study 4 | August 2019/ completed/ 96 enrolled/ 80 planned | DEXTENZA (dexamethasone insert) 0.4 mg | 40/48/44 | 27F, 21M 43.8 yrs (20-67 yrs) | ≥18 years with chronic allergic conjunctivitis | Ocular itching |
| | | PV (no drug punctum plug) | 40/48/43 | 24F, 24M 46.0 yrs (24-74 yrs) | | |

[a] first subject consented

[b] number of subjects randomized

[c] the duration of Study 1, Study 2 and Study 3 was 30 days based on preclinical studies; the duration of Study 4 was 14 days based on preclinical studies

[d] all studies were performed in the USA; Study 1-2 study centers; Study 2-4 study centers; Study 3-5 study centers; Study 4-6 study centers

[e] the design and control ty pe of each study was a prospective, randomized, double-masked, vehicle-controlled, parallel group

[f] the objective of each study was safety and efficacy of DEXTENZA for ocular itching and conjunctival redness due to allergic conjunctivitis yrs = years;

M = male;

F = female

Subject Populations, Allergic Conjunctivitis

A by-study overview of the subject demographics for each of the four trials for the treatment of ocular itching is provided in Table 4.2. The demographics were generally similar across all studies except that Study 3 had far fewer subjects that were Black as compared with the other studies. Additionally, the subject demographics in these studies were representative of the intended target population for DEXTENZA. To date, the drug product has been evaluated in adults and the elderly; however, the safety of the drug product is being evaluated in pediatric subjects undergoing cataract surgery in an ongoing clinical study in accordance with an agreed upon Pediatric Study Plan.

Study Design Features. Allergic Conjunctivitis

All four safety and efficacy studies were prospective, multicenter, double-masked, vehicle-controlled trials with a 1:1 randomization to DEXTENZA or PV.

All four studies utilized a modified Conjunctival Allergen Challenge Model (CAC® 1) for the assessment of efficacy. The CAC model controls for both environmental factors and inter-subject allergic sensitivity differences by challenging the subject with the specific type of allergen and concentration of allergen required to induce a reproducible acute allergic reaction for that individual. The clinical studies enrolled a population of subjects exhibiting an allergic response to a variety of seasonal and perennial allergens.

TABLE 4.2

Demographics of subjects in the allergic conjunctivitis efficacy trials with DEXTENZA, by study (ITT population)

| | | Phase II Study | | Phase III Studies | | |
|---|---|---|---|---|---|---|
| | | Study 1 | | Study 2 | | Study 3 |
| Demographic Characteristic | | DEXTENZA N = 35 | PV N = 33 | DEXTENZA N = 35 | PV N = 38 | DEXTENZA N = 44 |
| Race n (%) | American Indian/Alaska Native | 1 (2.9%) | 0 | 0 | 0 | 0 |
| | Asian | 0 | 0 | 13 (37.1%) | 11 (28.9%) | 2 (4.5%) |
| | Black or African American | 7 (20.0%) | 7 (21.2%) | 10 (28.6%) | 9 (23.7%) | 7 (15.9%) |
| | White | 24 (68.6%) | 24 (72.7%) | 10 (28.6%) | 12 (31.6%) | 35 (79.5%) |
| | Other | 3 (8.6%) | 2 (6.1%) | 2 (5.7%) | 6 (15.8%) | 0 |
| Age (yrs) | Mean (SD) | 43.1 (13.06) | 45.5 (12.94) | 38.2 (11.60) | 16.3 (12.01) | 39.1 (13.14) |
| | Min., Max. | 20, 69 | 21, 71 | 19, 66 | 18, 62 | 20, 68 |
| Sex n (%) | Male | 17 (48.6%) | 16 (48.5%) | 18 (51.4%) | 24 (63.2%) | 18 (40.9%) |
| | Female | 18 (51.4%) | 17 (51.5%) | 17 (48.6%) | 14 (36.8%) | 26 (59.1%) |
| Iris Color n (%) | Black | 0 | 4 (6.1%) | 0 | 0 | 2 (2.3%) |
| | Blue | 22 (31.4%) | 16 (24.2%) | 8 (11.4%) | 2 (2.6%) | 12 (13.6%) |
| | Brown | 32 (45.7%) | 32 (48.5%) | 52 (74.3%) | 64 (84.2%) | 48 (54.5%) |
| | Hazel | 6 (8.6%) | 12 (18.2%) | 2 (2.9%) | 0 | 10 (11.4%) |
| | Green | 10 (14.3%) | 2 (3.0%) | 8 (11.4%) | 10 (13.2%) | 16 (18.2%) |

| | | Phase III Studies | | |
|---|---|---|---|---|
| | | Study 3 | Study 4 | |
| Demographic Characteristic | | PV N = 42 | DEXTENZA N = 48 | PV N = 48 |
| Race n (%) | American Indian/Alaska Native | 0 | 0 | 0 |
| | Asian | 0 | 0 | 1 (2.1%) |
| | Black or African American | 2 (4.8%) | 14 (29.2%) | 17 (35.4%) |
| | White | 40 (95.2%) | 32 (66.7%) | 29 (60.4%) |
| | Other | 0 | 2 (4.2%) | 1 (2.1%) |
| Age (yrs) | Mean (SD) | 42.2 (13.47) | 43.8 (12.45) | 46.0 (12.92) |
| | Min., Max. | 18, 70 | 20, 67 | 24, 74 |
| Sex n (%) | Male | 17 (40.5%) | 21 (43.8%) | 24 (50.0%) |
| | Female | 25 (59.5%) | 27 (56.3%) | 24 (50.0%) |
| Iris Color n (%) | Black | 0 | 0 | 0 |
| | Blue | 30 (35.7%) | 11 (22.9%) [a] | 11 (22.9%) |
| | Brown | 38 (45.2%) | 25 (52.1%) [a] | 32 (66.7%) |
| | Hazel | 6 (7.1%) | 6 (12.5%) | 0 |
| | Green | 10 (11.9%) | 6 (12.5%) | 5 (10.4%) |

[a] One subject in the DEXTENZA arm of Study 4 had two different eye colors: blue right eye and brown left eye. The numbers in this table represent data from the right eye. Accordingly, in the left eye, the total numbers were: blue eye n = 10 (20.8%), and brown n = 26 (54.2%)

The CAC model has been used to evaluate anti-allergic agents and to identify the cellular and mediator responses seen in allergic conjunctivitis (Abelson, et al., *Conjunctival allergen challenge: A clinical approach to studying allergic conjunctivitis*, Arch Opthalmol 108: 84-88 (1990)) (hereinafter referred to as "Abelson 1990"). In addition, the CAC model has been clinically validated and has been recognized by the FDA as a reliable method for evaluating novel ophthalmic pharmaceutical drugs (Abelson 1990; Abelson and Loeffler 2003). Since changes in the signs and symptoms of ocular allergy are captured on standardized severity scales, the CAC model allows for precise comparisons of the effects of ocular allergy drugs among study subjects with a high level of internal control, sensitivity, and reproducibility.

The modified CAC model used in the studies with DEXTENZA were designed with regard to the mechanism of action of the anti-inflammatory properties of steroids. Rather than using a single challenge, these studies used a series of three (3) to four (4) challenges over 2-3 days to repeatedly induce an allergic response in each subject. Repeated exposure to allergen challenge induces the late phase allergic inflammation in addition to the acute antihistamine responses. The studies were conducted based on the hypothesis that the anti-inflammatory effect of a steroid would suppress the overall immune response to subsequent allergen challenges.

The PEG hydrogel acts as the delivery platform and is formed as an intracanalicular depot to secure DEXTENZA in the canaliculus. The intracanalicular depot is designed to stay in the canaliculus for at least 30 days to ensure retention through drug delivery. Over this time and through hydrolysis, DEXTENZA softens, liquefies and is cleared through the nasolacrimal duct. The fluorescein in the intracanalicular depot illuminates when excited with a blue light source to provide confirmation of product presence.

The PV used in all four trials was the same fluorescent PEG hydrogel as DEXTENZA, except that it lacked the active ingredient dexamethasone. The PV is the most appropriate control for this trial in order to maintain masking.

DEXTENZA and the PV were identical in appearance and supplied in identical packages that met regulatory requirements for study treatments.

For all studies, the initial titration CAC was completed within approximately 5 days prior to insertion of the test article to assess safety and allergic response. Two subsequent confirmatory CAC allergen challenges were completed approximately 4 days prior to the insertion of the test article.

Subject Inclusion/Exclusion Criteria, Allergic Conjunctivitis

Inclusion criteria for all four trials were similar. Subjects in all four trials were adults ≥18 years of age and were required to have a positive history of ocular allergies and a positive skin test reaction to a perennial allergen (cat dander, dog dander, dust mites, cockroaches) and a seasonal allergen (trees, grasses, and/or ragweed) as confirmed by the allergic skin test. Subjects were to have a positive bilateral CAC reaction (i.e., scores of ≥2 for itching and ≥2 conjunctival redness) to a qualifying allergen within 10 (±2) minutes of instillation of the last titration of allergen, a positive bilateral CAC reaction for at least two out of the three time points following a challenge, and an average of ≥3 itching and ≥2.5 conjunctival redness for both eyes at post-CAC assessments for the Phase III studies and an average ≥2 itching and ≥2 conjunctival redness for the Phase II study.

The exclusion criteria for the four trials were similar and designed to exclude individuals with coexisting ocular conditions that would place them at risk from participating in the trial, individuals for whom the use of a corticosteroid was contraindicated, those for whom an intracanalicular insert was not appropriate, as well as individuals with ocular conditions or those using ocular or systemic medications that would interfere with the assessment of safety and/or efficacy of DEXTENZA.

Other exclusions in all four studies included subjects using ocular or systemic anti-inflammatory or immunomodulating agents, as well as a systemic dose of a NSAID for the duration of the study. Specific prohibited medications included systemic or ocular antihistamines, decongestants, monoamine oxidase inhibitors, topical ophthalmic preparations, lid scrubs, prostaglandins, and any corticosteroids other than the study medication.

Efficacy Endpoints, Allergic Conjunctivitis

All four trials had a primary efficacy endpoint of ocular itching; however, two of the studies (Study 1 and Study 2) also included a co-primary endpoint of conjunctival redness.

The primary efficacy endpoint for the three Phase III trials (Study 2, Study 3, and Study 4) was ocular itching evaluated by the subject after a series of closely spaced CACs on Day 8 (7 days post-insertion). For Study 1 (Phase II), the primary endpoint for ocular itching evaluated by the subject was on Day 15 (14 days post-insertion).

Scales

The scales for the subject-evaluation symptoms (primary and secondary endpoints) were identical in all four trials as follows:

Subject-Evaluated Ocular Symptoms

Itching (Ora Calibra™ Conjunctival Allergen Challenge Ocular Itching Scale):
- 0=None
- 0.5=An intermittent tickle sensation possibly localized in the corner of the eye
- 1.0=An intermittent tickle sensation involving more than just the corner of the eye
- 1.5=An intermittent all-over tickling sensation
- 2.0=A mild continuous itch (can be localized) without desire to rub
- 2.5=A moderate, diffuse continuous itch with desire to rub
- 3.0=A severe itch with desire to rub
- 3.5=A severe itch improved with minimal rubbing
- 4.0=An incapacitating itch with an irresistible urge to rub
- 0.5 unit increments WERE allowed Eyelid Swelling (Ora Calibra™ Conjunctival Allergen Challenge Eyelid Swelling Scale):
- 0=None
- 1.0=Mild—Detectable swelling of lower and/or upper lid
- 2.0=Moderate—Definite swelling of lower and/or upper lid
- 3.0=Severe—Swelling of lower and/or upper lid to the point that there is a decrease in the space between your upper and lower lids
- 0.5 unit increments were NOT allowed Tearing/Watery Eyes (Ora Calibra™ Conjunctival Allergen Challenge Tearing/Watery Eyes Scale):
- 0=None/Normal
- 1=Mild—A noticeably increased moistening of your eye
- 2=Moderate—Your eye feels "full" of water; your lashes feel a little wet
- 3=Severe—Feels like tears might drip down your face; very wet lashes
- 4=Very Severe—Tears are dripping down your face
- 0.5 increments were NOT allowed Subject-Evaluated Nasal Symptoms Rhinorrhea (Runny Nose) (Ora Calibra™ Rhinorrhea Scale):
  0=None
  1=Mild (sensation of nasal mucus flowing down nasal passage; no discharge present)
  2=Moderate (may be associated with post nasal drip; nasal mucus flow more pronounced; will need to blow nose soon)
  3=Moderate/Severe (nasal mucus discharge requiring occasional wiping with Kleenex)
  4=Severe (uncontrolled nasal discharge; requiring frequent wiping and blowing nose)
  0.5 unit increments were NOT allowed.

Nasal Pruritus (Itchy Nose) (Ora Calibra™ Nasal Pruritus Scale):
  0=None
  1=Mild (An intermittent tickle sensation)
  2=Moderate (A mild continuous itch)
  3=Moderate/Severe (A severe itch with desire to rub)
  4=Severe (Incapacitating itch with an irresistible urge to rub)
  0.5 unit increments were NOT allowed.

Ear or Palate Pruritus (Itchy Ear or Palate) (Ora Calibra™ Ear or Palate Pruritus Scale):
  0=None
  1=Mild (An intermittent tickle sensation)
  2=Moderate (A mild continuous itch)
  3=Moderate/Severe (A severe itch with desire to nib)
  4=Severe (Incapacitating itch with an irresistible urge to rub)
  0.5 unit increments were NOT allowed.

Nasal Congestion (Ora Calibra™ Nasal Congestion Scale):
  0=None (No breathing difficulty)
  1=Mild (Some sensation of blockage)
  2=Moderate (Partial Blockage)
  3=Moderate/Severe (Significant blockage but can still breathe through nose)
  4=Severe (Cannot breathe through nose at all)
  0.5 unit increments were NOT allowed.

Investigator-Evaluated Ocular Signs

Regional Redness (Ora Calibra™ Ocular Hyperemia Scale):
  Hyperemia (ciliary, conjunctival, and episcleral) evaluated separately with a slit lamp
  0=None
  1=Mild—Slightly dilated blood vessels; color of vessels is typically pink; can be quadrantal
  2=Moderate—More apparent dilation of blood vessels; vessel color is more intense (redder); involves the majority of the vessel bed
  3=Severe—Numerous and obvious dilated blood vessels; in the absence of chemosis the color is deep red, may be less red or pink in presence of chemosis, is not quadrantic
  4=Extremely Severe—Large, numerous, dilated blood vessels characterized by unusually severe deep red color, regardless of grade of chemosis, which involves the entire vessel bed
  0.5 unit increments WERE allowed Chemosis (Ora Calibra™ Chemosis Scale):
  0=None
  1.0=Detectable only by slit lamp beam; definite separation of conjunctiva from sclera
  2.0=Visible in normal room light; more diffuse edema
  3.0=Conjunctival billowing at the limbus; very diffuse and noticeable
  4.0=Severe overall billowing of conjunctiva
  0.5 unit increments WERE allowed Study Visits Efficacy and safety assessment visits were similar among the three Phase III studies (Table 4.3). For these studies, after the initial screening period of approximately 40 days, subjects were rescreened within 5 days prior to insertion of the test article for a confirmatory CAC allergen challenge and safety assessments. Studies Study 2 and Study 3 were identical in their study designs. These studies included 12 study visits over 4 weeks with 3 post-CAC times (3, 5 and 7 min) at each visit. Study 4 included 6 visits over 2 weeks with 4 post-CAC times (3, 5, 7 and 10 min) at each visit that included an additional 10-min timepoint at each visit, plus a 30-day follow-up visit. The primary analysis visit for all 3 Phase III studies was Day 8 (7 days after insertion) at 3, 5 and 7 min post-CAC.

The study visit schedule for the Phase II Study 1 was generally similar to those for the Phase III studies (Table 4.3). It included 12 study visits over 6 weeks that included 3 post-CAC times (3, 5 and 7 min) at each visit; however, the primary analysis visit for the Phase II study was Day 15 (14 days after insertion). This study did not include a study visit on Day 8 (the primary analysis visit for the other studies) and thus was not included in the pooled analyses.

TABLE 4.3

Schedule of visits for efficacy and safety assessments in phase 3 studies

| | Visits | | | | | | | | |
| --- | --- | --- | --- | --- | --- | --- | --- | --- | --- |
| | S | V1 | V2a | V2b | V3a | V3b | V4 | V5a | V5b | V6[a] |
| | | | | | Days | | | | | |
| Study No. | −45 to −6 | −5 + 1 | −4 + 1 | −4 + 1; 8 h post-V2a | −3 + 1 | 1 | 6 | 7 | 7; 8 h post-V5a | 8 |
| Study 2 | X | X | X | X | X | X | X | X | X | X |
| Study 3 | X | X | X | X | X | X | X | X | X | X |
| Study 4 [b] | X | X | X | X | X | X | | X | X | X |
| | V1 | V2 | V3a | V3b | V4a | V4b | | V5 | V6a | V6b |
| | −45 to −6 | −5 + 1 | −4 + 1 | V3a + 8 h | V3a + 24 h | 1 | | 7 | 8 | V6a + 8 h |

TABLE 4.3-continued

Schedule of visits for efficacy and safety assessments in phase 3 studies

| | Visits | | | | | | | |
|---|---|---|---|---|---|---|---|---|
| | V7 | V8a | V8b | V9 | V10 | V11a | V11b | V12 |
| | | | | | Days | | | |
| Study No. | 13 | 14 | 14; 8 h post-V8a | 15 | 26-29 | 27-30 | 27-30; 8 h post-V11a | 28-31 |
| Study 2 | X | X | X | X | X | X | X | X |
| Study 3 | X | X | X | X | X | X | X | X |
| Study 4 [b] | | X | X | X | | | | X |
| | | V7 | V8a | V8b | | | | V9 |
| | | 14 | 15 | 15; V8a + 8 h | | | | 30 + 3 |

S = Screening;
V = Visit
[a] Primary endpoint
[b] The schedule for Study 4 has been organized to show visits and days corresponding to the other 2 trials.

TABLE 4.4

Schedule of Visits for Efficacy and Safety Assessments in the Phase II Study 1

| Visit | V1 | V2a | V2b | V3a | V3b | V4 | V5a | V5b | V6 [a] |
|---|---|---|---|---|---|---|---|---|---|
| Days | −5 + 1 | −4 + 1 | −4 + 1 | −3 + 1 | 1 | 13 | 14 | 14 | 15 |
| Visit | V7 | V8a | V8b | V9 | V10 | V11a | V11b | V12 | |
| Days | 26 (+7) | 27 (V7 + 1) | 27 (V8a + 8 hrs) | 28 (V8a + 24 hrs) | 40 (+7) | 41 (V10 + 1) | 41 (V11a + 8 hrs) | 42 (V11a + 24 hrs) | |

V = Visit
[a] Primary endpoint

Data Analysis
Ocular Itching

The statistical objective for each of the four studies was to demonstrate statistical superiority of DEXTENZA over PV for ocular itching at multiple time points after CAC. Clinical meaningfulness was defined as at least 0.5 units of a 5 point scale for all 3 post-CAC times (3, 5, and 7 min) and at least 1 unit for the majority of the post-CAC time points.

For the Phase III studies, Markov Chain Monte Carlo (MCMC) methods were employed to impute missing primary efficacy data for the ITT population. A separate model was fit for each time point. The model included variables for treatment, baseline measure and response measure. For the Phase II study (Study 1) the data for the primary efficacy endpoint were analyzed using ITT with LOCF.

Additional imputation methods, including LOCF, were performed as sensitivity analyses to the primary efficacy analyses.

Conjunctival Redness

The statistical objective for conjunctival redness for studies Study 1 and Study 2 was to demonstrate clinical superiority of DEXTENZA over PV at multiple time points after CAC. Clinical meaningfulness was defined as at least 0.5 units of a 5 point scale for all 3 post-CAC time points (7, 15, 20 min) and at least 1 unit for the majority of the post-CAC time points.

For Study 2 MCMC methods were employed to impute missing primary efficacy data for the ITT population. A separate model was fit for each time point. The model included variables for treatment, baseline measure and response measure. For the Phase II study (Study 1) the data for the primary efficacy endpoint were analyzed using ITT with LOCF.

Figure 9:
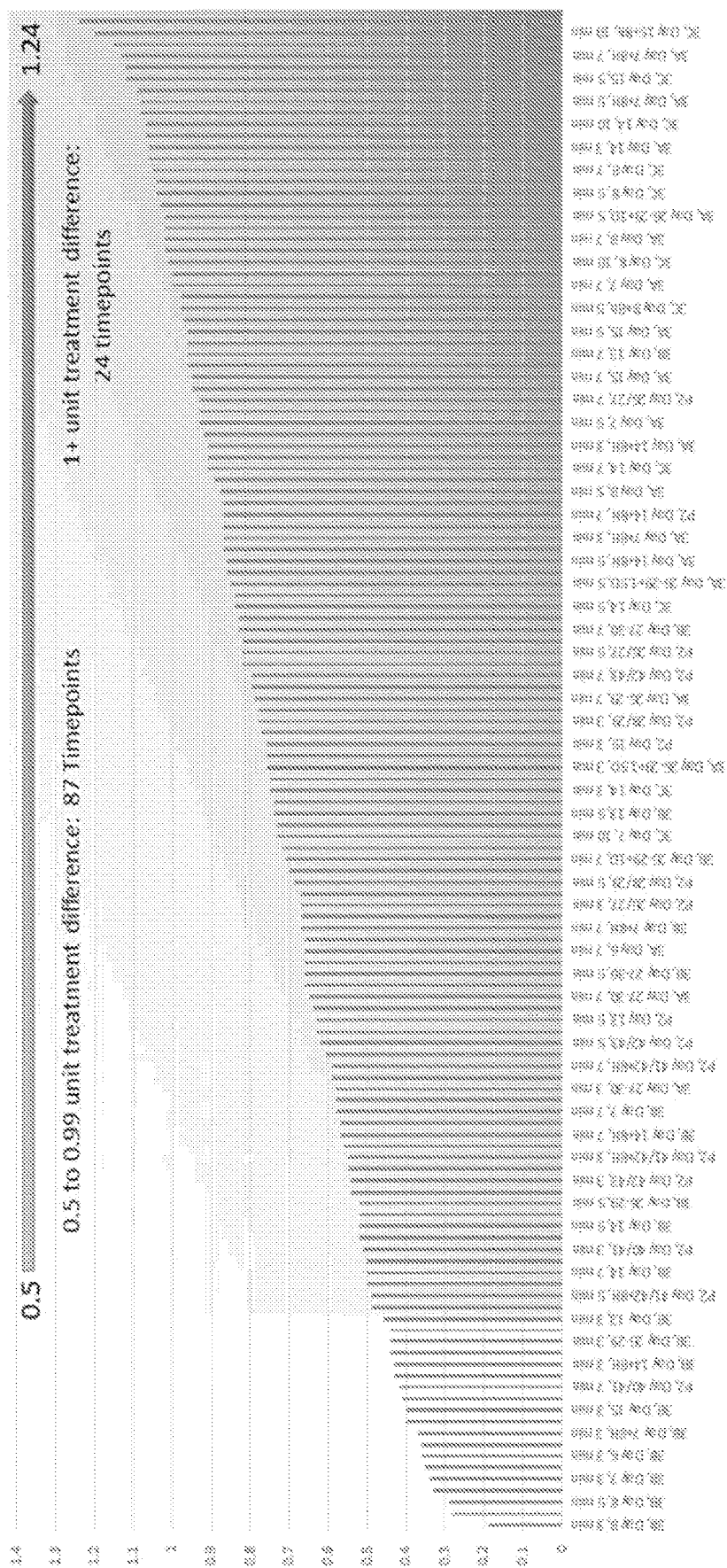
FIG. 9 shows treatment differences (in favor of DEX-TENZA) in mean ocular itching scores by unit in ascending order across all study visits—All studies relating to allergic conjunctivitis.

Efficacy Results in All Allergic Conjunctivitis Studies
Primary Efficacy Endpoints, Allergic Conjunctivitis Across all four studies DEXTENZA treatment consistently resulted in lower ocular itching scores relative to PV at all study visits through the duration of the study. In three of the four studies (Phase II Study 1, Phase III studies Study 2 and Study 4), there were statistically significant treatment differences for the primary endpoint in favor of DEXTENZA at all 3 post-CAC time points at the primary endpoint visit (Table 4.5). In addition, all differences fur the primary endpoint visit for these three studies in favor of DEXTENZA were >0.5 unit and many differences were >1.0 unit (FIG. 9).

Even in Study 3 DEXTENZA treatment resulted in lower mean ocular itching scores compared with PV at all time-points throughout the one-month duration of the study. Overall, similar results were found with all analysis populations, which highlights the consistency of the data across analysis methods.

Allergic conjunctivitis is a variable disease that has the potential to result in inconsistencies in the outcome of clinical trials. Unlike the other three studies, Study 3 took a longer time to complete, spanned different allergy seasons and included fewer Black subjects relative to the other studies.

magnitude of the DEXTENZA effects on ocular itching was lower than that observed for individual studies due to the inclusion of results from Study 3.

TABLE 4.5

Primary endpoint for ocular itching by study - all analysis populations

| Time | | | Least Square Means | | | | |
|---|---|---|---|---|---|---|---|
| Post-CAC | Study Population | | DEXTENZA | PV | Diff | 95% CI | p-value[a] |
| Phase II | | | Study 1-Day 15 (14 days post-insertion) | | | | |
| Study | | ITT Analysis Population (n) | 35 | 33 | | | |
| | | PP Analysis Population (n) | 28 | 31 | | | |
| | 3 min | ITT, LOCF | 1.81 | 2.57 | −0.76 | (−1.26, −0.27) | 0.0030 |
| | | ITT, MCMC | 1.75 | 2.58 | −0.83 | (−1.29, −0.37) | 0.0004 |
| | | ITT, Observed Data | 1.81 | 2.57 | −0.76 | (−1.26, −0.27) | 0.0030 |
| | | PP, Observed Data | 1.81 | 2.57 | −0.76 | (−1.26, −0.27) | 0.0030 |
| | 5 min | ITT, LOCF | 1.73 | 2.70 | −0.97 | (−1.45, −0.50) | 0.0001 |
| | | ITT, MCMC | 1.71 | 2.73 | −1.01 | (−1.52, −0.51) | 0.0001 |
| | | ITT, Observed Data | 1.73 | 2.70 | −0.97 | (−1.45, −0.50) | 0.0001 |
| | | PP, Observed Data | 1.73 | 2.70 | −0.97 | (−1.45, −0.50) | 0.0001 |
| | 7 min | ITT, LOCF | 1.66 | 2.53 | −0.87 | (−1.36, −0.38) | 0.0007 |
| | | ITT, MCMC | 1.68 | 2.51 | −0.83 | (−1.36, −0.30) | 0.0030 |
| | | ITT, Observed Data | 1.66 | 2.53 | −0.87 | (−1.36, −0.38) | 0.0007 |
| | | PP, Observed Data | 1.66 | 2.53 | −0.87 | (−1.36, −0.38) | 0.0007 |
| Phase III | | | Study 2-Day 8 (7 days post-insertion) | | | | |
| Studies | | ITT Analysis Population (n) | 35 | 38 | | | |
| | | PP Analysis Population (n) | 30 | 36 | | | |
| | 3 min | ITT, MCMC | 1.71 | 2.62 | −0.91 | (−1.40, −0.41) | 0.0004 |
| | | ITT, Observed Data | 1.69 | 2.64 | −0.95 | (−1.46, −0.44) | 0.0004 |
| | | PP, Observed Data | 1.66 | 2.64 | −0.99 | (−1.50, −0.47) | 0.0003 |
| | 5 min | ITT, MCMC | 1.90 | 2.77 | −0.87 | (−1.35, −0.38) | 0.0006 |
| | | ITT, Observed Data | 1.88 | 2.76 | −0.88 | (−1.35, −0.41) | 0.0004 |
| | | PP, Observed Data | 1.88 | 2.76 | −0.89 | (−1.36, −0.41) | 0.0005 |
| | 7 min | ITT, MCMC | 1.78 | 2.78 | −1.00 | (−1.41, −0.59) | <0.0001 |
| | | ITT, Observed Data | 1.72 | 2.73 | −1.02 | (−1.46, −0.57) | <0.0001 |
| | | PP, Observed Data | 1.72 | 2.73 | −1.02 | (−1.46, −0.57) | <0.0001 |
| | | | Study 3-Day 8 (7 days post-insertion) | | | | |
| | | ITT Analysis Population (n) | 44 | 42 | | | |
| | | PP Analysis Population (n) | 40 | 38 | | | |
| | 3 min | ITT, MCMC | 2.06 | 2.31 | −0.24 | (−0.74, 0.25) | 0.3363 |
| | | ITT, Observed Data | 2.08 | 2.27 | −0.19 | (−0.72, 0.35) | 0.4888 |
| | | PP, Observed Data | 2.08 | 2.27 | −0.19 | (−0.72, 0.35) | 0.4888 |
| | 5 min | ITT, MCMC | 2.07 | 2.36 | −0.29 | (−0.79, 0.21) | 0.2593 |
| | | ITT, Observed Data | 2.10 | 2.39 | −0.29 | (−0.84, 0.26) | 0.2927 |
| | | PP, Observed Data | 2.10 | 2.39 | −0.29 | (−0.84, 0.26) | 0.2927 |
| | 7 min | ITT, MCMC | 2.06 | 2.31 | −0.25 | (−0.79, 0.29) | 0.3610 |
| | | ITT, Observed Data | 2.05 | 2.38 | −0.33 | (−0.93, 0.27) | 0.2730 |
| | | PP, Observed Data | 2.05 | 2.38 | −0.33 | (−0.93, 0.27) | 0.2730 |
| | | | Study 4-Day 8 (7 days post-insertion) | | | | |
| | | ITT Analysis Population (n) | 48 | 48 | | | |
| | | PP Analysis Population (n) | 45 | 41 | | | |
| | 3 min | ITT, MCMC | 1.82 | 2.67 | −0.86 | (−1.25, −0.46) | <0.0001 |
| | | ITT, Observed Data | 1.81 | 2.68 | −0.87 | (−1.28, −0.46) | <0.0001 |
| | | PP, Observed Data | 1.79 | 2.66 | −0.87 | (−1.29, −0.45) | <0.0001 |
| | 5 min | ITT, MCMC | 1.73 | 2.71 | −0.98 | (−1.37, −0.59) | <0.0001 |
| | | ITT, Observed Data | 1.74 | 2.73 | −0.99 | (−1.40, −0.59) | <0.0001 |
| | | PP, Observed Data | 1.74 | 2.72 | −0.98 | (−1.40, −0.55) | <0.0001 |
| | 7 min | ITT, MCMC | 1.74 | 2.69 | −0.96 | (−1.35, −0.56) | <0.0001 |
| | | ITT, Observed Data | 1.73 | 2.69 | −0.97 | (−1.37, −0.56) | <0.0001 |
| | | PP, Observed Data | 1.73 | 2.69 | −0.96 | (−1.37, −0.54) | <0.0001 |

[a] p-value calculated using an analysis of covariance (ANCOVA) model with treatment and baseline comparing DEXTENZA and PV.

Bold p-values indicate statistical significance

Analysis of the pooled data from the three Phase III studies showed that on Day 8 (7 days post-insertion) there were statistically significant treatment differences in ocular itching in favor of DEXTENZA with a p<0.0001 at all 3 post-CAC timepoints (Table 4.6). The treatment differences at all timepoints were ≥0.5 unit. In the pooled analysis, the Similar results were found in all analysis populations and imputation methods highlighting the consistency of the data across analysis methods.

Figure 10A:
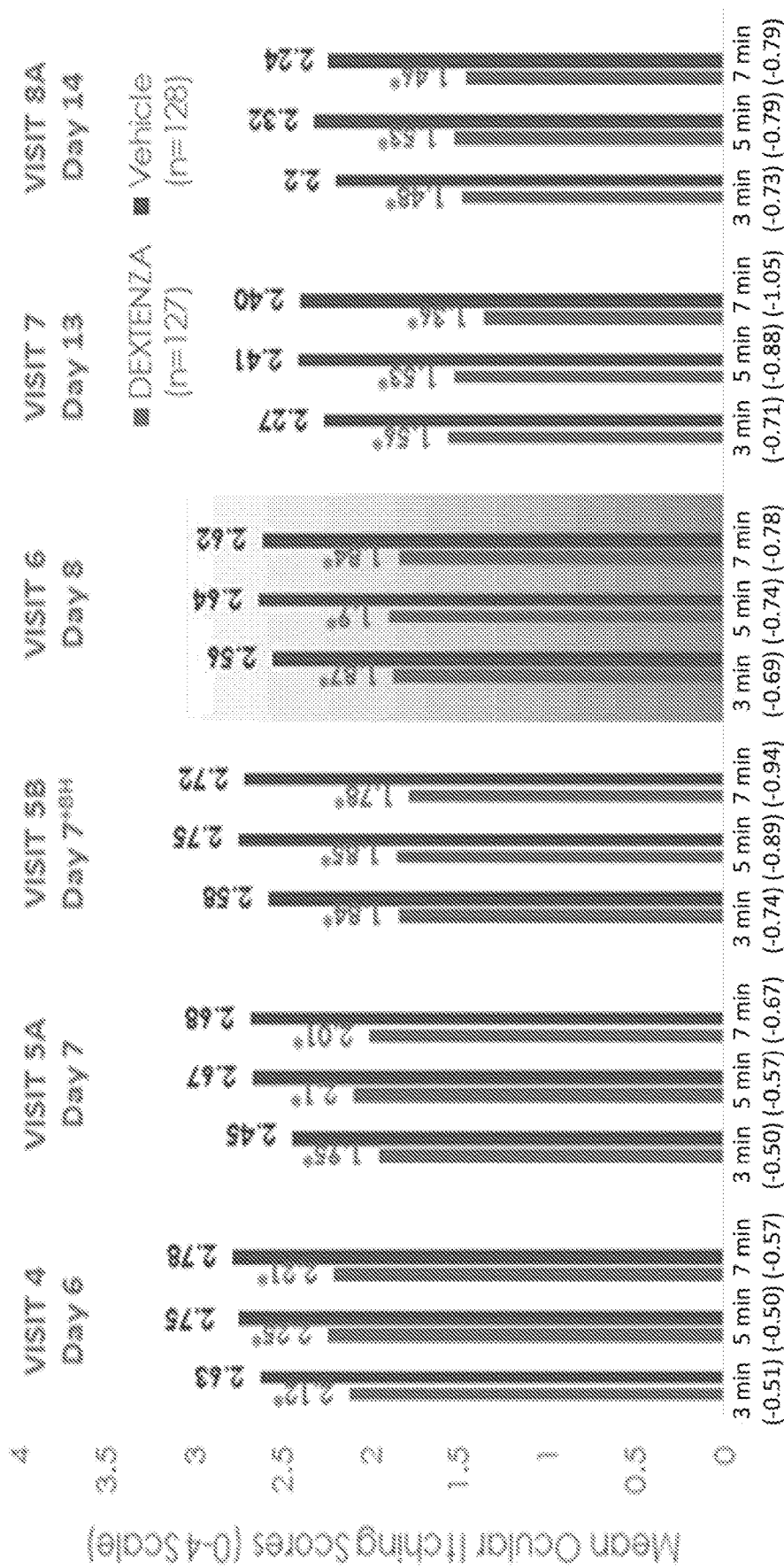
FIGS. 10A and 10B show pooled least square means and treatment differences for ocular itching scores across all visits for Phase III studies relating to allergic conjunctivitis: (10A) Day 6-Day 14; (10B) Day 14-Day 31.
Figure 10B:
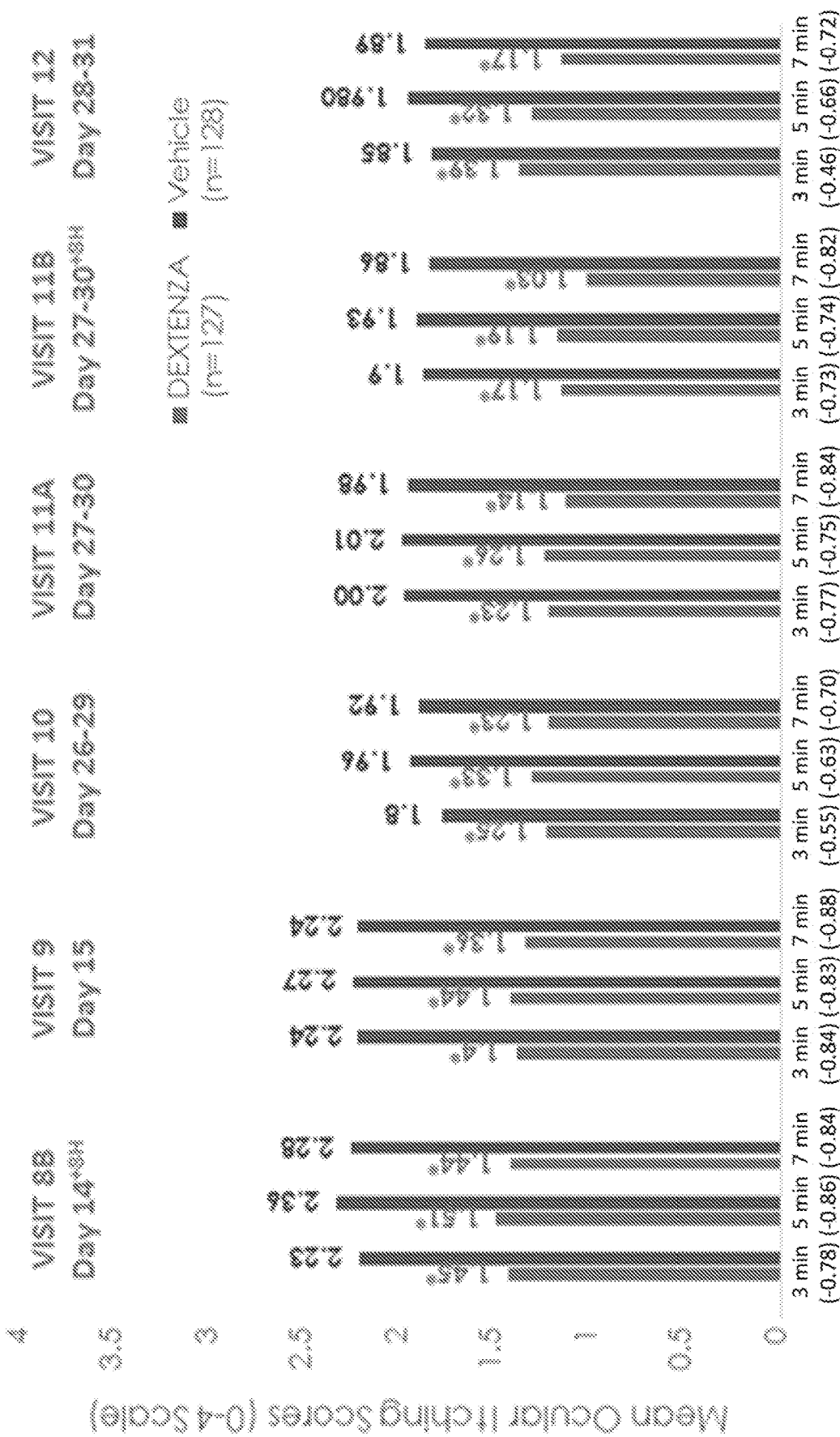

Based on analysis of pooled data across all study visits, DEXTENZA treatment resulted in ≥0.5 unit difference compared with PV at all study visits and 35 out of 36 CAC assessment times (FIGS. 10A, 10B). In FIGS. 10A and 10B, p<0.05 and the data presented are intent to treat (ITT) with observed data. The shaded area shows the results of the sensitivity analysis of the primary endpoint.

TABLE 4.6

Primary endpoint pooled analysis of ocular itching on Day 8 (all analysis populations)

| Time Post-CAC | Study Population | Least Square Means DEXTENZA | PV | Diff | 95% CI | p-value |
|---|---|---|---|---|---|---|
| | ITT Analysis Population | 127 | 128 | | | |
| | PP Analysis Population | 115 | 115 | | | |
| 3 min | ITT, MCMC | 1.87 | 2.54 | −0.67 | (−0.93, −0.40) | <0.0001 |
| | ITT, Observed Data | 1.87 | 2.56 | −0.69 | (−0.96, −0.41) | <0.0001 |
| | PP, Observed Data | 1.85 | 2.55 | −0.69 | (−0.97, −0.41) | <0.0001 |
| | ITT, PMM | 1.93 | 2.54 | −0.60 | (−0.86, −0.34) | <0.0001 |
| 5 min | ITT, MCMC | 1.90 | 2.63 | −0.73 | (−0.99, −0.47) | <0.0001 |
| | ITT, Observed Data | 1.90 | 2.64 | −0.74 | (−1.01, −0.47) | <0.0001 |
| | PP, Observed Data | 1.90 | 2.63 | −0.73 | (−1.01, −0.46) | <0.0001 |
| | ITT, PMM | 1.96 | 2.63 | −0.67 | (−0.93, −0.40) | <0.0001 |
| 7 min | ITT, MCMC | 1.85 | 2.59 | −0.74 | (−1.01, −0.47) | <0.0001 |
| | ITT, Observed Data | 1.84 | 2.62 | −0.78 | (−1.05, −0.51) | <0.0001 |
| | PP, Observed Data | 1.84 | 2.61 | −0.77 | (−1.05, −0.49) | <0.0001 |
| | ITT, PMM | 1.91 | 2.60 | −0.69 | (−0.95, −0.42) | <0.0001 |

Bold p-values indicate statistical significance
ITT = intent to treat;
MCMC = Markov Chain Monte Carlo;
PMM = pattern mixture modeling;
PP = per protocol Analysis of Subpopulations for Ocular Itching—Pooled Data of Phase III Studies Due to the limited size of many of the subpopulations in the individual trials, no efficacy analyses were performed on subpopulations within each trial; however, an analysis of efficacy on Day 8 for subpopulations pooled across all three Phase III trials was conducted by age category (18-40 years; 41-60 years; 61-75 years), by sex (male; female), by race (Asian; Black or African American; White), by ethnicity (Hispanic or Latino; not Hispanic or Latino), and by iris color (blue; not blue).

Analysis of pooled data by sex indicated statistically significant differences in ocular itching in favor of DEXTENZA in both males and females at all 3 post-CAC timepoints. Compared with males, females had lower mean ocular itching scores and showed greater differences between DEXTENZA and PV treatment groups.

Analysis of pooled data by age indicated statistically significant differences in ocular itching in favor of DEXTENZA in age groups ≥60 years at all 3 post-CAC timepoints with differences that were all ≥0.5 unit. In individuals 61-75 years of age, the differences in ocular itching between the treatment arms were also in favor of DEXTENZA, but were not statistically significant due to the small number of subjects (8%, 21 of 255) in this age group.

In the analysis of pooled data by race, there were statistically significant differences in favor of DEXTENZA in the race categories of Black and White with all differences being ≥0.5 unit. The treatment differences in favor of DEXTENZA in Black subjects were nearly 1.00 unit for ocular itching. The differences in the Asian population were statistically significant at 3 min post-CAC only due to the small number of total subjects (11%, 27 of 244) in this race category. Similarly, in the analysis of pooled data on Day 8 by ethnicity, statistically significant differences in favor of DEXTENZA were observed in the non-Hispanic/Latino population at all 3 post-CAC timepoints and not in the small group of Hispanic/Latino subjects that represented 16% (40 of 255) of total study population.

The majority of subjects in the Phase III studies had brown eyes (62%) followed by those with blue eyes (19%). Overall, on Day 8, all eye colors showed statistically significant differences in favor of DEXTENZA at all 3 post-CAC timepoints with all differences being ≤0.5 unit. Subjects with blue eyes revealed greater differences in favor of DEXTENZA that were ≥1.0 unit at 5 and 7 min post-CAC; however, this was a smaller population of subjects than for other eye colors.

Secondary Efficacy Endpoints, Allergic Conjunctivitis

Conjunctival redness was a secondary endpoint for two of the three Phase III studies (Study 3, Study 4) and was a co-primary endpoint for the Phase II Study 1 and Phase III Study 2. In all studies there were lower mean scores in conjunctival redness with DEXTENZA relative to the PV group at all visits throughout the duration of each individual study. There were statistically significant differences in favor of DEXTENZA in mean conjunctival redness scores in the Phase II Study 1 (Day 15) at all 3 post-CAC timepoints at the visit for the primary endpoint of ocular itching. In the Phase III Study 4 the differences in mean conjunctival redness scores were in favor of DEXTENZA with p-values <0.05 at all 3 post-CAC timepoints at the visit for the primary endpoint of ocular itching on Day 8. Phase III studies Study 2 and Study 3 also had differences in favor of DEXTENZA with p-values <0.05 in mean conjunctival redness scores at 20 min post-CAC on Day 8. Similar results were found with all analysis populations, highlighting the consistency of the data across analysis methods (Table 4.7)

TABLE 4.7

Conjunctival redness by study - all analysis populations[a]

| | Time Post-CAC | Study Population | Least Square Means DEXTENZA | PV | Diff | 95% CI | p-value[b] |
|---|---|---|---|---|---|---|---|
| Phase II Study | | Study 1-Day 15 (14 days post-insertion) | | | | | |
| | | ITT Analysis Population (n) | 35 | 33 | | | |
| | | PP Analysis Population (n) | 28 | 31 | | | |
| | 7 min | ITT, LOCF | 1.63 | 2.09 | −0.46 | (−0.81, −0.12) | 0.0097 |
| | | ITT, MCMC | 1.59 | 2.08 | −0.49 | (−0.81, −0.17) | 0.0024 |
| | | ITT, Observed Data | 1.63 | 2.09 | −0.46 | (−0.81, −0.12) | 0.0097 |
| | | PP, Observed Data | 1.63 | 2.09 | −0.46 | (−0.81, −0.12) | 0.0097 |
| | 15 min | ITT, LOCF | 1.55 | 2.21 | −0.66 | (−1.00, −0.32) | 0.0003 |
| | | ITT, MCMC | 1.55 | 2.23 | −0.68 | (−1.03, −0.33) | 0.0002 |
| | | ITT, Observed Data | 1.55 | 2.21 | −0.66 | (−1.00, −0.32) | 0.0003 |
| | | PP, Observed Data | 1.55 | 2.21 | −0.66 | (−1.00, −0.32) | 0.0003 |
| | 20 min | ITT, LOCF | 1.54 | 2.21 | −0.68 | (−1.01, −0.34) | 0.0002 |
| | | ITT, MCMC | 1.56 | 2.20 | −0.64 | (−1.01, −0.27) | 0.0010 |
| | | ITT, Observed Data | 1.54 | 2.21 | −0.68 | (−1.01, −0.34) | 0.0002 |
| | | PP, Observed Data | 1.54 | 2.21 | −0.68 | (−1.01, −0.34) | 0.0002 |
| Phase III Studies | | Study 2-Day 8 (7 days post-insertion) | | | | | |
| | | ITT Analysis Population (n) | 35 | 38 | | | |
| | | PP Analysis Population (n) | 30 | 36 | | | |
| | 7 min | ITT, MCMC | 1.58 | 1.76 | −0.18 | (−0.52, 0.16) | 0.2983 |
| | | ITT, Observed Data | 1.54 | 1.78 | −0.25 | (−0.58, 0.09) | 0.1448 |
| | | PP, Observed Data | 1.55 | 1.79 | −0.24 | (−0.58, 0.10) | 0.1580 |
| | 15 min | ITT, MCMC | 1.50 | 1.82 | −0.32 | (−0.65, 0.00) | 0.0534 |
| | | ITT, Observed Data | 1.47 | 1.80 | −0.33 | (−0.66, 0.01) | 0.0561 |
| | | PP, Observed Data | 1.49 | 1.80 | −0.31 | (−0.65, 0.03) | 0.0737 |
| | 20 min | ITT, MCMC | 1.38 | 1.77 | −0.39 | (−0.76, −0.03) | 0.0322 |
| | | ITT, Observed Data | 1.35 | 1.81 | −0.46 | (−0.81, −0.11) | 0.0118 |
| | | PP, Observed Data | 1.38 | 1.82 | −0.43 | (−0.79, −0.08) | 0.0185 |
| | | Study 3-Day 8 (7 days post-insertion) | | | | | |
| | | ITT Analysis Population (n) | 44 | 42 | | | |
| | | PP Analysis Population (n) | 40 | 38 | | | |
| | 7 min | ITT, Observed Data | 1.78 | 2.13 | −0.35 | (−0.73, 0.03) | 0.0725 |
| | | PP, Observed Data | 1.78 | 2.13 | −0.35 | (−0.73, 0.03) | 0.0725 |
| | 15 min | ITT, Observed Data | 1.82 | 2.21 | −0.39 | (−0.79, 0.02) | 0.0590 |
| | | PP, Observed Data | 1.82 | 2.21 | −0.39 | (−0.79, 0.02) | 0.0590 |
| | 20 min | ITT, Observed Data | 1.69 | 2.11 | −0.42 | (−0.82, −0.03) | 0.0363 |
| | | PP, Observed Data | 1.69 | 2.11 | −0.42 | (−0.82, −0.03) | 0.0363 |
| | | Study 4-Day 8 (7 days post-insertion) | | | | | |
| | | ITT Analysis Population (n) | 48 | 48 | | | |
| | | PP Analysis Population (n) | 45 | 41 | | | |
| | 7 min | ITT, Observed Data | 1.55 | 2.39 | −0.84 | (−1.15, −0.52) | <0.0001 |
| | | PP, Observed Data | 1.51 | 2.41 | −0.90 | (−1.22, −0.58) | <0.0001 |
| | 15 min | ITT, Observed Data | 1.73 | 2.59 | −0.86 | (−1.20, −0.51) | <0.0001 |
| | | PP, Observed Data | 1.69 | 2.61 | −0.92 | (−1.27, −0.57) | <0.0001 |
| | 20 min | ITT, Observed Data | 1.73 | 2.65 | −0.92 | (−1.26, −0.58) | <0.0001 |
| | | PP, Observed Data | 1.68 | 2.65 | −0.98 | (−1.32, −0.63) | <0.0001 |

[a]For all studies, the primary efficacy endpoints were ocular itching at 3(±1), 5(±1) and 7(±1) minutes post CAC.
[b]p-value calculated using an ANCOVA model with treatment and baseline comparing DEXTENZA and PV.

In the analysis of pooled data for conjunctival redness for all populations from the three Phase III studies, there were statistically significant differences in favor of DEXTENZA at all 3 assessment times on Day 8 and all differences were ≥0.5 unit (Table 4.8). Similar results were found in the PP population with observed data only.

TABLE 4.8

Pooled analysis of conjunctival redness on Day 8 (ITT with observed data only)

| Post-CAC times | Least Square Means | | Diff | 95% CI | p-value |
|---|---|---|---|---|---|
| | DEXTENZA N = 127 | PV N = 128 | | | |
| | All Populations | | | | |
| | n (%) | | | | |
| | 114 (89.8%) | 113 (88.3%) | | | |
| 7 min | 1.62 | 2.13 | −0.51 | (−0.71, −0.30) | <0.0001 |
| 15 min | 1.71 | 2.22 | −0.51 | (−0.72, −0.30) | <0.0001 |
| 20 min | 1.63 | 2.22 | −0.59 | (−0.81, −0.38) | <0.0001 |

Bold p-values indicate statistical significance.

Analysis of Subpopulations for Conjunctival Redness-Pooled Data of Phase III Studies Analysis of pooled data from the Phase III studies by age on Day 8 indicated statistically significant differences in conjunctival redness in favor of DEXTENZA in all age categories at all 3 post-CAC timepoints, except at the final time point (20 min) for the oldest age group (61-75 years).

Statistically significant differences in conjunctival redness in favor of DEXTENZA were observed in both males and females at all 3 post-CAC timepoints.

In the analysis of pooled data on Day 8 by race, there were statistically significant differences in conjunctival redness in favor of DEXTENZA in the race categories of Black and White at all 3 post-CAC timepoints, with all differences being >0.5 unit. The differences in the Asian population were not significant due to the small number of subjects. Similarly, in the analysis by ethnicity, significant differences in favor of DEXTENZA were observed in the non-Hispanic/Latino population at all 3 post-CAC timepoints and not in the small group of Hispanic/Latino subjects that represented 16% (40 of 255) of total study population.

The majority of subjects in the Phase III studies had brown eyes (62%) followed by those with blue eyes (19%). Overall, on Day 8, all eye colors showed statistically significant differences in conjunctival redness in favor of DEXTENZA at all 3 post-CAC timepoints. However, subjects with blue eyes revealed greater differences in favor of DEXTENZA at all post-CAC timepoints on Day 8.

Additionally, across the four clinical trials, treatment differences in favor of DEXTENZA were also observed for other secondary endpoints of eyelid swelling, tearing/watery eyes, rhinorrhea, nasal pruritus, ear or palate pruritus, nasal congestion, ciliary redness, episcleral redness, and chemosis.

Efficacy Conclusions, Allergic Conjunctivitis

DEXTENZA was demonstrated to be superior to PV for the treatment of ocular itching due to allergic conjunctivitis as evidenced by statistically significant differences in a pooled analysis of three well-controlled Phase III trials on Day 8 (7 days post-insertion) as well as in the Phase II study on Day 15 (14 days post-insertion). Across all 4 studies DEXTENZA treatment consistently resulted in lower ocular itching scores relative to PV at all study visits throughout the duration of the study up to 6 weeks, with the majority of the differences between the two treatment groups being >0.5 unit in favor of DEXTENZA. Three of these four studies met the primary endpoint of showing statistically significant differences at all 3 post-CAC timepoints at the primary endpoint visit of the study. The majority of the treatment differences at the primary endpoint (sensitivity analysis performed on ITT observed data) were approximately 1 unit at post insertion visits for studies Study 2 and Study 4. The benefit of DEXTENZA was robust and consistent across different study populations and analysis methods.

The Phase III Study 3 was an outlier among these four studies. While DEXTENZA still resulted in greater improvements in ocular itching scores relative to PV in Study 3, the effect of DEXTENZA was lower than that observed in the other studies. Two possible explanations could be that the study was conducted over a longer period spanning more than one allergic season and that there was a different demographic (fewer Black subjects) in Study 3 relative to the other three studies. Overall, the treatment effect of DEXTENZA was nearly 1 unit different from PV in Black subjects. As such, the inclusion of Study 3 in the pooled analysis of the Phase III studies lowered the overall magnitude of effect of DEXTENZA.

Treatment with DEXTENZA was also superior to PV for the treatment of conjunctival redness in subjects with allergic conjunctivitis. In the two studies that included conjunctival redness as co-primary endpoints, the Phase II Study 1 had statistically significant differences in favor of DEXTENZA in mean conjunctival redness scores at all 3 post-CAC timepoints on Day 15, and Phase III Study 2 had a p-value <0.05 at the 20 minute timepoint on Day 8. Across all four studies there were lower mean scores in conjunctival redness with DEXTENZA relative to the PV group at all visits throughout the duration of each individual study. In the analysis of pooled data for the three Phase III studies, there were statistically significant differences for conjunctival redness in favor of DEXTENZA at all 3 assessment times on Day 8 and all differences were >0.5 unit.

Additional secondary endpoints related to allergic conjunctivitis, including nasal symptoms, generally favored DEXTENZA relative to PV across all studies.

In summary, DEXTENZA was efficacious in the treatment of ocular itching and conjunctival redness associated with allergic conjunctivitis for up to 6 weeks.

Overview of Safety, Allergic Conjunctivitis
Drug Exposure, Allergic Conjunctivitis Across the four allergic conjunctivitis trials, a total of 154 subjects were exposed to at least one dose of DEXTENZA. The median duration of subject exposure to DEXTENZA was 43.0 days in Study 1, 28.0 days in Study 3, and in the other two trials (Study 2 and Study 4), exposure to DEXTENZA was for a median duration of 30.0 days, the intended duration of therapy.

A total of 583 subjects (567 with cataract surgery and 16 healthy) were exposed to DEXTENZA in the ocular inflammation and pain development program. Thus, the entire safety database for DEXTENZA (i.e., subjects exposed in any DEXTENZA clinical trial) includes a total of 737 subjects exposed to at least one dose of DEXTENZA.

Summary of Adverse Events for all Studies

Adverse events (AEs) were monitored and evaluated over the course of the four allergic conjunctivitis trials Study 1, Study 2, Study 3 and Study 4. Table 4.9 summarizes the results.

TABLE 4.9

Summary of Adverse Events for all four Studies

| Subjects with at least one: | DEXTENZA<br>N = 154<br>n (%) | Placebo<br>N = 161<br>n (%) |
|---|---|---|
| AE | 29 (18.8) | 39 (24.2) |
| Mild | 22 (14.3) | 27 (16.8) |
| Moderate | 7 (4.5) | 12 (7.5) |
| Severe | 0 | 0 |
| Treatment-related AE | 13 (8.4) | 17 (10.6) |
| Ocular AE | 19 (12.3) | 23 (14.3) |
| Treatment-related Ocular AE | 13 (8.4) | 16 (9.9) |
| Serious AE (SAE) | 1 (0.6)* | 0 |
| Treatment-related SAE | 0 | 0 |
| Ocular SAE | 0 | 0 |
| AE Leading to Study Withdrawal | 2 (1.3)† | 1 (0.6) |

AE, adverse event
*non-ocular SAE (hospitalization due to depression) was not considered related to study treatment and was recovering/resolving upon study completion
†one subject in Study 1 withdrew due to an AE (TOP increased) which resolved. One subject in Study 4 withdrew due to an AE (eye irritation) which resolved.

As shown in Table 4.9, there were no severe AEs reported; all AEs were mild or moderate in severity. No ocular SAEs were reported in either group. Only one non-ocular SAE (i.e., hospitalization due to depression) was reported in the DEXTENZA group and was deemed unrelated to treatment by the investigator.

The most common ocular AEs (>1%) that occurred in DEXTENZA-treated subjects (Table 4.10) were: increased IOP, reduced visual acuity, increased lacrimation and eye discharge. There were no reported events of dacryocanaliculitis in the DEXTENZA group across the four studies.

TABLE 4.10

Most common ocular AEs (≥1%) in DEXTENZA-treated subjects

| Subjects with: | DEXTENZA<br>N = 154<br>n (%) | Placebo<br>N = 161<br>n (%) |
|---|---|---|
| Ocular AE | 19 (12.3) | 23 (14.3) |
| Increased TOP | 5 (3.2) | 0 |
| Reduced visual acuity | 2 (1.3) | 0 |
| Increased lacrimation | 2 (1.3) | 6 (3.7) |
| Eye discharge | 2 (1.3) | 4 (2.5) |

Figure 11:
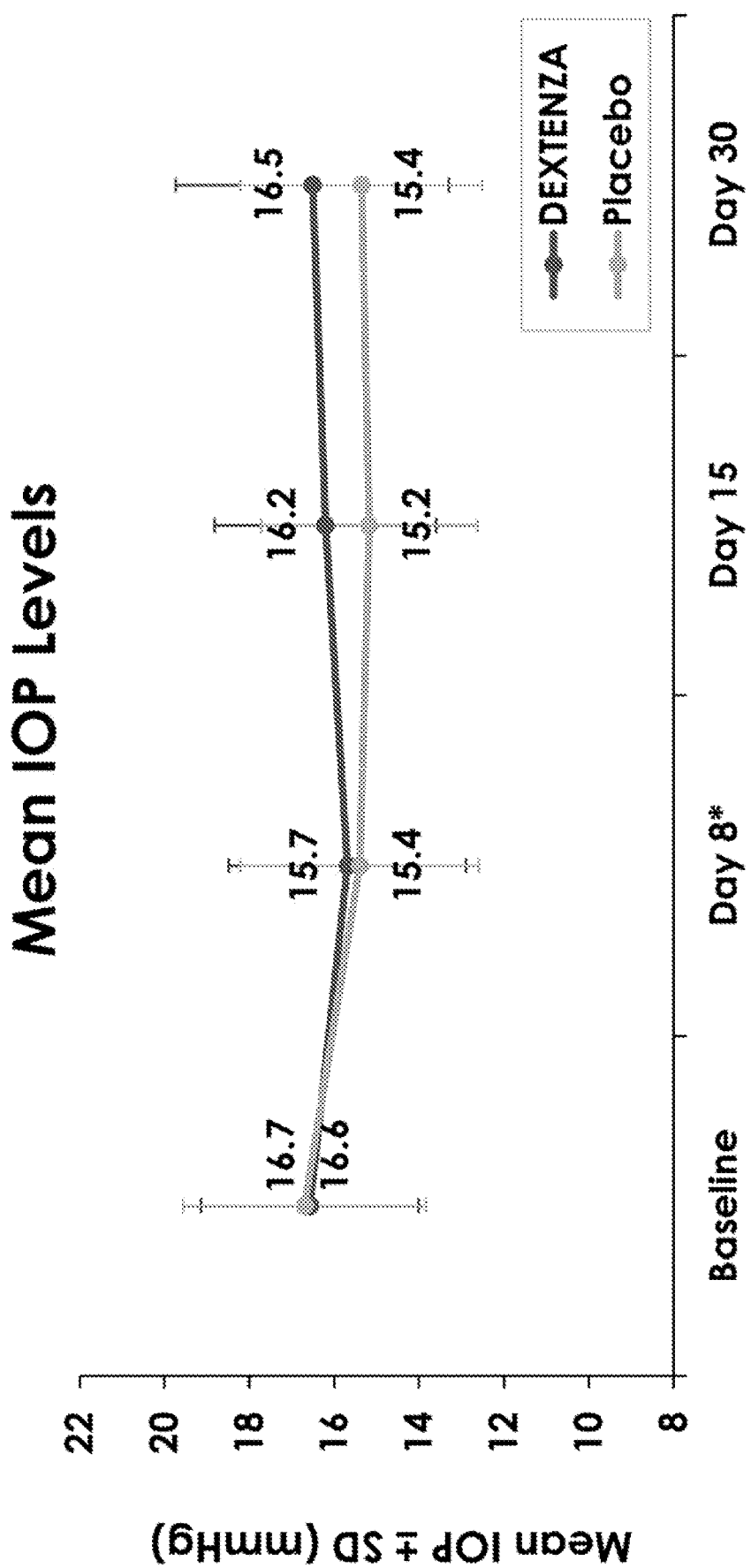
FIG. 11 shows mean intraocular pressure (IOP) levels across one Phase II and three Phase III studies in patients who reported an IOP adverse event.

FIG. 11 presents the mean IOP levels in patients who reported increased IOP. The mean IOP levels were about 15.2 to about 16.7 mmHg. Normal eye pressure ranges from 10-21 mm Hg. Ocular hypertension is an eye pressure of greater than 21 mm Hg. The mean IOP findings showed that subjects maintained normal ranges and this was consistent across study visits. The rates of increased IOP following treatment with a glucocorticoid hydrogel insert were low (about 3.2%) and comparable to topical ophthalmic formulations containing loteprednol. This result is unexpected and surprising because topical drop dexamethasone is commonly associated with 20%-30% incidence of IOP spikes. See, e.g., Avraham Cohen (2011). Steroid Induced Glaucoma, Glaucoma—Basic and Clinical Concepts, Dr Shimon Rumelt (Ed.), p. 4, § 4.1 ISBN: 978-953-307-591-4, InTech, Available from: http://www.intechopen.com/books/glaucomabasic-and-clinical-concepts/steroid-induced-glaucom (dexamethasone increases IOP more frequently than Lotemax); see also Kersey et al., Corticosteroid Induced Glaucoma a Review of the Literature, Eye (2006) 20, 407-416, 407, Table 1 (In steroid responders Maxidex (0.1% dexamethasone) showed the highest IOP spikes averaging greater than 22 mmHg; the potency directly correlates with hypertensive effect. Glucocorticoid hydrogel inserts (e.g., Dextenza), however, deliver similar AUC levels as dexamethasone eyedrops (Maxidex), but has IOP spikes similar to less potent loteprednol (Alrex); see also Roberti, et al., Steroid-Induced Glaucoma: Epidemiology, Pathophysiology, and Clinical Management, Survey of Opthamology 65 (2020) 458-472, 452, § 5.1, Table 1 (dexamethasone has a greater IOP increase and the greatest proportion of patients to develop hypertension as compared to lotepred); see also Phulke S, et al., Steroid-induced Glaucoma: An Avoidable Irreversible Blindness, J. Curr Glaucoma Pract. 2017; 11(2):67-72 (Table 2 shows 5% of the general population are high steroid responders and 35% of the general population are intermediate steroid responders); see also Feroze K B, et al., Steroid Induced Glaucoma (StatPearls Publishing; January 2021), available at https://www.ncbi.nlm.nih.gov/books/NBK430903/(Under "Epidemiology", 4 to 6% of population are high steroid responders and ~33% are moderate responders); see also Tripathi R C, et al., Corticosteroids and Glaucoma Risk, Drugs Aging 15(6):439-50 (December 1999) ("Approximately 18 to 36% of the general population are corticosteroid responders.").

Loteprednol is considered a less potent "softer" steroid as compared to dexamethasone, and is often used to address some of the safety challenges with topical drop dexamethasone, which is considered a potent "hard" steroid. The inserts as described herein are able to deliver a potent steroid (e.g., dexamethasone) associated with good efficacy, but in a safer manner comparable to less potent, softer steroids. Moreover, the inserts described herein avoid the high rate of IOP spikes associated with topical dexamethasone. In certain embodiments, the present invention overcomes the historical challenge of topical dexamethasone by reducing IOP spikes while delivering the efficacy of a high potency steroid (e.g., dexamethasone).

The hydrogel inserts of the present invention further provides a controlled release of the glucocorticoid (e.g., dexamethasone). Topical drops are a relatively inefficient means of drug delivery. For example, less than 10% (e.g., about 4%) of the active agent in a drop actually makes it into the eye—due to absorption and compliance reasons (e.g., inefficient delivery). To overcome this inefficiency, topical drops are often formulated at a relatively high concentration to maximize the amount of drug that makes it to the eye and this is often associated with a high $C_{max}$ at an acute time point. However the drug concentration, following application to the eye, falls quickly, which is the reason frequent daily drop dosing is needed. The present hydrogel inserts release the drug in a controlled manner throughout its use. In a pair of studies, the dexamethasone concentration in the aqueous humor (AH) of canines after administration of MAXIDEX topical dexamethasone drops (0.1% dexamethasone) or administration of DEXTENZA (0.46 mg) was evaluated. For MAXIDEX, the average per timepoint dexamethasone AH concentrations were 1.6-22.2 ng/mL; specific to high concentrations, 50% of timepoint average readings were >8 ng/mL and the max reading observed was 50.7 ng/mL. For DEXTENZA, the average per timepoint dexamethasone AH concentrations were 7.5 to 7.9 ng/mL over 21 days with no timepoint average >8 ng/mL and a max reading observed was 11.8 ng/mL. It is believed that preventing large spikes in dexamethasone concentration in the eye may prevent large IOP spikes.

Additionally, as compared to topical dexamethasone drop formulations, a single dose of DEXTENZA lasts for 30 days whereas a single dose of topical drop formulations lasts only about 6-24 hours and must be administered one or more times per day. In clinical trials, topical dexamethasone drops are dosed daily and a CAC challenge is conducted in close proximity to the dosing (i.e., within hours). For topical dexamethasone drop formulations, the Day 8 challenge evaluates a drop that was applied shortly prior to a challenge (i.e., within minutes to hours). For DEXTENZA, there is a single dose and then at subsequent days that original dose is challenged (i.e., the Day 8 challenge is evaluating a dosing 7 days prior). Although not primary endpoints, the DEXTENZA CAC studies discussed in this Example 4 involved challenges 15-30 days after DEXTENZA dosing. In effect, more dexamethasone is administered using the topical dexamethasone formulation to account for, e.g., inefficient delivery, absorption issues and daily or multiple daily administration. Nonetheless, the area under the curve (AUC) for DEXTENZA was equivalent to that of a topical dexamethasone drop formulation even though dosing via the insert was days or weeks prior. In summary, the duration of effect of hydrogel inserts is unexpectedly superior to topical drop formulations. Historically, prolonged dexamethasone administration to the eye via a topical drop route has resulted in extensive adverse events (e.g., IOP spikes).

Summary of Tearing/Watery Eyes Secondary Endpoint

Tearing/watery eyes were evaluated by the subject (on a 0-4 scale, 0 being no tearing) as part of secondary efficacy endpoint in the Studies 1-4 discussed in Example 4. Across all of the studies, at all timepoints measured, the average of the mean tearing/watery eyes score for DEXTENZA was lower than for the placebo.

Summary of CAC Measurements Performed on Subjects Before Insertion of an Insert (Studies 2-4)

CAC challenges were performed on subjects prior to insertion of either the DEXTENZA or PV inserts. The itching scores showed a benefit of treatment with the dexamethasone insert (DEXTENZA) or placebo. The itching scores pre-insertion (−visit day) and pre-CAC were 0.24 to 0.57. After insertion of the insert, the itching scores pre-CAC were consistently lower at 0.12 to 0.17.

The redness scores also showed a benefit of treatment with the dexamethasone insert (DEXTENZA) or placebo. The redness scores pre-insertion (−visit day) and pre-CAC were 0.59 to 1.28 and nearly all means were greater than 1. After insertion, the redness scores pre-CAC were consistently lower at 0.73 to 0.93 with no means greater than 1.

Example 5: Efficacy and Safety of Intracanalicular Dexamethasone Inserts (0.4 mg) for the Treatment of Allergic Conjunctivitis The safety and efficacy of intracanalicular dexamethasone inserts (DEXTENZA; DEX) were evaluated for ocular itching and conjunctival redness due to allergic conjunctivitis (AC) using a repetitive Conjunctival Allergen Challenge (CAC) Model. Allergic conjunctivitis is a prevalent, allergen-induced, inflammatory-mediated eye disorder that places a burden on patients and healthcare practices. Current topical drop therapies have limitations including potential for noncompliance, preservatives toxicity, and abuse/misuse. DEXTENZA (dexamethasone ophthalmic insert) 0.4 mg is a resorbable, preservative-free, hydrogel-based insert placed into the punctum that delivers a tapered dose of steroid over 30 days to the ocular surface and can potentially address challenges with current drop therapies for allergic conjunctivitis (AC).

A pooled analysis of randomized, controlled clinical trials assessing efficacy (three Phase III) and safety (one Phase II and three Phase III) was performed. DEX or vehicle (PV) was inserted bilaterally. On Day 8, ocular itching was assessed at 3, 5 and 7 min post-CAC and conjunctival redness was assessed at 7, 15 and 20 min post-CAC. Safety assessments included adverse events (AE) collection.

On Day 8, DEX (n=127) significantly lowered mean ocular itching scores 3, 5 and 7 min post-CAC (P<0.01) and mean conjunctival redness scores 7, 15 and 20 min post-CAC (P<0.01) compared to PV (n=128). Fewer ocular AEs were reported in the DEX group (n=154) compared to PV (n=161). The most common ocular AE in DEX group was increased IOP (3.2%). DEXTENZA IOP spikes were similar to low potency steroids (i.e., loteprednol, LOTEMAX® 0.5%, ALREX® 0.2%) used to treat allergic conjunctivitis, which is unexpected and surprising. Because of its lower potency, loteprednol has been used as a substitute for DEX topical drop formulation to reduce or avoid IOP spikes. DEXTENZA overcomes the limitations of high potency steroids by reducing IOP spikes seen with topical DEX (20+%). The occurrence of DEXTENZA IOP spikes is similar to low potency topical steroids.

The results demonstrated that in a pooled analysis, DEXTENZA was superior to placebo for treating ocular itching and conjunctival redness due to allergic conjunctivitis and was generally safe with a low risk of elevated IOP. The pooled analysis showed DEXTENZA had a favorable safety profile and provided relief from ocular itching and conjunctival redness due to AC. These data support glucocorticoid hydrogel inserts as an alternative to conventional steroid drops for AC.

Example 6: Ocular Surface Response to Resorbable Hydrogel Intracanalicular Insert Resorbable hydrogel intracanalicular inserts affect ocular itching and conjunctival redness associated with allergic conjunctivitis (AC). Three randomized, double-masked, vehicle-controlled Phase III trials were conducted using a repetitive conjunctival allergen challenge (CAC) model to compare the effect of hydrogel insert with dexamethasone 0.4 mg and without on the AC response. The hydrogel platform is a vehicle for sustained drug delivery including for a novel resorbable dexamethasone intracanalicular insert (dexamethasone ophthalmic insert, 0.04 mg). Post-hoc pooled analyses of Phase III trials conducted using a CAC model, demonstrate hydrogel insert without medication alone does not make the ocular itching and conjunctival redness scores worse over time, but, reduces them in subjects with AC. This is surprising and unexpected because one of ordinary skill in the art would expect that occluding the puncta could result in allergens spending more time on the ocular surface resulting in reduced efficacy. However, the glucocorticoid insert did not reduce efficacy.

Ocular itching was assessed at 3, 5 and 7 min post-CAC and conjunctival redness at 7, 15 and 20 min post-CAC, on days 7, 14 and 28 post administration. Post-hoc pooled analyses were conducted to investigate the impact of hydrogel insert without medication on the itching and redness scores associated with AC over time, compared to baseline. Pooled analyses averaging both eyes (n=128 patients) showed statistically significant decline (p<0.001) in both itching and redness scores on days 7 (itching 26%, redness 34%), 14 (itching 35%, redness 36%) and 28 (itching 45%, redness 32%) compared to baseline. The resorbable hydrogel intracanalicular insert placement does not make ocular itching and conjunctival redness worse in subjects with AC.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular implementations may vary from these exemplary details and still be contemplated to be within the scope of the present disclosure.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

The invention claimed is:

1. A method of treating allergic conjunctivitis in a patient in need thereof, the method comprising administering to the canaliculus of the patient a completely formed sustained release biodegradable intracanalicular insert consisting essentially of dexamethasone, 4-arm20kPEG-SG, trilysine acetate, fluorescein, sodium phosphate monobasic, sodium phosphate dibasic and water;
   the insert having an essentially cylindrical shape;
   the insert being preservative-free;
   wherein the ophthalmic insert releases about 0.4 mg of dexamethasone following administration;
   wherein the occurrence of increase in intraocular pressure in a population of allergic conjunctivitis patients is about 3% or less in the population; and
   wherein the administration is safe and effective for the treatment of allergic conjunctivitis.

2. The method of claim 1, wherein the insert provides an ocular itching score of about 1.7 to about 2.1 on Day 8 of use when measured at 3 minutes, 5 minutes or 7 minutes post-challenge as measured using a modified Conjunctival Allergen Challenge Model.

3. A method of treating allergic conjunctivitis in a patient in need thereof, the method comprising administering to the canaliculus of the patient a completely formed sustained release biodegradable intracanalicular insert consisting of dexamethasone, 4-arm20kPEG-SG, trilysine acetate, fluorescein, sodium phosphate monobasic, sodium phosphate dibasic and water;
   the insert having an essentially cylindrical shape;
   the insert being preservative-free;
   wherein the ophthalmic insert releases about 0.4 mg of dexamethasone following administration;
   wherein the occurrence of increase in intraocular pressure in a population of allergic conjunctivitis patients is about 3% or less in the population; and
   wherein the administration is safe and effective for the treatment of allergic conjunctivitis.

4. A method of treating allergic conjunctivitis in a patient in need thereof, the method comprising administering to the canaliculus of the patient a completely formed sustained release biodegradable intracanalicular insert comprising a hydrogel and dexamethasone having a particle size of less than about 100 μm;
   the hydrogel comprising a polymer network comprising one or more crosslinked 4-arm polyethylene glycol units having an average molecular weight of about 20,000 Daltons;
   the polymer network being formed by reacting an electrophilic group-containing multi-arm-polymer precursor with a nucleophilic group-containing crosslinking agent;
   the electrophilic group-containing multi-arm-polymer precursor comprising 4-arm 20kPEG-SG and the crosslinking agent comprising trilysine acetate;
   the insert having an essentially cylindrical shape;
   the insert being preservative-free;
   the insert in a dry state comprising one or more phosphate, borate or carbonate salt(s);
   the insert comprising a visualization agent comprising fluorescein conjugated with trilysine acetate;
   wherein the ophthalmic insert releases about 0.4 mg of dexamethasone following administration;
   wherein the occurrence of increase in intraocular pressure in a population of allergic conjunctivitis patients is about 3% or less in the population; and
   wherein the administration is safe and effective for the treatment of allergic conjunctivitis.

5. A method of treating allergic conjunctivitis in a patient in need thereof, the method comprising administering to the canaliculus of the patient a completely formed sustained release biodegradable intracanalicular insert comprising a hydrogel and dexamethasone;
   the hydrogel comprising a polymer network comprising one or more crosslinked 4-arm polyethylene glycol units having an average molecular weight of about 20,000 Daltons;
   the polymer network being formed by reacting an electrophilic group-containing multi-arm-polymer precursor with a nucleophilic group-containing crosslinking agent;
   the electrophilic group-containing multi-arm-polymer precursor comprising 4-arm 20kPEG-SG and the crosslinking agent comprising trilysine acetate;
   the insert having an essentially cylindrical shape;
   the insert in a dry state having an average length of about 3 mm;
   the insert being preservative-free;
   the insert in a dry state comprising one or more phosphate, borate or carbonate salt(s);
   the insert comprising a visualization agent comprising fluorescein conjugated with trilysine acetate;
   wherein the ophthalmic insert releases about 0.4 mg of dexamethasone following administration;
   wherein the occurrence of increase in intraocular pressure in a population of allergic conjunctivitis patients is about 3% or less in the population; and
wherein the administration is safe and effective for the treatment of allergic conjunctivitis.

6. The method of claim 3, wherein the insert provides an ocular itching score of about 1.7 to about 2.1 on Day 8 of use when measured at 3 minutes, 5 minutes or 7 minutes post-challenge as measured using a modified Conjunctival Allergen Challenge Model.

7. The method of claim 4, wherein the insert provides an ocular itching score of about 1.7 to about 2.1 on Day 8 of use when measured at 3 minutes, 5 minutes or 7 minutes post-challenge as measured using a modified Conjunctival Allergen Challenge Model.

8. The method of claim 5, wherein the insert provides an ocular itching score of about 1.7 to about 2.1 on Day 8 of use when measured at 3 minutes, 5 minutes or 7 minutes post-challenge as measured using a modified Conjunctival Allergen Challenge Model.

* * * * *